US012758204B2

(12) United States Patent
Yorita et al.

(10) Patent No.: US 12,758,204 B2
(45) Date of Patent: Oct. 13, 2026

(54) CLIP DEVICE AND CLIP SYSTEM

(71) Applicant: OLYMPUS MEDICAL SYSTEMS CORP., Tokyo (JP)

(72) Inventors: Ryu Yorita, Tokyo (JP); Toshinori Tamura, Hirosaki (JP); Jun Shirai, Tachikawa (JP); Naoki Takizawa, Musashino (JP); Shogo Shindo, Hachioji (JP); Kensuke Uesaka, Hino (JP); Masaru Yuasa, Hachioji (JP)

(73) Assignee: OLYMPUS MEDICAL SYSTEMS CORP, Tokyo (JP)

(*) Notice: Subject to any disclaimer, the term of this patent is extended or adjusted under 35 U.S.C. 154(b) by 272 days.

(21) Appl. No.: 18/758,842

(22) Filed: Jun. 28, 2024

(65) Prior Publication Data

US 2025/0000499 A1 Jan. 2, 2025

Related U.S. Application Data

(60) Provisional application No. 63/511,246, filed on Jun. 30, 2023.

(51) Int. Cl.
*A61B 17/00* (2006.01)

(52) U.S. Cl.
CPC .... *A61B 17/0057* (2013.01); *A61B 17/00234* (2013.01); *A61B 2017/00296* (2013.01); *A61B 2017/00477* (2013.01); *A61B 2017/00623* (2013.01)

(58) Field of Classification Search
CPC .......... A61B 17/0057; A61B 17/00234; A61B 17/122; A61B 17/1227; A61B 17/128; A61B 17/1285; A61B 2017/00296; A61B 2017/00477; A61B 2017/00623; A61B 2017/0053
See application file for complete search history.

(56) References Cited

U.S. PATENT DOCUMENTS

| | | | | |
|---|---|---|---|---|
| 11,076,862 | B2 * | 8/2021 | Uesaka | A61B 17/1227 |
| 11,426,177 | B2 * | 8/2022 | Congdon | A61B 17/1227 |
| 11,690,634 | B2 * | 7/2023 | Rausa | A61B 17/122 606/142 |
| 12,016,570 | B2 * | 6/2024 | Akiyoshi | A61B 17/128 |
| 12,357,318 | B2 * | 7/2025 | Uesaka | A61B 17/083 |
| 2018/0015276 | A1 * | 1/2018 | Ueda | A61J 1/14 |
| 2018/0153552 | A1 * | 6/2018 | King | A61B 17/128 |
| 2019/0159783 | A1 * | 5/2019 | Lehtinen | A61B 17/1285 |
| 2020/0205836 | A1 * | 7/2020 | Uesaka | A61B 17/083 |
| 2021/0022744 | A1 | 1/2021 | Rausa et al. | |

(Continued)

*Primary Examiner* — Ryan J. Severson
(74) *Attorney, Agent, or Firm* — Schwegman Lundberg & Woessner, P.A.

(57) ABSTRACT

A clip device can include a clip including a pair of clip arms, a capsule including a channel, the channel slidably inserted into a proximal end of each clip arm of the pair of clip arms, and a coupler attached onto the proximal end of the capsule. The coupler includes a pair of deployment arms and a pair of retention arms. The pair of retention arms are configured to engage with a corresponding portion of an applicator. Wherein a first length of the coupler in a first direction is longer than a second length of the coupler in a second direction in a cross-section. The cross-section crosses the pair of retention arms and the pair of deployment arms and is perpendicular to a longitudinal direction of the coupler.

20 Claims, 56 Drawing Sheets

(56) References Cited

U.S. PATENT DOCUMENTS

| | | | | |
|---|---|---|---|---|
| 2021/0322024 | A1* | 10/2021 | Uesaka | A61B 17/10 |
| 2025/0000499 | A1* | 1/2025 | Yorita | A61B 17/1285 |
| 2025/0312047 | A1* | 10/2025 | Uesaka | A61B 17/1285 |

* cited by examiner

CLIP DEVICE AND CLIP SYSTEM

CROSS-REFERENCE TO RELATED APPLICATIONS

The present application claims priority based on U.S. Patent Provisional Application No. 63/511,246 filed in the United States on Jun. 30, 2023, the contents of which are incorporated herein by reference.

TECHNICAL FIELD

The present disclosure relates to a clip device and a clip system.

BACKGROUND

In endoscopic treatment, a clip unit can be used which can ligate a resected portion or the like after a procedure to stop bleeding. The clip unit can include a clip holding the resected portion or the like and a capsule to accommodate or store the clip and to lock the clip in a closed state or the like. The clip unit can be introduced to a treatment position by an applicator (introducer) that can be inserted through a channel of an endoscope.

US Patent Application Publication No. 2021/0022744 (Patent Document 1) describes a clip system capable of reloading a clip unit into an applicator. A user can reload the clip unit using a cartridge system.

SUMMARY

In the clip system described in Patent Document 1, when the clip system is inserted through the channel of the endoscope, the coupler that connects the clip unit and the applicator tends to come into contact with the inner peripheral surface of the channel. When the coupler comes into contact with the inner peripheral surface of the channel, the coupler tends to fall off from the applicator.

In view of the above-described circumstances, the present disclosure describes a clip device and a clip system capable of easily passing a coupler connecting a clip unit and an applicator through a channel of an endoscope.

A clip device according to a first aspect of the present disclosure may be a clip device for treating tissue. The clip device can include a clip including a pair of clip arms, a capsule including a channel, the channel slidably inserted into a proximal end of each clip arm of the pair of clip arms, and a coupler attached onto the proximal end of the capsule. The coupler includes a pair of deployment arms and a pair of retention arms. The pair of retention arms are configured to engage with a corresponding portion of an applicator. Wherein a first length of the coupler in a first direction is longer than a second length of the coupler in a second direction in a cross-section. The cross-section crosses the pair of retention arms and the pair of deployment arms and is perpendicular to a longitudinal direction of the coupler.

A clip system according to a second aspect of the present disclosure can be a clip system for treating tissue. The clip system includes a clip including a pair of clip arms, a capsule including a channel, the channel slidably inserted into a proximal end of each clip arm of the pair of clip arms, a coupler attached onto the proximal end of the capsule, the coupler including a pair of deployment arms and a pair of retention arms, and an applicator including a sheath and a wire extending through the sheath, the wire including a connector connected to the pair of clip arms. Wherein a first length of the coupler in a first direction is longer than a second length of the coupler in a second direction in a cross-section. The cross-section crosses the pair of retention arms and the pair of deployment arms and is perpendicular to a longitudinal direction of the coupler.

The clip device and the clip system of the present disclosure can easily pass the coupler connecting the clip unit and the applicator through the channel of the endoscope.

BRIEF DESCRIPTION

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

First Embodiment

A first embodiment of the present disclosure will be described with reference to FIGS. 1 to 15.

Figure 1:
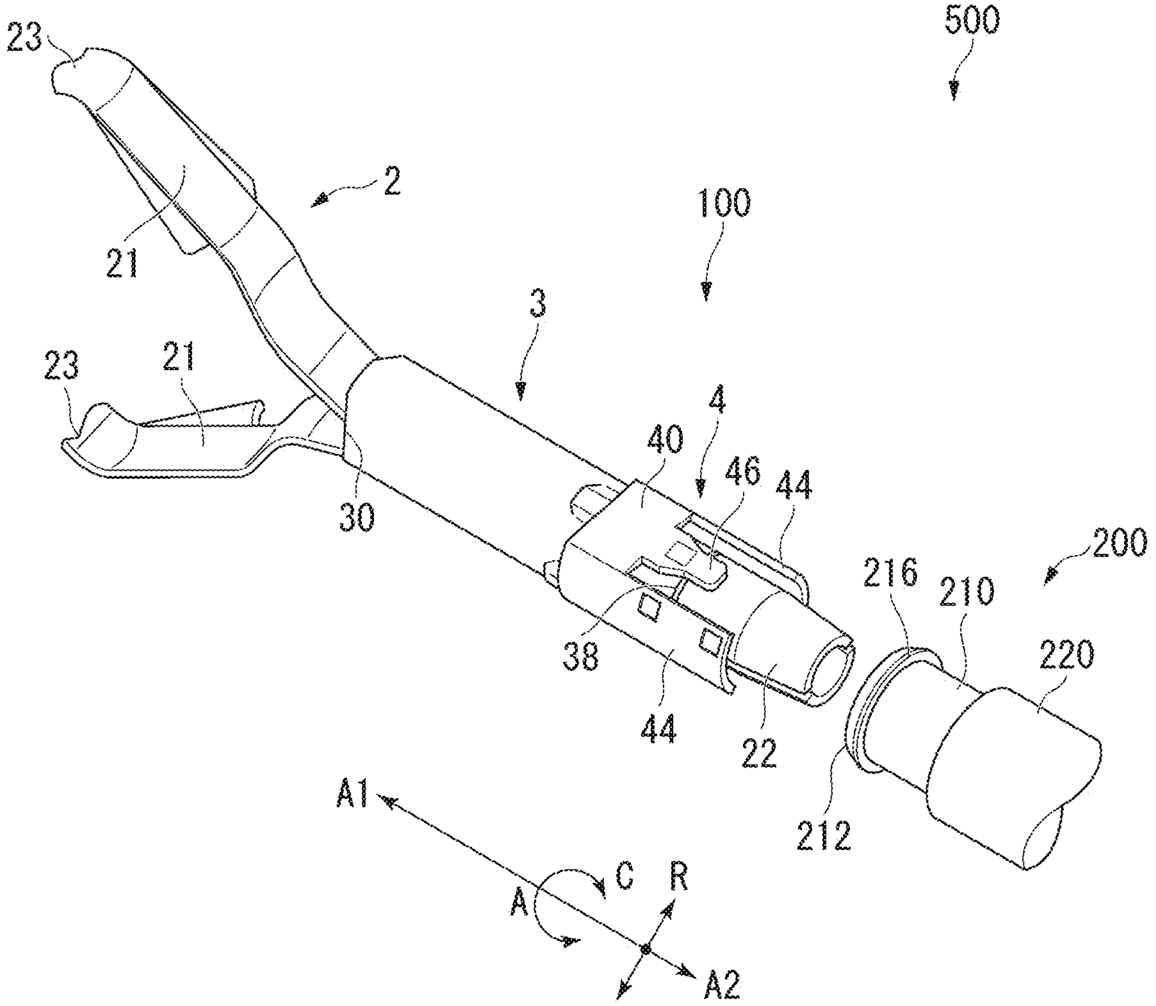
FIG. 1 illustrates an example of a diagram showing a part of a clip system according to a first embodiment of the present disclosure.

FIG. 1 illustrates an example diagram showing a part of a clip system 500.

A clip system 500 according to this embodiment can include a clip unit 100, an applicator 200, and a cartridge 300. The clip unit 100 can be loaded into the applicator 200 using the cartridge 300.

The clip unit (clip device, clip assembly) 100 can include a clip 2, a capsule 3, and a coupler 4. In the following description, the side of the clip 2 in the longitudinal direction A of the clip unit 1 is referred to as the front end side (distal side, distal direction) A1 of the clip unit 100 and the side of the coupler 4 is referred to as the base end side (proximal side, proximal direction) A2 of the clip unit 100. Further, a direction perpendicular to the longitudinal direction A is referred to as the radial direction R.

Figure 2:
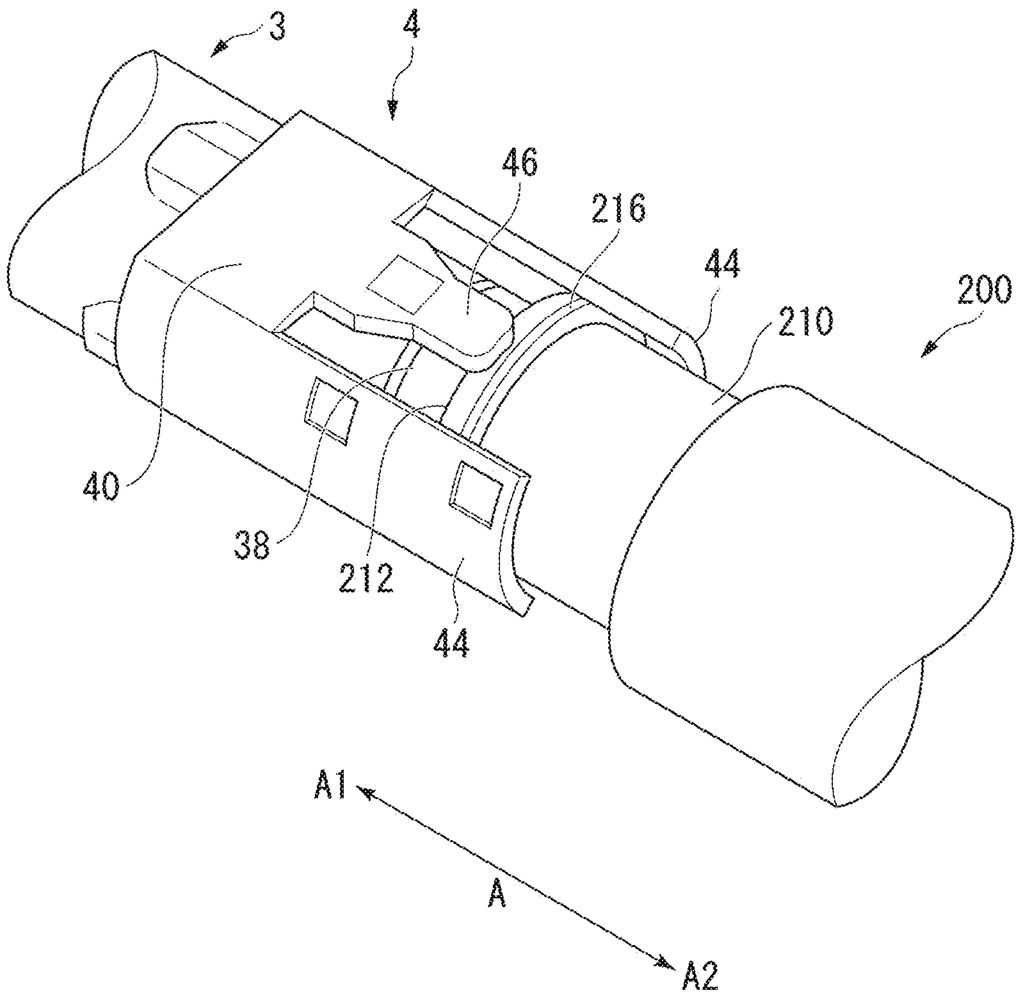
FIG. 2 illustrates an example of a perspective view of the same clip unit of FIG. 1 loaded into an applicator.

FIG. 2 illustrates an example perspective view of the clip unit 100 loaded into the applicator 200.

The clip unit 100 can be loaded into the distal end of the applicator 200 via the coupler 4. When the clip 2 is deployed to a target site within the body, a new clip unit 100 can be reloaded into the applicator 200.

The clip 2 can include a pair of clip arms 21 that can be opened and closed and a yoke 22 that connects the pair of clip arms 21.

The pair of clip arms 21 can be opened and closed toward the front end side to grip tissue. The proximal ends of the pair of clip arms 21 can be connected to each other via the yoke 22 slidably inserted into the capsule 3. The pair of clip arms 21 can transition between an open state in which the distal ends 23 of the pair of clip arms 21 move away from each other and a closed state in which the distal ends 23 move close to each other to grip tissue.

The pair of clip arms 21 can be biased to be in an open state. Therefore, when the pair of clip arms 21 are not restrained by the capsule 3, the pair of clip arms 21 are in an open state due to self-expanding force. When the pair of clip arms 21 is pulled into the capsule 3, the capsule 3 can restrain the pair of clip arms 21 and can support both distal ends 23 such that the tissue can be gripped between the pair of clip arms 21.

Each of the pair of clip arms 21 can extend from the proximal end connected to the yoke 22 to the distal end 23. The distal ends 23 of one or both of the pair of clip arms 21 can include a front end that extends toward the other clip arm 21. The front end can include structures such as teeth, protrusions, and spikes configured to grip tissue between the distal ends 23.

The clip 2 can include a locking element configured to lock the pair of clip arms 21 in the tissue gripped manner after the tissue has been gripped by the pair of clip arms 21. In one embodiment, the clip 2 can include a locking tab as a locking element. The locking tab can include a projection extending outward in the radial direction R from the pair of clip arms 21. When the pair of clip arms 21 are pulled into the capsule 3 by a predetermined distance, the locking tab can engage with a part of the capsule 3. For example, the locking tab can be received within a locking window extending in the radial direction R from the inner peripheral surface of the capsule 3. As a result, the pair of clip arms 21 can be locked to the capsule 3 while gripping the tissue.

Figure 3:
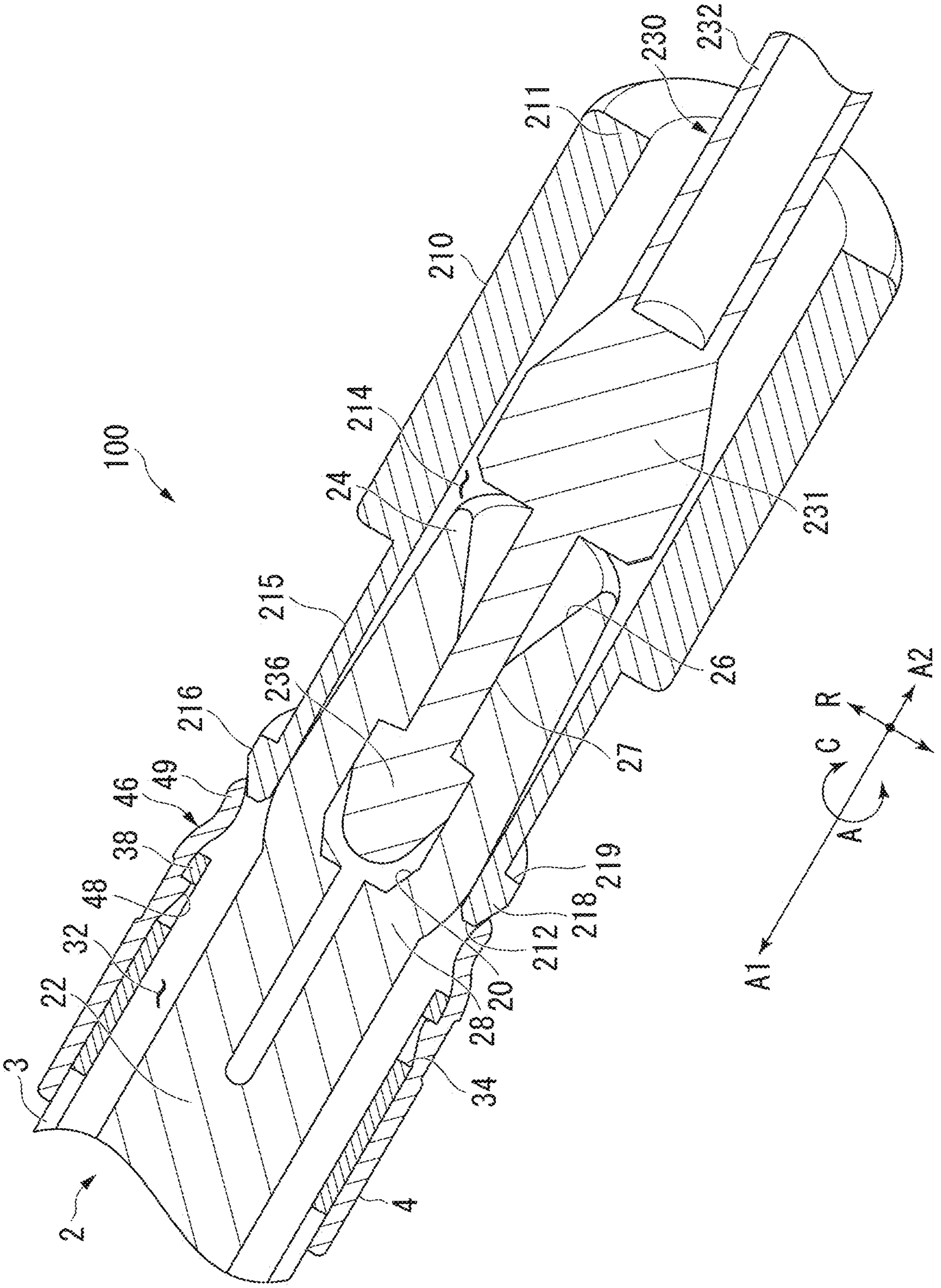
FIG. 3 illustrates an example of a cross-sectional view of the same clip unit of FIG. 1 loaded into the same applicator of FIG. 2.

FIG. 3 illustrates an example cross-sectional view of the clip unit 100 loaded into the applicator 200.

The yoke 22 can be provided at the proximal ends of the pair of clip arms 21. The yoke 22 can be slidable inside the capsule 3 in the longitudinal direction A. As the yoke 22 moves toward the distal side with respect to the capsule 3, the pair of clip arms 21 can transition to an open state. As the yoke 22 moves toward the proximal side with respect to the capsule 3, the pair of clip arms 21 can transition to a closed state.

The yoke 22 can include a proximal portion 28 and a distal portion configured to separate from each other when subjected to a force exceeding a predetermined threshold. The proximal portion 28 and the distal portion can be, for example, portions that break or separate when a predetermined force is applied.

The yoke 22 can be configured to be connected to an enlarged distal end 236 of a connection member 231 of the applicator 200. Specifically, the proximal portion 28 of the yoke 22 can be formed to engage with the enlarged distal end 236 of the connection member 231. The proximal portion 28 can include a cavity 20 with a size and shape capable of receiving the enlarged distal end 236 and a slot 27 which extends in the proximal direction from the cavity 20 to a proximal end 24 of the yoke 22. The slot 27 can be formed with a size and shape capable of receiving a part of the connection member 231 extending in the proximal direction from the enlarged distal end 236.

The opening of the slot 27 at the proximal end 24 can include an inclined surface 26 tapered toward the distal end of the opening. The inclined surface 26 can facilitate the insertion of the enlarged distal end 236 into the cavity 20 to pass through the slot 27 in the distal direction when the clip unit 100 is loaded into the applicator 200. In the cavity 20 and the slot 27, when the enlarged distal end 236 is pressed into the cavity 20 through the slot 27, the diameter of the slot 27 can be decreased to prevent the enlarged distal end 236 from being withdrawn from the slot in the proximal direction. Thus, the pair of clip arms 21 can transition between an open state and a closed state by advancing and retracting the connection member 231 in the longitudinal direction A with respect to the capsule 3.

The capsule (presser tube) 3 can be formed in a substantially cylindrical shape. The capsule 3 can extend from a proximal end 38 to a distal end 30 in the longitudinal direction and can include a channel 32 extending in the longitudinal direction through the capsule 3. The channel 32 can have (e.g., be formed with) a size and shape capable of slidably receiving the yoke 22 and the pair of clip arms 21 into the channel 32.

As described above, the capsule 3 can also include a locking structure (for example, a locking recess or a locking window) for engaging a corresponding locking element (for example, a locking tab) of the clip 2.

The capsule 3 can also include an opening 34 extending through the inner wall of the capsule 3 along the proximal end 38. As will be described in more detail later, the opening 34 has a size and shape capable of receiving engagement elements 48 of a pair of deployment arms 46 of the coupler 4.

Figure 4:
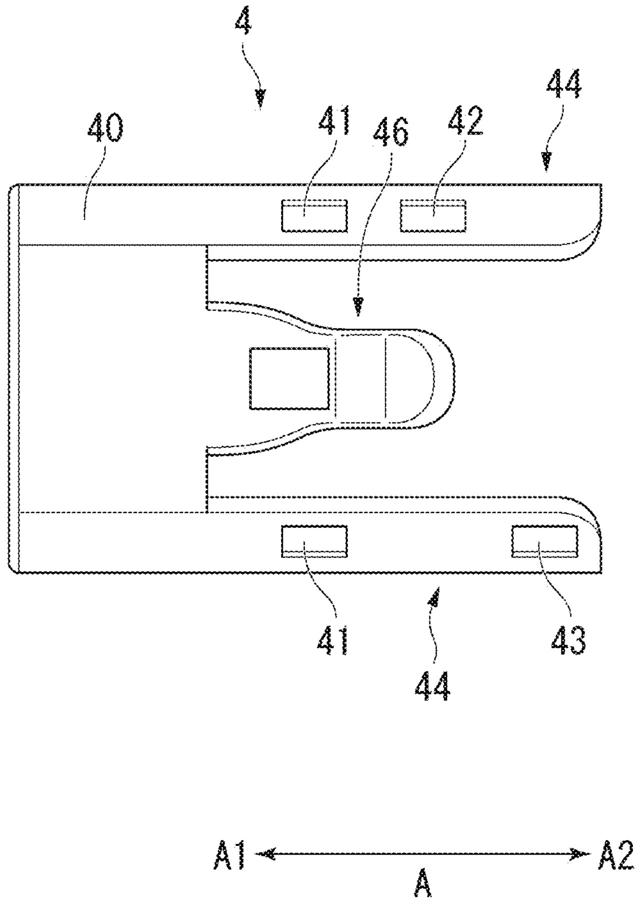
FIG. 4 illustrates an example of a diagram showing a coupler of the same clip unit of FIG. 1.

FIG. 4 illustrates an example diagram showing the coupler 4.

The coupler 4 can be connected to the proximal end 38 of the capsule 3 of the clip unit 100 before the clip unit 100 is loaded into the applicator 200. The coupler 4 can include a distal portion 40, a pair of retention arms 44, and the pair of deployment arms 46. The pair of retention arms 44 can be connected to a bushing 210 of the applicator 200 in a separable manner. The pair of deployment arms 46 can be connected to the capsule 3 in a separable manner. That is, the coupler 4 can connect the bushing 210 of the applicator 200 and the capsule 3 in a separable manner.

The distal portion (cylindrical portion) 40 can have or be formed with a size and shape to be attachable to the capsule 3 and can have or be formed with a substantially cylindrical shape in this embodiment. The pair of retention arms 44 and the pair of deployment arms 46 can extend from the distal portion 40 in the proximal direction. The retention arm 44 and the deployment arm 46 can be arranged alternately in the circumferential direction C of the coupler 4. The pair of retention arms 44 can substantially face each other in the radial direction R. The pair of deployment arms 46 can substantially face each other in the radial direction R. The retention arm 44 and the deployment arm 46 can be arranged at equal intervals.

Figure 5:
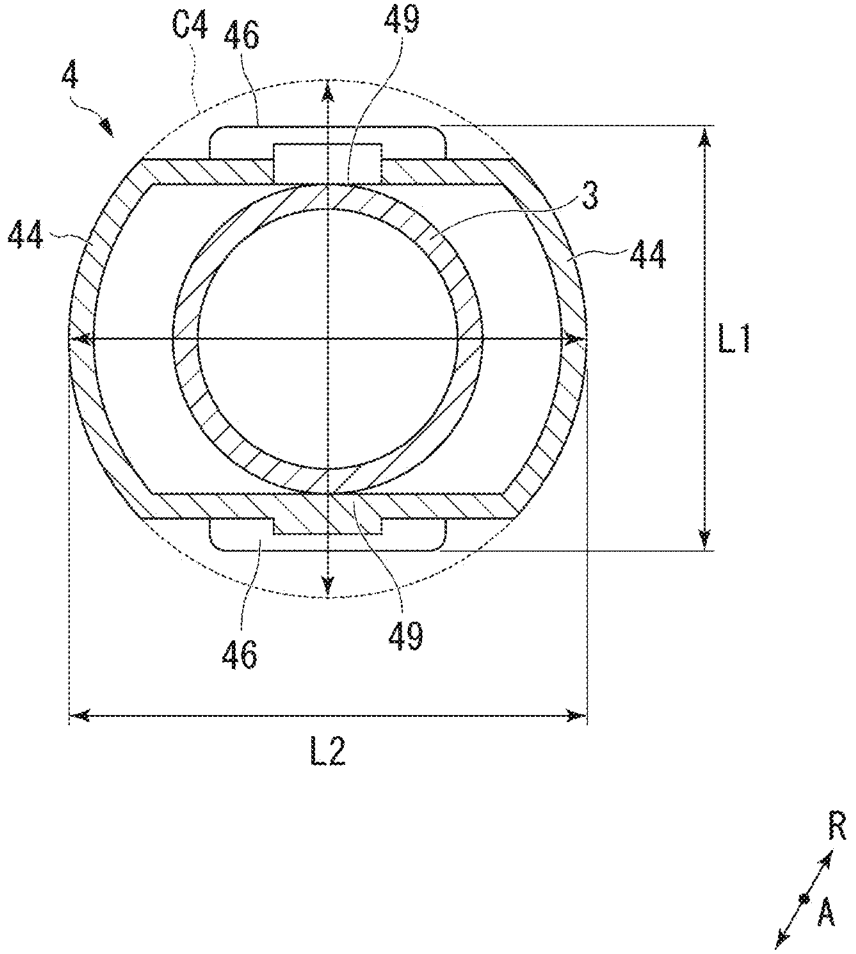
FIG. 5 illustrates an example of a cross-sectional view of the same coupler of FIG. 4.

FIG. 5 illustrates an example cross-sectional view of the coupler 4.

The outer diameter L1 of the coupler 4 in the direction in which the pair of deployment arms 46 face each other in the radial direction R can be shorter than the outer diameter L2 of the coupler 4 in the direction in which the pair of retention arms 44 face each other in the radial direction R. In the cross-section along the radial direction R, the pair of deployment arms 46 can be arranged on the inside of the largest circumscribed circle C4 of the coupler 4. The pair of retention arms 44 can be arranged on the largest circumscribed circle C4 of the coupler 4.

The coupler 4 can be made of stainless steel material, for example, and can be manufactured by metal pressing and rolling.

Figure 6:
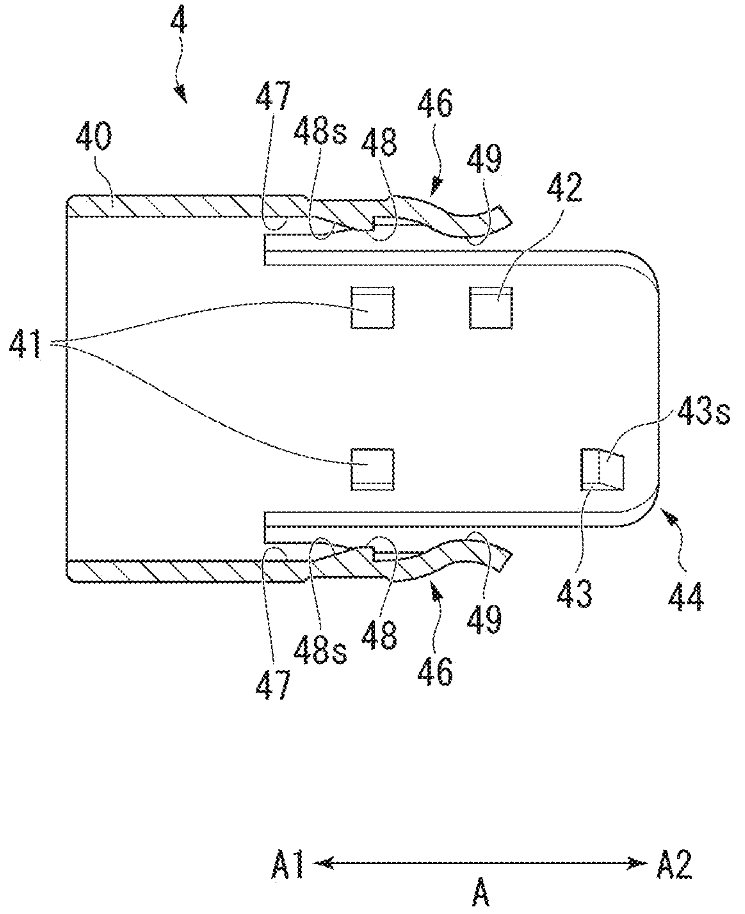
FIG. 6 illustrates an example of a cross-sectional view of the same coupler FIG. 4.

FIG. 6 illustrates an example cross-sectional view of the coupler 4.

Each of the pair of retention arms 44 can include a first protrusion 41 extending in the lateral direction (for example, inward in the radial direction R) from an inner peripheral surface 45 of each of the pair of retention arms 44 (that is, the surface of the retention arm 44 facing the bushing 210 of the applicator 200 in the operation state), a second protrusion 42 extending in the lateral direction (for example, inward in the radial direction R) from the inner peripheral surface 45 toward the proximal side of the first protrusion 41, and a retention element 43 provided on the proximal side of the second protrusion 42.

Figure 7:
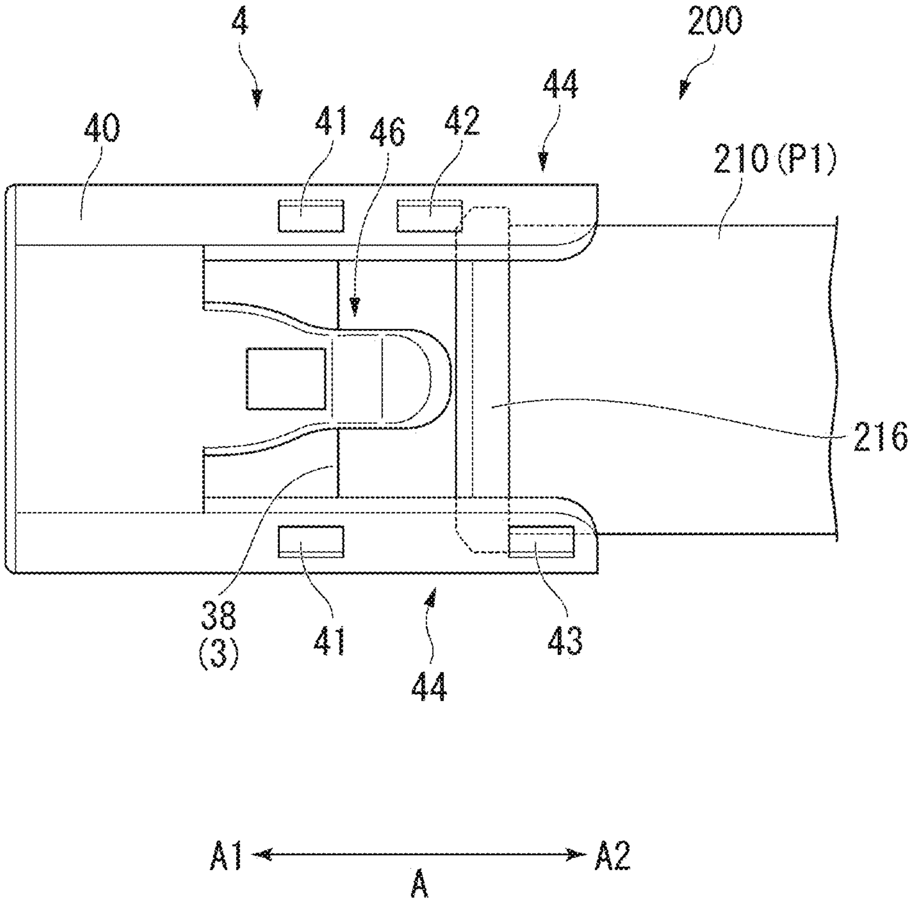
FIG. 7 illustrates an example diagram showing a bushing retained by a pair of retention arms of the same coupler of FIG. 4.
Figure 8:
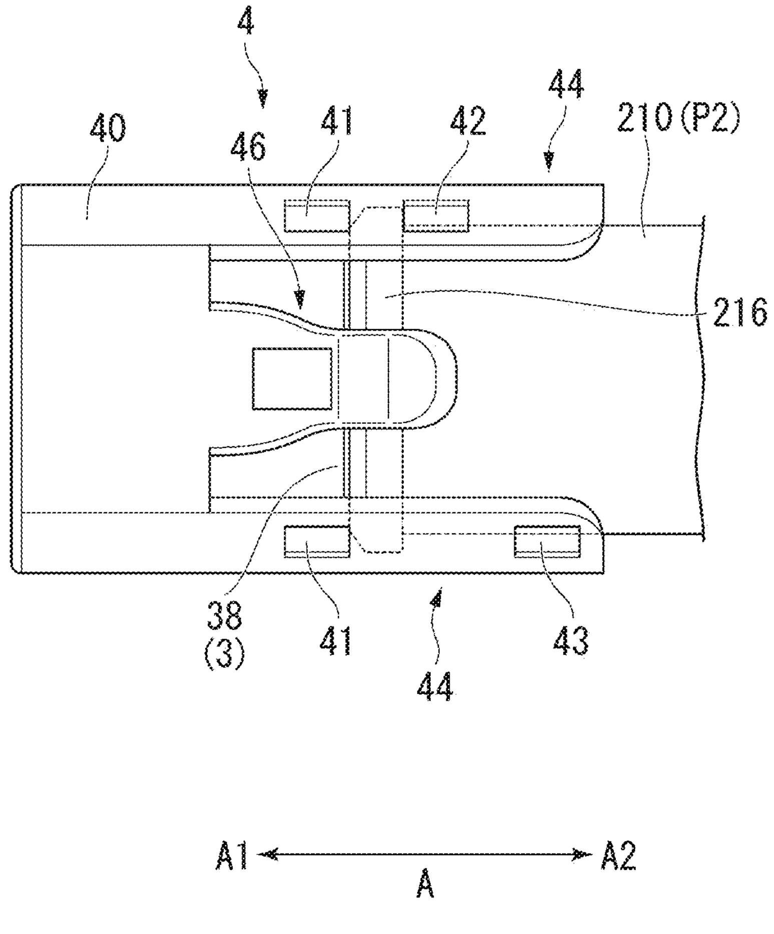
FIG. 8 illustrates an example diagram showing the same bushing of FIG. 7.

FIGS. 7 and 8 illustrate an example diagrams showing the bushing 210 retained by the pair of retention arms 44. The pair of retention arms 44 are arms that can retain the bushing 210 of the applicator 200. The bushing 210 can be retained at a first position P1 in which a projection 216 of the bushing 210 can be located between the second protrusion 42 and a retention element (third protrusion) 43 and a second position P2 in which the projection 216 of the bushing 210 can be located between the first protrusion 41 and the second protrusion 42.

The first protrusion 41 can have or be formed with a size and shape capable of engaging with a part of the proximal end 38 of the capsule 3. The first protrusion 41 can engage with a part of the proximal end 38 of the capsule 3 to restrict the coupler 4, sliding in the distal direction with respect to the capsule 3, from further moving in the distal direction.

The second protrusion 42 is a protrusion with which a distal end 212 of the bushing 210 retained at the first position P1 can engage. When loading the clip unit 100 into the applicator 200 or opening and closing the clip 2, the second protrusion 42 can engage with the projection 216 of the bushing 210 to restrict the bushing 210 from further moving in the distal direction from the first position P1. However, the depth of the second protrusion 42 (that is, the distance in which the second protrusion 42 extends from the inner peripheral surface 45) can be set to allow the second protrusion 42 to move in the proximal direction beyond the distal end 212 of the bushing 210 when a predetermined compressing force is applied to the coupler 4 during the deployment of the clip unit 100 as will be described later in detail. That is, the second protrusion 42 can have or be formed with a size and shape that determines the deployment force of the clip unit 100. Further, the second protrusion 42 can function as the retention element of the coupler 4 and can remain engaged with the bushing 210 after the coupler 4 is separated from the capsule 3.

The retention element (third protrusion) 43 is a protrusion which can extend from the inner peripheral surface 45 in the lateral direction (for example, inward in the radial direction R). When the clip unit 100 is loaded into the applicator 200 and the bushing 210 is retained at the first position P1, the retention element 43 can engage with a part of the bushing 210. The retention element 43 can have or be formed with a shape to facilitate the insertion of a part of the bushing 210 in the distal direction beyond the retention element 43. Specifically, the retention element 43 can include an inclined surface 43*s* that is tapered toward the proximal end of the retention element 43.

Figure 9:
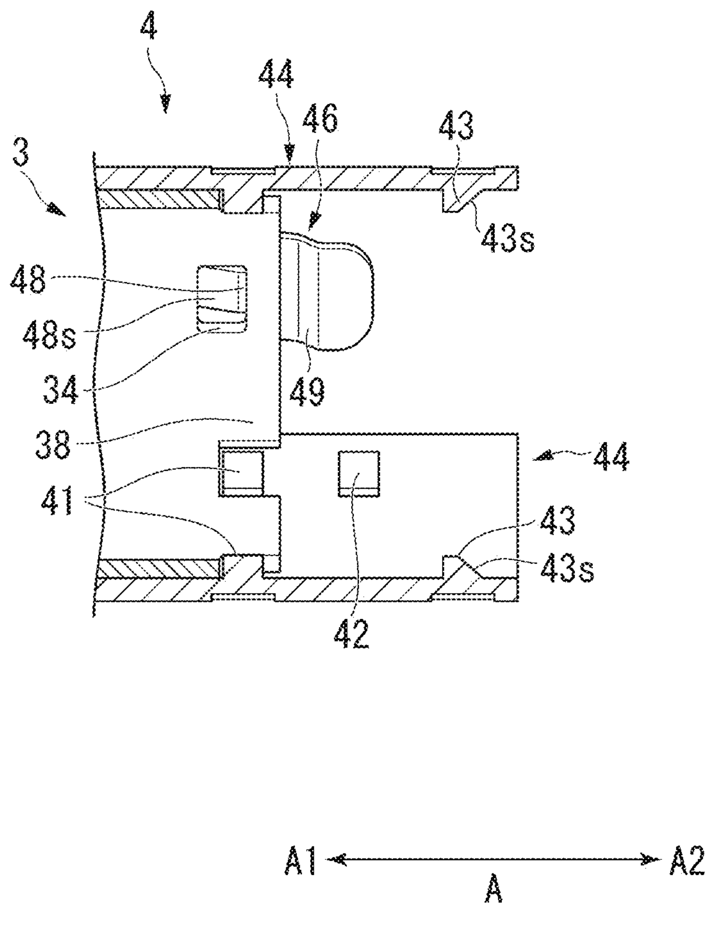
FIG. 9 illustrates an example cross-sectional view of the same coupler of FIG. 4 connected to a capsule.

FIG. 9 illustrates an example cross-sectional view of the coupler 4 connected to the capsule 3.

Each of the pair of deployment arms 46 can include an engagement element 48 that extends in the lateral direction (for example, inward in the radial direction R) from an inner surface 47 of each of the pair of deployment arms 46 (that is, the surface of the deployment arm 46 facing the bushing 210 in the operation state). When the coupler 4 is connected to the capsule 3 before the clip unit 100 is loaded into the applicator 200, the coupler 4 can move on the proximal end 38 of the capsule 3 in the distal direction until the further movement of the coupler 4 in the distal direction with respect to the capsule 3 is restricted. Specifically, the coupler 4 can move in the distal direction until the engagement element 48 snaps into one opening 34 corresponding to the capsule 3 and the first protrusion 41 engages with the capsule 3.

The engagement element 48 can include an inclined surface 48*s* that is tapered toward the distal end of the engagement element 48. When the coupler 4 is assembled to the capsule 3, the inclined surface 48*s* can facilitate the movement of the coupler 4 along the capsule 3 in the distal direction. When the coupler 4 is assembled to the capsule 3 as shown in FIG. 9, the inclined surface 48*s* of the engagement element 48 can restrict the movement of the coupler 4 in the proximal direction with respect to the capsule 3 and the first protrusion 41 can restrict the movement of the coupler 4 in the distal direction with respect to the capsule 3.

Each of the pair of deployment arms 46 can include a curved portion 49 provided on the proximal side of the engagement element 48. The curved portion 49 can be curved inward toward the longitudinal axis of the coupler 4 so that the distance between the curved portions 49 of the pair of deployment arms 46 becomes smaller than the distance between the remaining portions of the pair of deployment arms 46. For example, the curvature radius of the curved portion 49 can be smaller than the curvature radius of the remaining portion of the coupler 4. Thus, as will be described later in detail, when the curved portion 49 moves on a part of the bushing 210 in the proximal direction, the deployment arm 46 can deflect outward in the radial direction R so that the engagement element 48 is disengaged from the opening 34 of the capsule 3.

Although the pair of deployment arms 46 are shown and described as including the curved portion 49, the pair of deployment arms 46 may include other structures or elements for engaging the bushing 210 to cause outward deflection or deformation of the pair of deployment arms 46. The force required to deflect or deform the pair of deployment arms 46 can be controlled by adjusting the length and/or width of the deployment arms 46 or the distance between the curved portions 49. The depth of the engagement element 48 (that is, the distance that the engagement element 48 extends from the inner surface 47) can also be adjusted to increase or decrease the retention force of the coupler 4 on the capsule 3.

Figure 10:
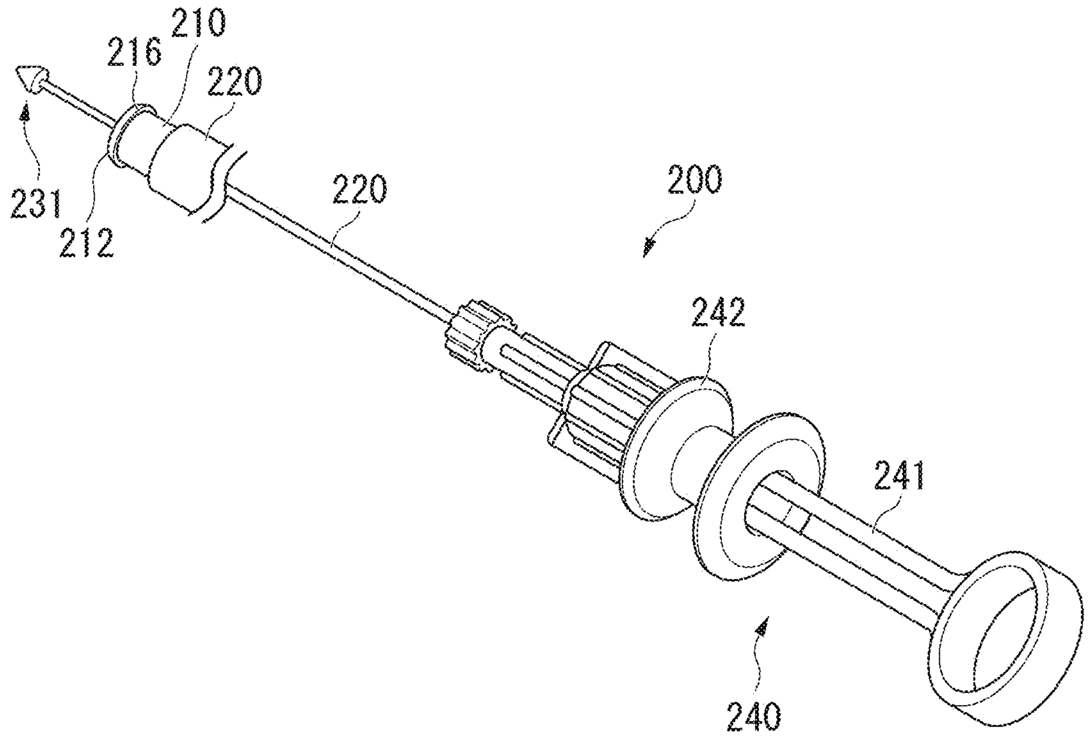
FIG. 10 illustrates an example of a perspective view of the same applicator of FIG. 2.

FIG. 10 illustrates an example perspective view of the applicator 200.

The applicator (clip introducing device) 200 can include a sheath 220, an operating wire 230, and an operating section 240. For example, the applicator 200 can inserted into a treatment tool insertion channel of an endoscope and used in combination with the endoscope. Therefore, the sheath 220 can be formed to be longer than the length of the treatment instrument insertion channel of the endoscope.

The sheath (elongated flexible member) 220 can be made flexible and curved to match the curvature of the insertion section of the endoscope. The sheath 220 can extend from the proximal end connected to the operating section (handle portion) 240 that remains outside the body while clipping target tissue to the distal end including the bushing 210 connecting the applicator 200 to the clip unit 100.

The operating wire (power transmission section) 230 can include a connection member (control member) 231 that is connected to the clip unit 1 and a wire 232 that can operate the connection member 231. The wire 232 can be inserted through the sheath 220 from the proximal end connected to the operating section (handle portion) 240 to the enlarged distal end 236.

The connection member 231 can include an enlarged distal end (arrowhead hook portion) 236. The enlarged distal end 236 can be formed into a generally conical shape that engages with the clip unit 1.

The wire 232 can be inserted through the sheath 220 so as to be able to advance and retract. The distal end of the wire 232 can be fixed to the base end of the connection member 231 by, for example, welding.

The operating section 240 can include an operating section main body 241 and a slider 242. The slider 242 can be attached so as to be able to advance and retract in the longitudinal axis direction of the operating section main body 241, and the base end of the wire 232 can be attached to the slider 242. As the slider 242 advances and retracts along the operating section main body 241, the wire 232 can advance and retract with respect to the sheath 220 and the enlarged distal end 236 can advance and retract. The operating section (handle portion) 240 can include an actuator to control the movement of the clip unit 100 after the clip unit 100 is loaded into the applicator 200.

The bushing 210 can be connected to the distal end of the sheath 220 and can be formed in a substantially cylindrical shape. The bushing 210 can be connected to the clip unit 100 via the coupler 4 assembled to the clip unit 100. The bushing 210 can include a channel 214 extending from the proximal end 211 to the distal end 212 and extending through the bushing 210. When the bushing 210 is connected to the clip unit 100 via the coupler 4, the channel 214 of the bushing 210 can be substantially connected to the channel 32 of the capsule 3.

The distal end 212 of the bushing 210 can include the projection 216. The projection 216 can extend outward in the radial direction R from an outer surface 215 along the distal end 212. The projection 216 can be provided on the entire circumference of the bushing 210 along the circumferential direction C. The distal end 218 of the projection 216 can be tapered to facilitate the insertion of the projection 216 in the distal direction beyond the retention element 43. A proximal end 219 of the projection 216 can be configured to engage with the retention element 43.

As described above, the clip unit 100 can be loaded into the applicator 200 by moving the projection 216 in the distal direction beyond the retention element 43 to dispose the bushing 210 at the first position P1. The projection 216 of the bushing 210 disposed at the first position P1 can be received between the second protrusion 42 and the retention element 43. When using the clip unit 100, for example, when opening and closing the pair of clip arms 21, the projection 216 can be retained between the second protrusion 42 and the retention element 43.

Figure 11:
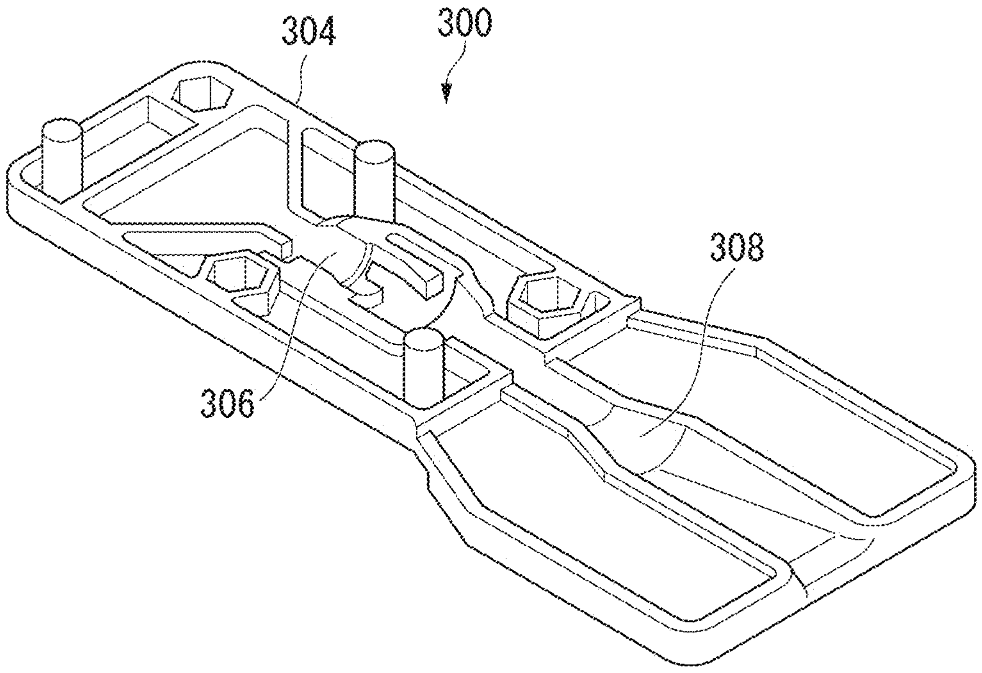
FIG. 11 illustrates an example diagram showing a part of the same cartridge.

FIG. 11 illustrates an example diagram showing a part of the cartridge 300.

Before the loading into the applicator 200, the clip unit 100 can be accommodated in the cartridge 300 configured to easily load the clip unit 100 into the applicator 200. The cartridge 300 can be configured as a storage container, which can include a base portion 304 and a lid and a space 306 having a size and shape for accommodating the clip unit 100 is provided therein.

Although FIG. 8 shows only the base portion 304 of the cartridge 300, the corresponding lid can be connected to the base portion 304 to completely surround the clip unit 100. In this embodiment, the clip unit 100 can be accommodated in the cartridge 300 in an open state together with the coupler 4 assembled to the capsule 3 in advance. As will be described in more detail later, the slot 308 into which the distal portion of the applicator 200 is inserted to be connected to the clip unit 100 can extend from the space 306 in the proximal direction.

Next, the operation and effect of the clip unit 100 will be described with reference to FIGS. 12 to 15.

The clip unit 100 loaded into the applicator 200 can be accommodated in the cartridge 300. The coupler 4 can be assembled, attached, or the like, onto the proximal end 38 of the capsule 3 so that the engagement element 48 of each of the pair of deployment arms 46 can be received into the corresponding opening 34 of the capsule 3 and the first protrusion 41 engages with a part of the capsule 3.

In order to load the clip unit 100 into the applicator 200, the distal portion of the applicator 200 including the bushing 210 can be inserted into the space 306 through the slot 308 of the cartridge 300 accommodating the clip unit 100 with the coupler 4 assembled thereto.

Figure 12:
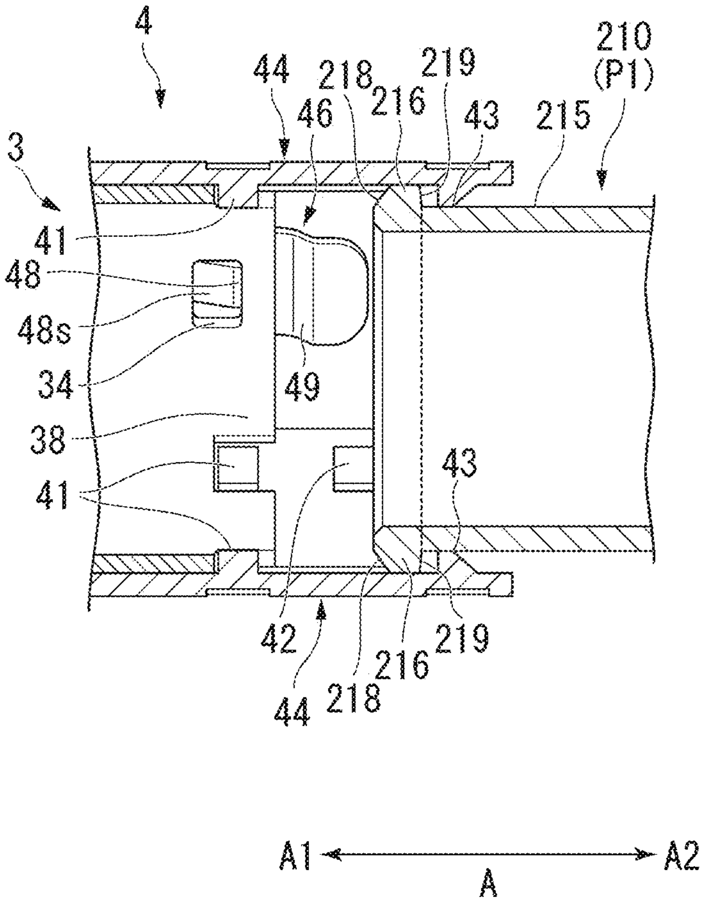
FIG. 12 illustrates an example cross-sectional view of the same bushing disposed at a first position.
Figure 13:
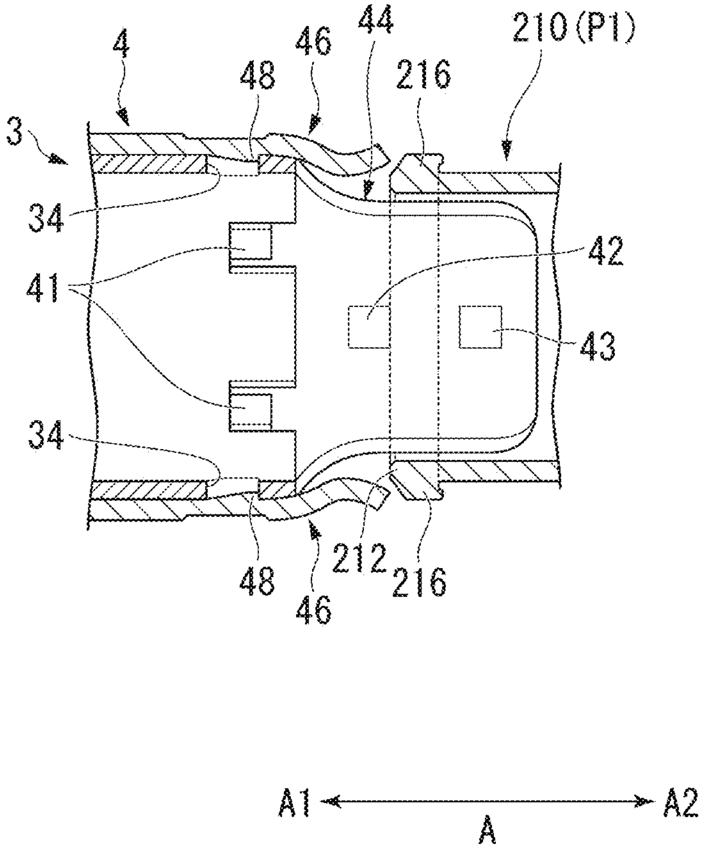
FIG. 13 illustrates an example cross-sectional view of the same bushing disposed at the first position.

FIGS. 12 and 13 illustrate example cross-sectional views of the bushing 210 disposed at the first position P1.

In this embodiment, the distal end 212 of the bushing 210 can move in the distal direction between the pair of retention arms 44 of the coupler 4 so that the projection 216 can move in the distal direction beyond the retention element 43 to be received between the second protrusion 42 and the retention element 43. When the bushing 210 is disposed at the first position P1 and is connected to the clip unit 100 via the coupler 4, the connection member 231 can be moved in the distal direction with respect to the bushing 210 and can be connected to the pair of clip arms 21 via the yoke 22. Specifically, the enlarged distal end 236 of the connection member 231 can be inserted through the slot 308 and is inserted into the cavity 20 of the yoke 22.

Furthermore, the connection member 231 can be connected to the yoke 22 before the bushing 210 is connected to the coupler 4. After the connection member 231 is connected to the yoke 22, the capsule 3 can move in the proximal direction with respect to the bushing 210 in accordance with the movement of the connection member 231 in the proximal direction and the coupler 4 moves on the distal end 212 of the bushing 210 in the proximal direction to engage with the projection 216.

When both the connection member 231 and the bushing 210 are connected to the clip unit 100, the loading of the clip unit 100 into the applicator 200 can be completed and the clip unit 100 can be inserted through the slot 308 to be withdrawn from the cartridge 300 in the proximal direction.

After the clip unit 100 is loaded into the applicator 200, the clip unit 100 can be inserted into the body in a closed state, for example, through the channel of the endoscope to a site adjacent to the target tissue. When the clip unit 100 reaches the target tissue, the clip unit 100 can move toward an open state in order to receive the target tissue between both distal ends 23 of the pair of clip arms 21. The clip unit 100 can move between an open state and a closed state, if necessary, until the target tissue is clipped between the pair of clip arms 21. When the clip unit 100 becomes a closed state that clips the target tissue, if necessary, the connection member 231 can be moved in the proximal direction with respect to the capsule 3 until the locking elements of the pair of clip arms 21 engage with the corresponding locking structure of the capsule 3. As a result, the pair of clip arms 21 can be locked to the capsule 3 in a closed state.

Figure 14:
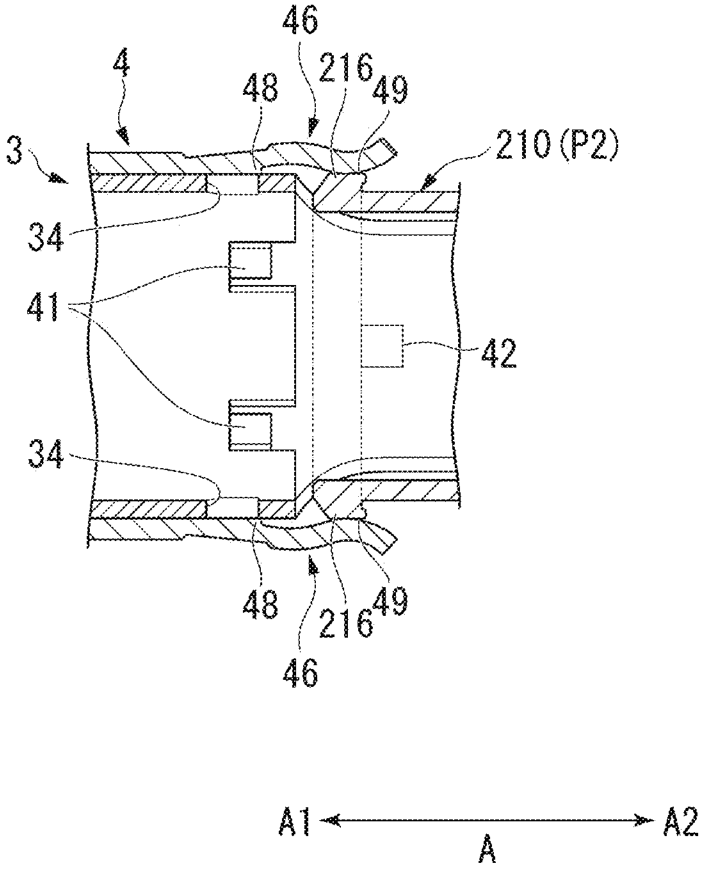
FIG. 14 illustrates an example cross-sectional view of the same bushing disposed at a second position.

FIG. 14 illustrates an example cross-sectional view of the bushing 210 disposed at the second position P2.

In order to release the clip unit 100 from the applicator 200, the coupler 4 can be pulled in the proximal direction with respect to the bushing 210. When the connection member 231 is pulled further in the proximal direction until the compressive load on the coupler 4 exceeds a predetermined threshold, the second protrusion 42 can pass in the proximal direction beyond the projection 216 of the bushing 210 and the curved portions 49 of the pair of deployment arms 46 slide in the proximal direction beyond the projection 216. The projection 216 can move in the distal direction beyond the second protrusion 42 and the bushing 210 is disposed at the second position P2.

When the curved portion 49 moves on the projection 216 in the proximal direction, the curved portion 49 can engage with the projection 216 and the pair of deployment arms 46 deflect outward in the radial direction R. Accordingly, the engagement elements 48 of the pair of deployment arms 46 can be disengaged from the opening 34 of the capsule 3.

Figure 15:
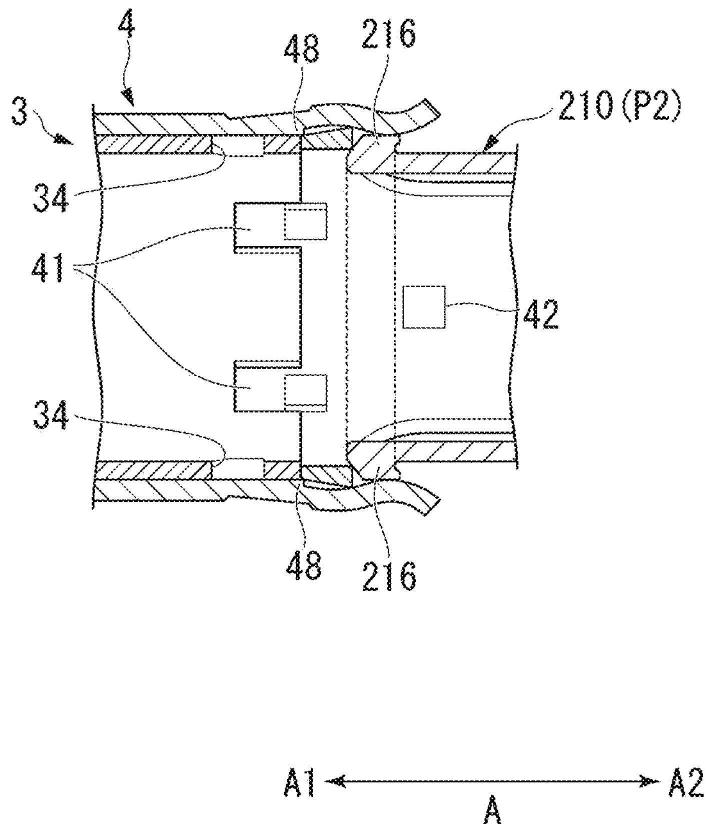
FIG. 15 illustrates an example cross-sectional view of the same coupler disengaged from the same capsule.

FIG. 15 illustrates an example cross-sectional view of the coupler 4 disengaged from the capsule 3.

When the bushing 210 is disposed at the second position P2, the coupler 4 can engage with and connect to the bushing 210. On the other hand, the coupler 4 can be disengaged from the capsule 3. The user can continue to apply a proximal force to the connection member 231 until the yoke 22 breaks, deforms, or separates so that the clip unit 100 is disengaged from the connection member 231. Thus, the applicator 200 connected to the coupler 4 can be detached from the clip 2 and the capsule 3 so that only the clip 2 and the capsule 3 are left in place at a predetermined site with the target tissue clipped.

Next, the entire applicator 200 including the connection member 231, the coupler 4, and the proximal portion 28 of the yoke 22 can be withdrawn in the proximal direction from the body to leave the clip 2 and the capsule 3 clipped on the target tissue. When the clip 2 and the capsule 3 are deployed, the coupler 4 is detached from the capsule 3 and can be detached from the body together with the applicator 200. The coupler 4 can be attached to the bushing 210 even after being detached from the capsule 3. Therefore, when the clip 2 and the capsule 3 are deployed, no falling parts are left inside the body.

The user can remove the applicator 200 connected to the coupler 4 from the channel of the endoscope. As shown in FIG. 5, in the cross-section along the radial direction R, the pair of deployment arms 46 can be arranged on the inside of the largest circumscribed circle C4 of the coupler 4. Therefore, when the applicator 200 connected to the coupler 4 is removed from the channel of the endoscope, the coupler 4 can be less likely to come into contact with the inner peripheral surface of the channel of the endoscope, and can be easily passed through the channel of the endoscope.

When the clip 2 is deployed to the target site within the body, the user can reload the applicator 200 with a new clip unit 100. The coupler 4 is detached from the bushing 210 by the user before loading a new clip unit 100 into the same applicator 200. The user can load a new clip unit 100 into the same applicator 200 and use the same applicator 200 to deliver the new clip unit 100 to a second portion of the target tissue.

Since a new clip unit 100 can be loaded into the applicator 200 in the same manner as described above, if necessary, the clip system 500 can be used to clip the second portion of the tissue. This process can be repeated as needed or as many times as necessary using the same applicator 200.

According to the clip system 500 of this embodiment, the coupler 4 that connects the clip unit 100 and the applicator 200 can be less likely to come into contact with the inner peripheral surface of the channel of the endoscope, and can be easily passed through the channel of the endoscope.

Although the first embodiment of the present disclosure has been described above in detail with reference to the drawings, the specific configuration is not limited to this embodiment, and design changes can be made within the scope of the present disclosure. Further, the components shown in the embodiments and modified examples can be configured by appropriately combining them.

Modified Example 1-1

Figure 16:
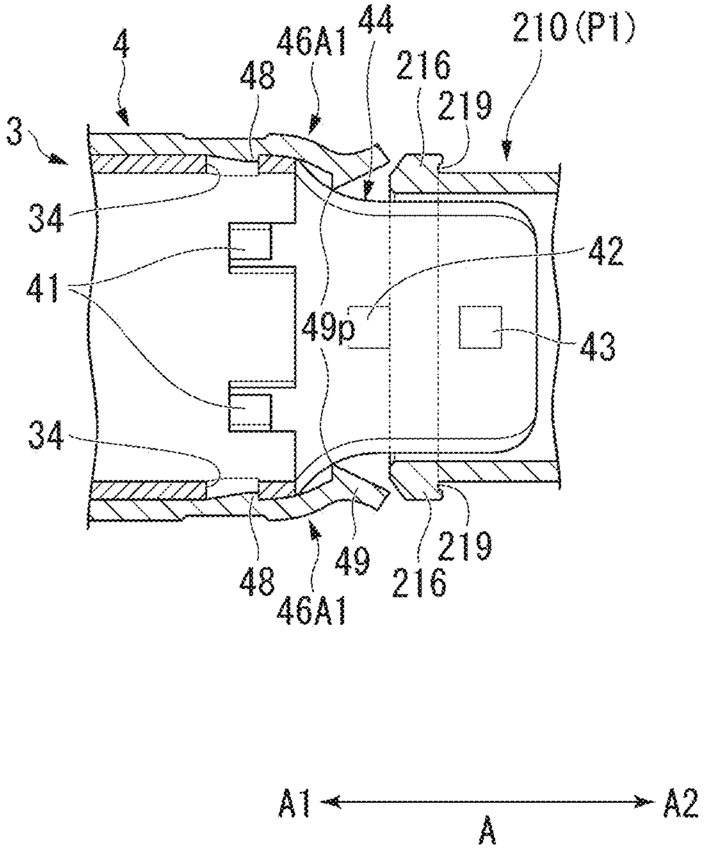
FIG. 16 illustrates an example diagram showing a modified example of a pair of deployment arms of the same coupler.
Figure 17:
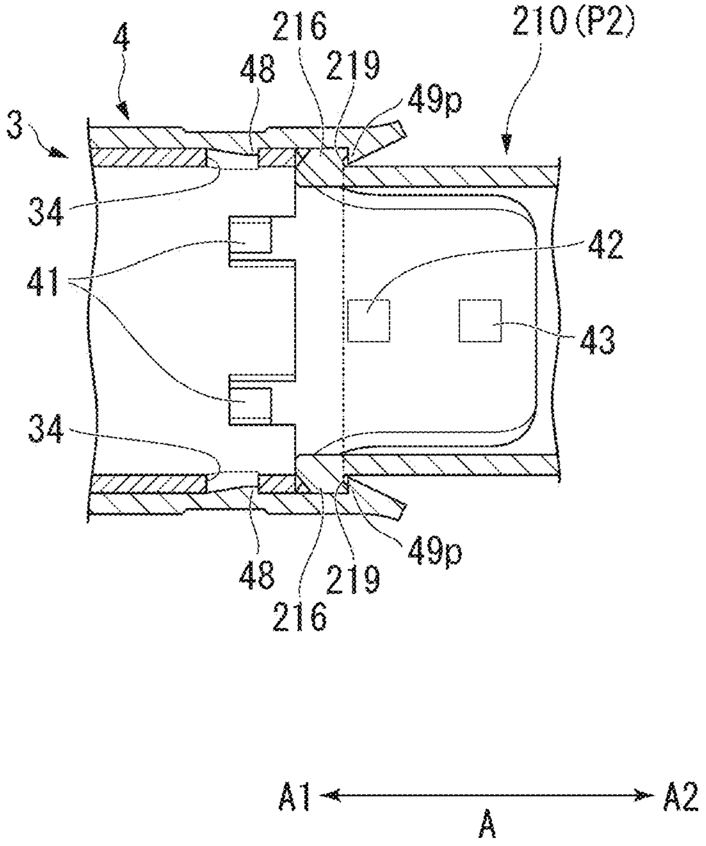
FIG. 17 illustrates an example diagram showing the same modified example of the same pair of deployment arms.

FIGS. 16 and 17 illustrate example diagrams showing a pair of deployment arms 46A1 which is a modified example of the pair of deployment arms 46. Each of the curved portions 49 of the pair of deployment arms 46A1 can include a protrusion 49*p* that protrudes toward the distal side on the inner peripheral surface 45. As shown in FIG. 17, when the bushing 210 is disposed at the second position P2, the protrusion 49*p* can engage with the proximal end 219 of the projection 216. Therefore, the coupler 4 can be less likely to fall off from the bushing 210 disposed at the second position P2.

Modified Example 1-2

Figure 18:
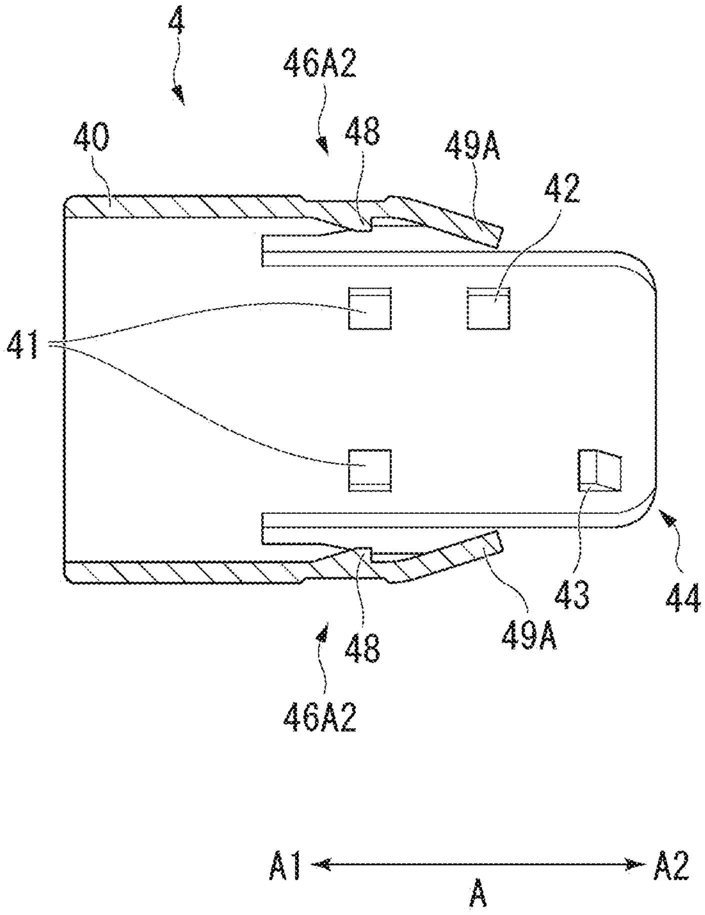
FIG. 18 illustrates an example diagram showing another modified example of the same pair of deployment arms.

FIG. 18 illustrates an example diagram showing a pair of deployment arms 46A2 which is a modified example of the pair of deployment arms 46. The pair of deployment arms 46A2 can include a curved portion 49A which is a modified example of the curved portion 49. The curved portion 49A can be inclined inward in the radial direction R with respect to the longitudinal direction A. The distance between the proximal ends of the curved portions 49A of the pair of deployment arms 46A2 can be smaller than the distance between the remaining portions of the pair of deployment arms 46A2. For example, the angle at which the curved portion 49A is inclined with respect to the longitudinal direction A can larger than 0° and equal to or smaller than 90°. Since the proximal ends of the pair of deployment arms 46A2 face inward in the radial direction R and are less likely to come into contact with the inner peripheral surface of the channel of the endoscope, the coupler 4 can be easily passed through the channel of the endoscope.

Modified Example 1-3

Figure 19:
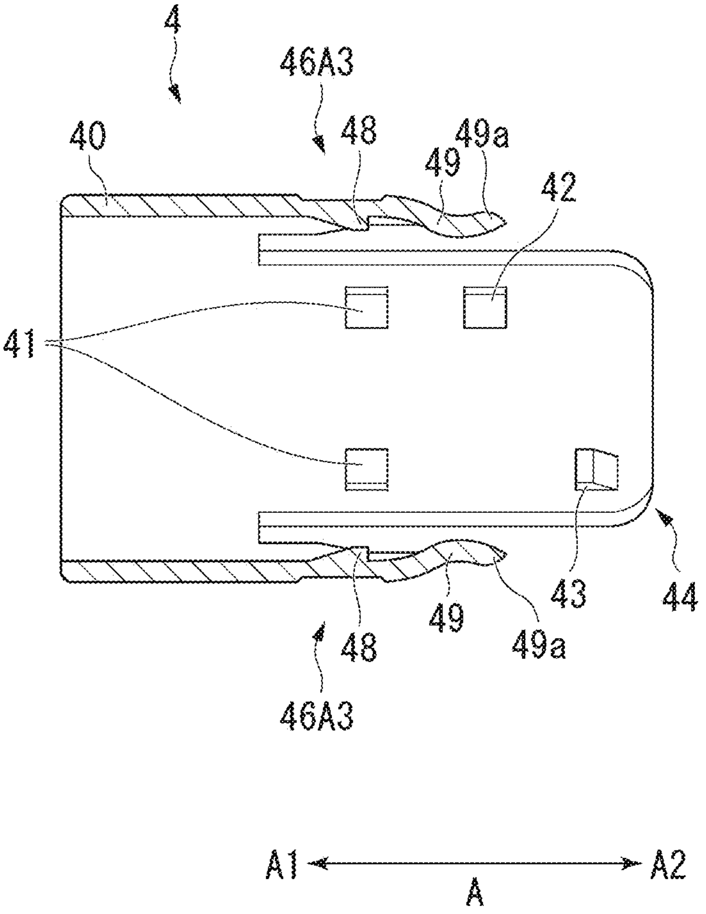
FIG. 19 illustrates an example diagram showing another modified example of the same pair of deployment arms.

FIG. 19 illustrates an example diagram showing a pair of deployment arms 46A3 which is a modified example of the pair of deployment arms 46. The pair of deployment arms 46A3 can include a rounded portion 49*a* rounded on the outer peripheral portion of the proximal end. Since the outer peripheral portions of the proximal ends of the pair of deployment arms 46A3 are rounded and are less likely to come into contact with the inner peripheral surface of the channel of the endoscope, the coupler 4 can be easily passed through the channel of the endoscope.

Second Embodiment

A second embodiment of the present disclosure will be described with reference to FIGS. 20 to 22. In the following description, components that are common to those already described will be indicated by the same reference numerals and redundant description will be omitted.

Figure 20:
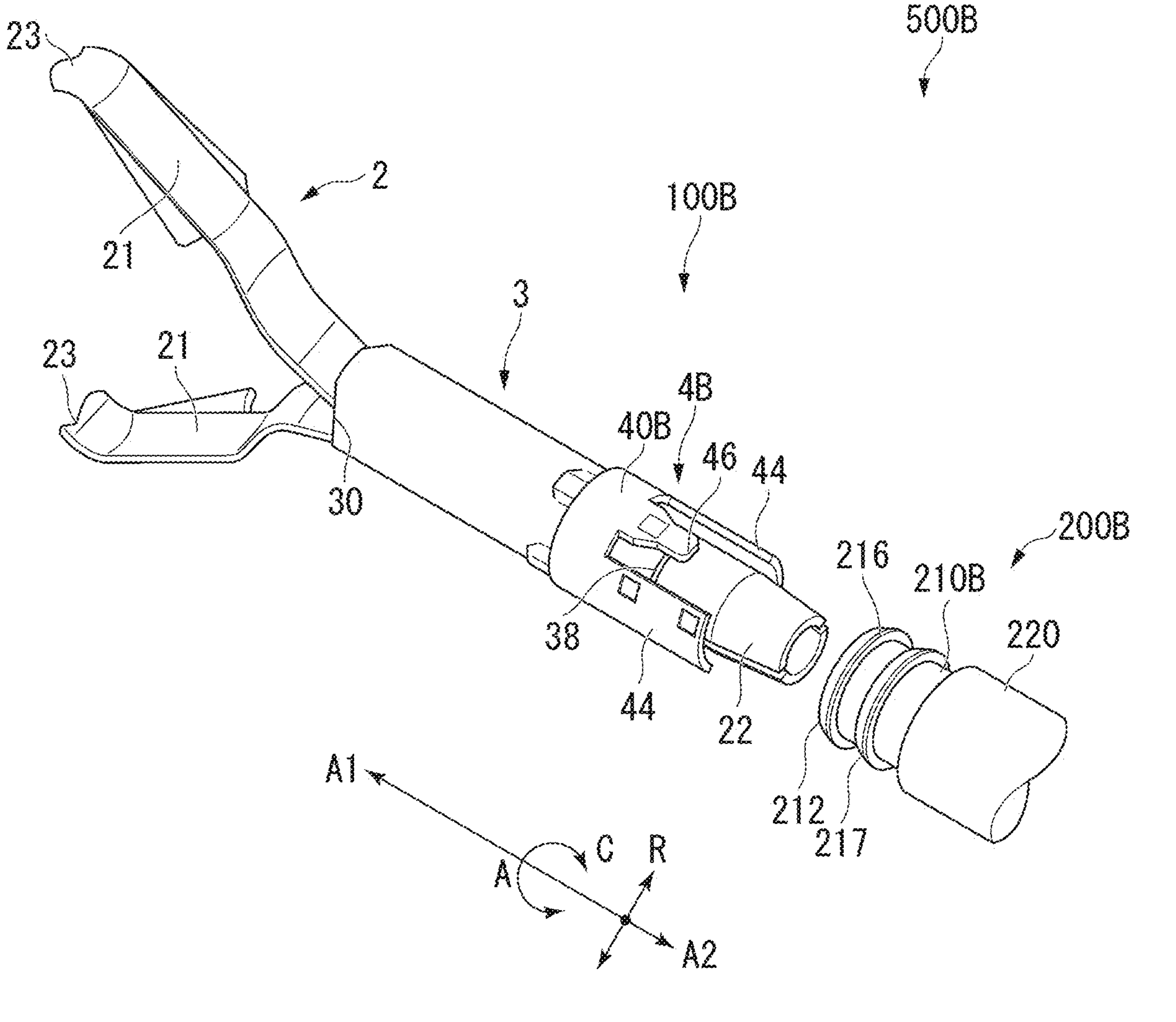
FIG. 20 illustrates an example diagram showing a part of a clip system according to a second embodiment of the present disclosure.

FIG. 20 illustrates an example diagram showing a part of a clip system 500B.

The clip system 500B according to this embodiment can include a clip unit 100B, an applicator 200B, and the cartridge 300.

The clip unit 100B can include the clip 2, the capsule 3, and a coupler 4B.

The coupler 4B can be connected to the proximal end 38 of the capsule 3 of the clip unit 100B before the clip unit 100B is loaded into the applicator 200. The coupler 4B can include a distal portion 40B, the pair of retention arms 44, and the pair of deployment arms 46.

The distal portion 40B can be the same as the distal portion 40 of the first embodiment except that the cross-section along the radial direction R is approximately circular.

The applicator 200B includes a sheath 220B, the operating wire 230, and the operating section 240.

The sheath 220B can be made flexible and curved to match the curvature of the insertion section of the endoscope. The sheath 220B can extend from the proximal end connected to the operating section 240 that remains outside the body while clipping the target tissue to the distal end including a bushing 210B connecting the applicator 200B to the clip unit 100B.

The bushing 210B can be the same as the bushing 210 of the first embodiment except that a second projection 217 is provided on the proximal side of the projection 216 in addition to the projection (first projection) 216 provided at the distal end 212. The second projection 217 can be formed to have substantially the same shape as the projection 216.

Figure 21:
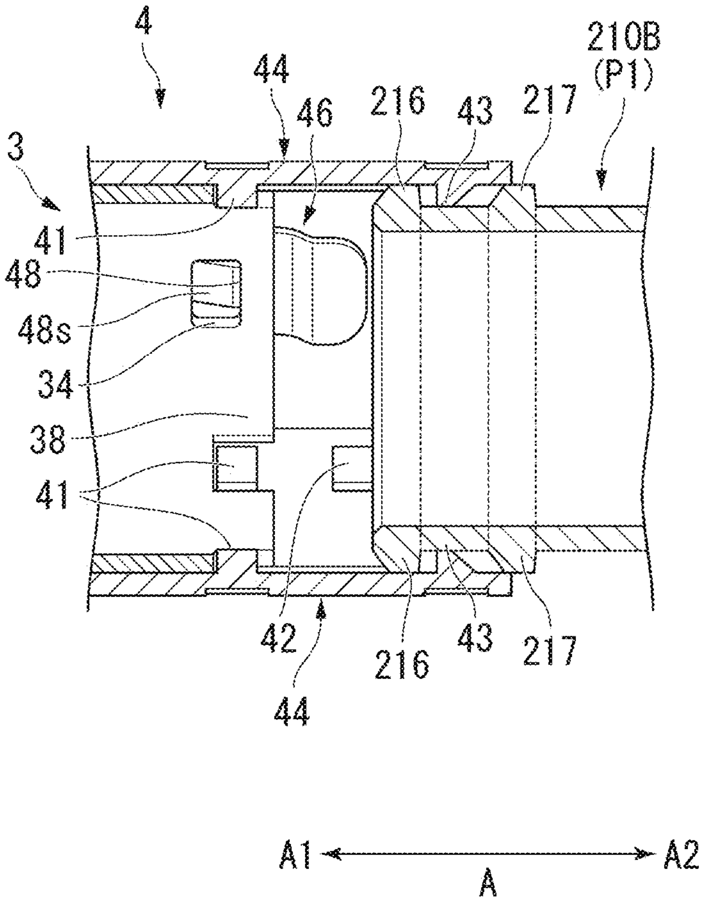
FIG. 21 illustrates an example cross-sectional view of a bushing disposed at a first position.

FIG. 21 illustrates an example cross-sectional view of the bushing 210B disposed at the first position P1.

When the bushing 210B is disposed at the first position P1, the second projection 217 can be disposed on more proximal side than a position of the retention element 43.

Figure 22:
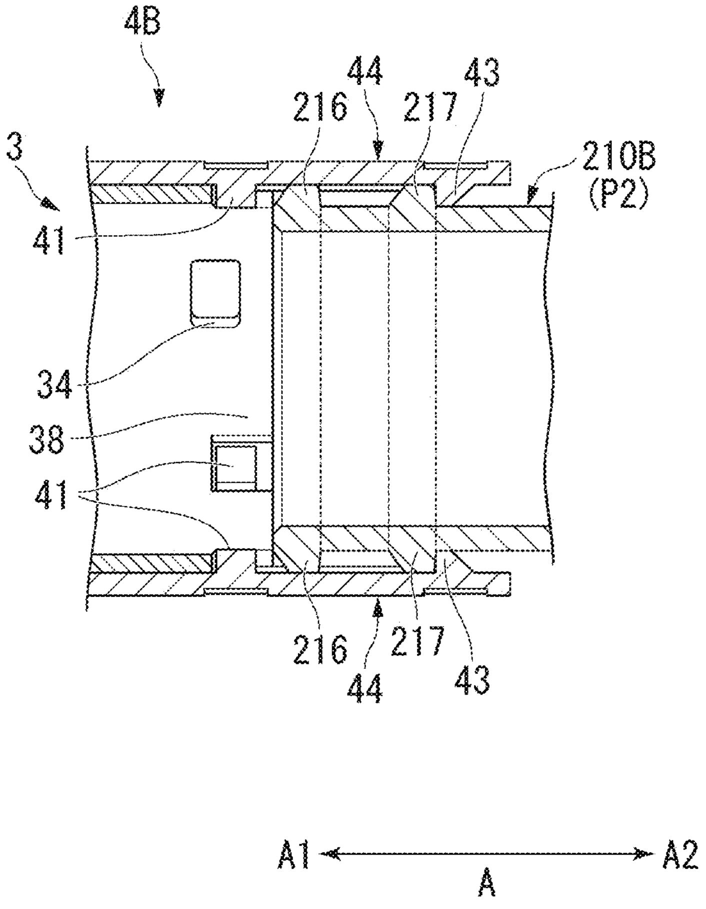
FIG. 22 illustrates an example cross-sectional view of the same bushing disposed at a second position.

FIG. 22 illustrates an example cross-sectional view of the bushing 210B disposed at the second position P2.

When the bushing 210B is disposed at the second position P2, the second projection 217 can be disposed between the second protrusion 42 and the retention element 43. With the bushing 210B disposed at the second position P2, the projection 216 and the second projection 217 can engage with the coupler 4. Therefore, when the applicator 200 connected to the coupler 4B is removed from the channel of the endoscope, the coupler 4B can be less likely to fall off from the applicator 200B.

According to the clip system 500B of this embodiment, the coupler 4B is less likely to fall off from the applicator 200B and can be easily passed through the channel of the endoscope.

Although the second embodiment of the present disclosure has been described above in detail with reference to the drawings, the specific configuration is not limited to this embodiment, and design changes can be made within the scope of the present disclosure. Furthermore, the components shown in the embodiments and modified examples can be configured by appropriately combining them.

Modified Example 2-1

Figure 23:
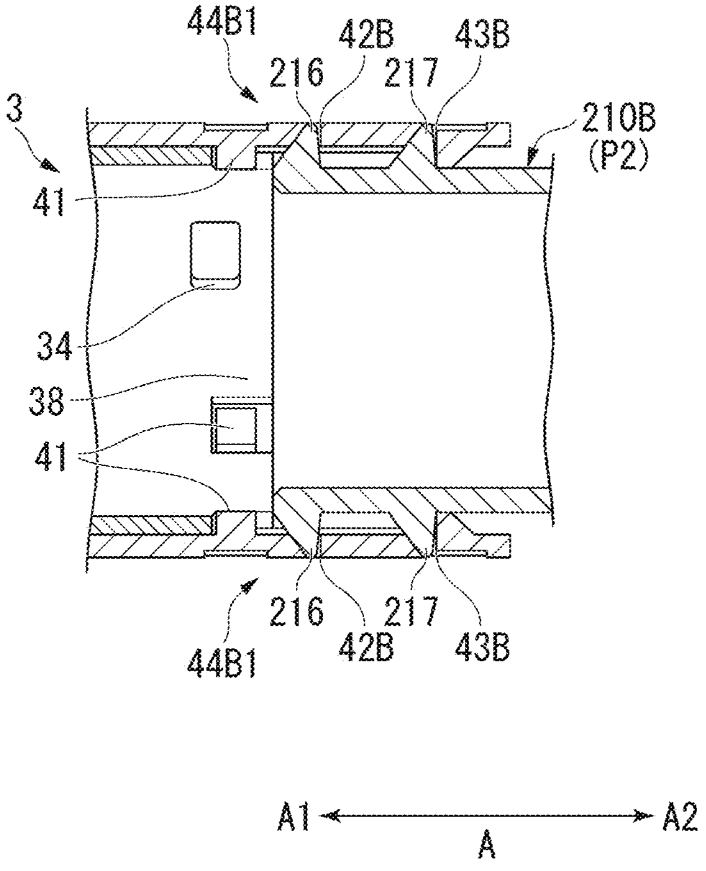
FIG. 23 illustrates an example diagram showing a modified example of a pair of retention arms.

FIG. 23 illustrates an example diagram showing a pair of retention arms 44B1 which is a modified example of the pair of retention arms 44. The pair of retention arms 44B1 can include a second concave portion 42B and a third concave portion 43B instead of the second protrusion 42 and the retention element 43. Since the second concave portion 42B and the third concave portion 43B can engage with the projection (first projection) 216 and the second projection 217, the pair of retention arms 44B1 can be connected to the bushing 210B. Furthermore, the second protrusion 42 and the retention element 43 can engage with the concave portions provided in the bushing 210B to be connected to the bushing 210B.

Modified Example 2-2

Figure 24:
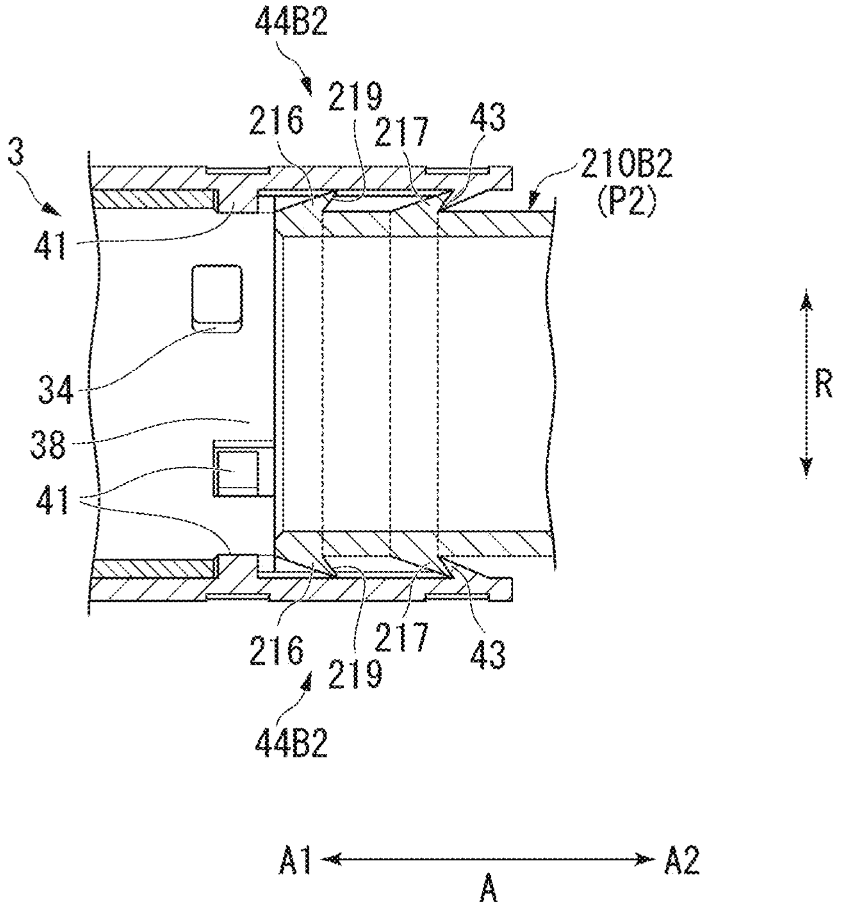
FIG. 24 illustrates an example diagram showing another modified example of the same pair of retention arms.

FIG. 24 illustrates an example diagram showing a pair of retention arms 44B2 which is a modified example of the pair of retention arms 44. The pair of retention arms 44B2 can be connected to a bushing 210B2 which is a modified example of the bushing 210B. The distal ends of the second protrusion 42 and the retention element 43 of the pair of retention arms 44B2 can be inclined surfaces which are inclined with respect to the longitudinal direction A and the normal direction faces outward in the radial direction R. For example, the angle at which the distal ends of the second protrusion 42 and the retention element 43 are inclined with respect to the longitudinal direction A can be larger than 0° and equal to or smaller than 45°. The proximal ends 219 of the first projection 216 and the second projection 217 in the bushing 210B2 can be inclined with respect to the longitudinal direction A to engage with the second protrusion 42 and the retention element 43 in the pair of retention arms 44B2 and the normal direction faces inward in the radial direction R. The pair of retention arms 44B2 can be connected to the bushing 210B2. Further, the pair of retention arms 44B2 and the bushing 210B2 can be connected in the radial direction R. As a result, the pair of retention arms 44B2 can be less likely to expand outward in the radial direction R.

Modified Example 2-3

Figure 25:
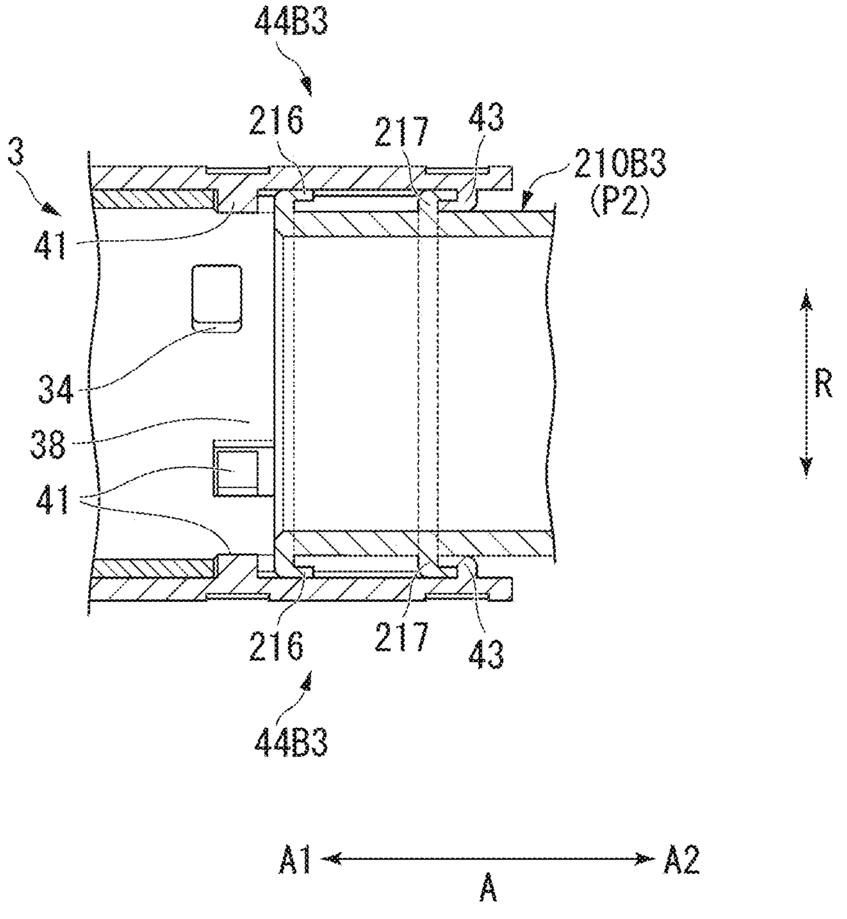
FIG. 25 illustrates an example diagram showing another modified example of the same pair of retention arms.

FIG. 25 illustrates an example diagram showing a pair of retention arms 44B3 which is a modified example of the pair of retention arms 44. The pair of retention arms 44B3 can be connected to a bushing 210B3 which is a modified example of the bushing 210B. The second protrusion 42 and the retention element 43 in the pair of retention arms 44B3 can be formed in an L-shaped hook shape. The first projection 216 and the second projection 217 in the bushing 210B3 can be formed in an L-shaped hook shape to engage with the second protrusion 42 and the retention element 43 in the pair of retention arms 44B3. The pair of retention arms 44B3 can be connected to the bushing 210B3. Further, the pair of retention arms 44B3 and the bushing 210B3 can be connected in the radial direction R. As a result, the pair of retention arms 44B3 can be less likely to expand outward in the radial direction R.

Modified Example 2-4

Figure 26:
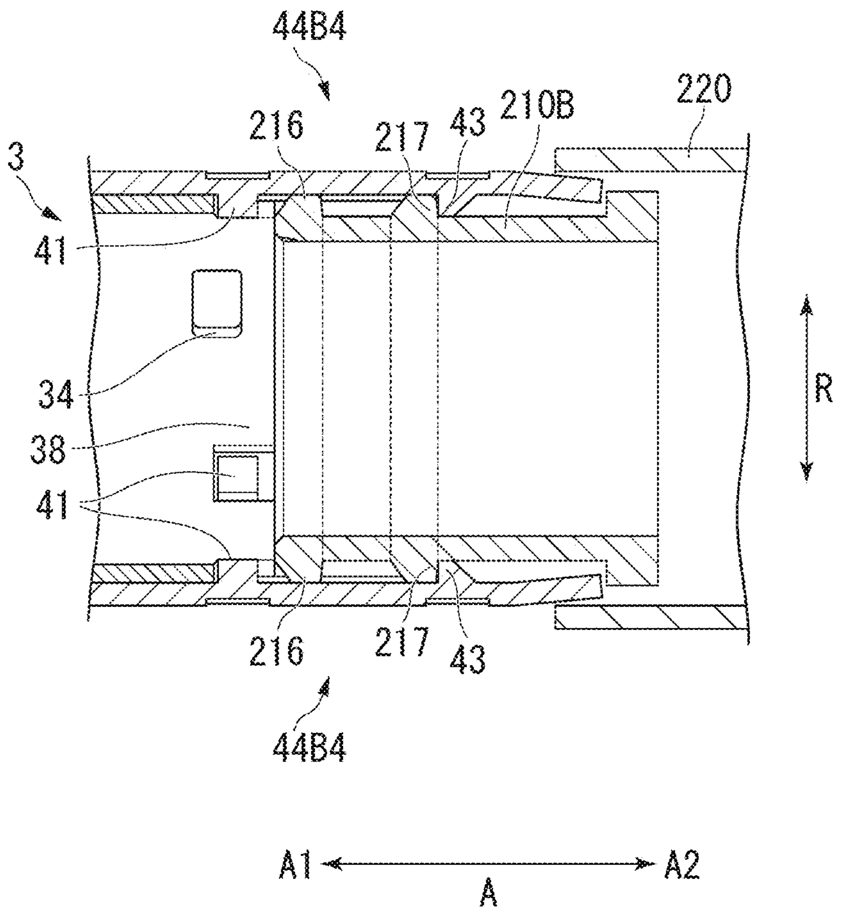
FIG. 26 illustrates an example diagram showing another modified example of the same pair of retention arms.

FIG. 26 illustrates an example diagram showing a pair of retention arms 44B4 which is a modified example of the pair of retention arms 44. The pair of retention arms 44B4 can be inclined inward in the radial direction R with respect to the longitudinal direction A and are reduced in diameter on the proximal side. For example, the angle at which the proximal side of the pair of retention arms 44B4 is inclined with respect to the longitudinal direction A is larger than 0° and equal to or smaller than 45°. Since the proximal ends of the pair of retention arms 44B4 are reduced in diameter, for example, the proximal ends are covered by the sheath 220 and can be less likely to come into contact with the inner peripheral surface of the channel of the endoscope.

Modified Example 2-4

Figure 27:
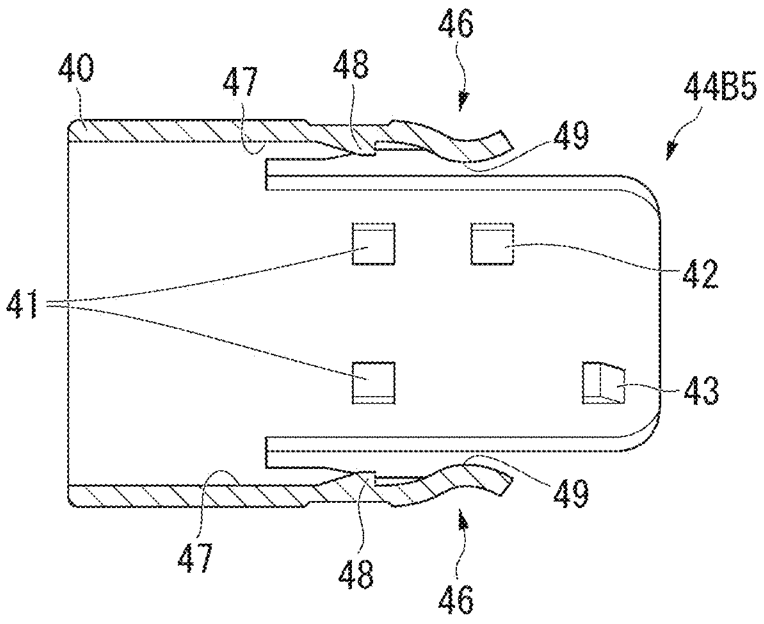
FIG. 27 illustrates an example diagram showing another modified example of the same pair of retention arms.
Figure 28:
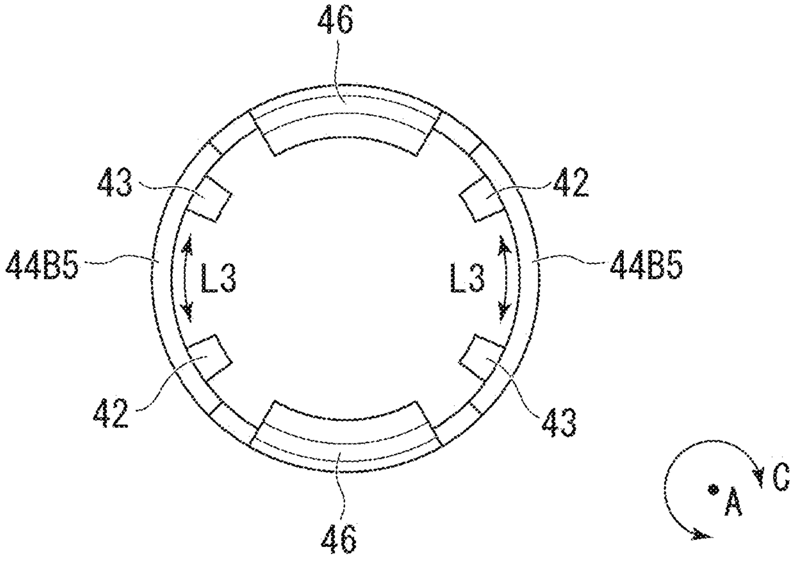
FIG. 28 illustrates an example diagram showing the same modified example of the same pair of retention arms.

FIGS. 27 and 28 illustrate example diagrams showing a pair of retention arms 44B5 which is a modified example of the pair of retention arms 44. In the pair of retention arms 44B5, the length L3 in the circumferential direction C between the protrusions (the first protrusion 41, the second protrusion 42, and the retention element 43) can be shorter compared to the pair of retention arms 44 of the first embodiment. The protrusions of the pair of retention arms 44B5 can be arranged relatively equally in the circumferential direction C compared to the pair of retention arms 44 of the first embodiment. Therefore, the pair of retention arms 44B5 connected to the bushing 210B can be made strong against bending loads from any direction in the radial direction R and can be less likely to fall off.

Third Embodiment

A third embodiment of the present disclosure are described with reference to FIGS. 29 to 34. In the following description, components that are common to those already described will be indicated by the same reference numerals and redundant description will be omitted.

Figure 29:
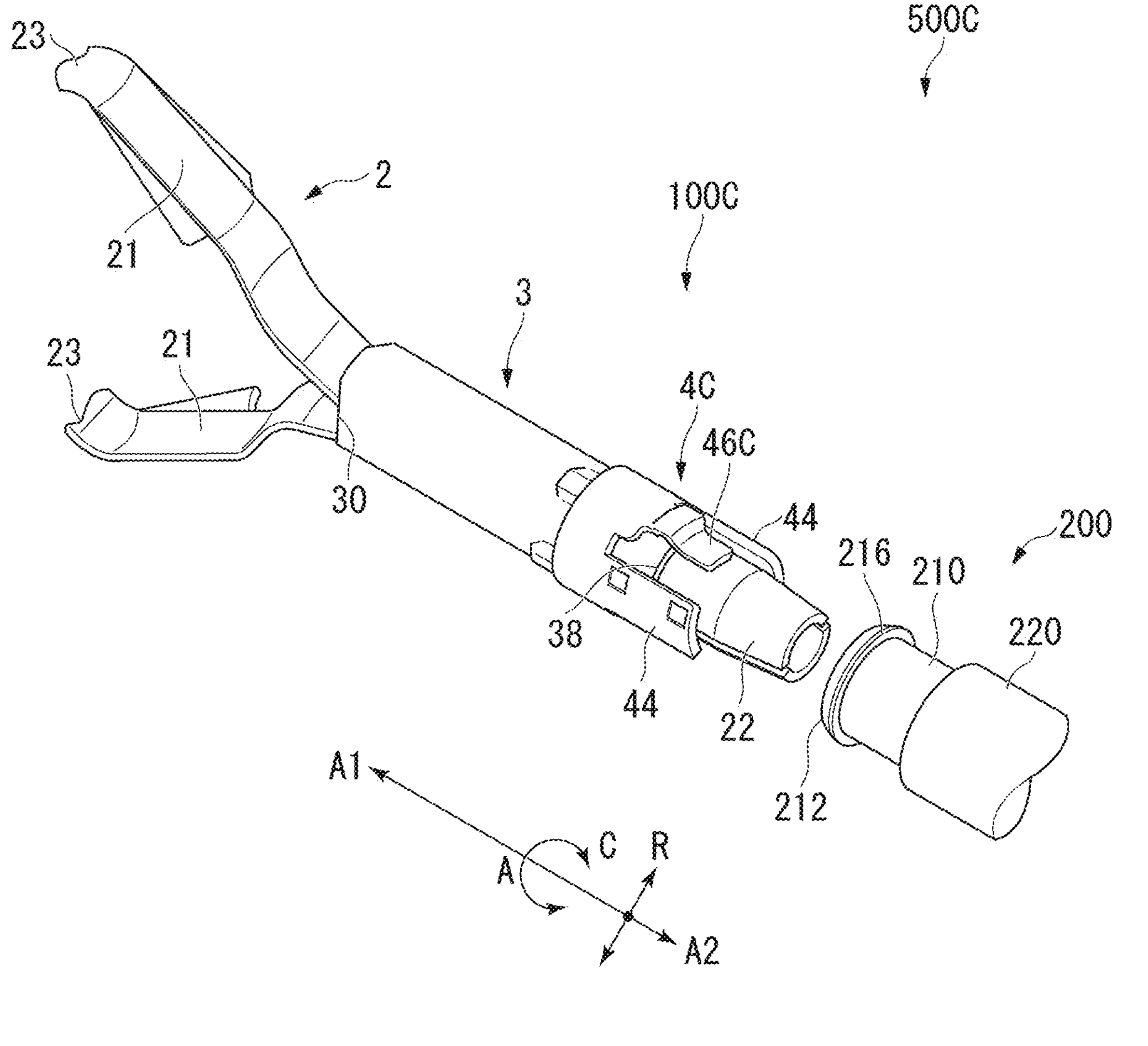
FIG. 29 illustrates an example diagram showing a part of a clip system according to a third embodiment of the present disclosure.
Figure 30:
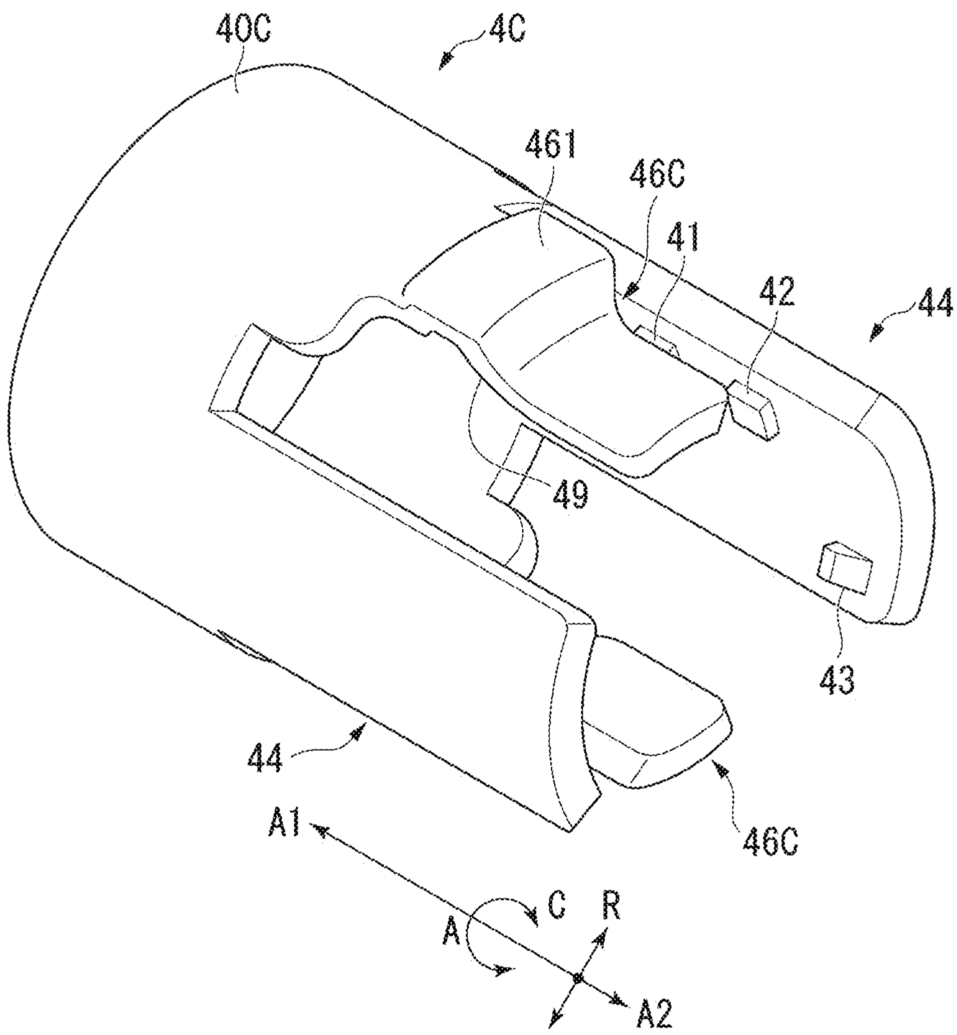
FIG. 30 illustrates an example perspective view of a coupler.

FIG. 29 illustrates an example diagram showing a part of the clip system 500C.

The clip system 500C according to this embodiment can include a clip unit 100C, the applicator 200, and the cartridge 300.

The clip unit 100C can include the clip 2, the capsule 3, and a coupler 4C.

FIG. 29 illustrates an example perspective view of the coupler 4C.

The coupler 4C can be connected to the proximal end 38 of the capsule 3 of the clip unit 100C before the clip unit 100C is loaded into the applicator 200. The coupler 4C can include a distal portion 40C, the pair of retention arms 44, and a pair of deployment arms 46C.

The distal portion 40C can be the same as the distal portion 40 of the first embodiment except that the cross-section along the radial direction R is approximately circular.

The pair of deployment arms 46C can be connected to the capsule 3 in a separable manner. Each of the pair of deployment arms 46C can include a raised portion 461 and the curved portion 49.

Figure 31:
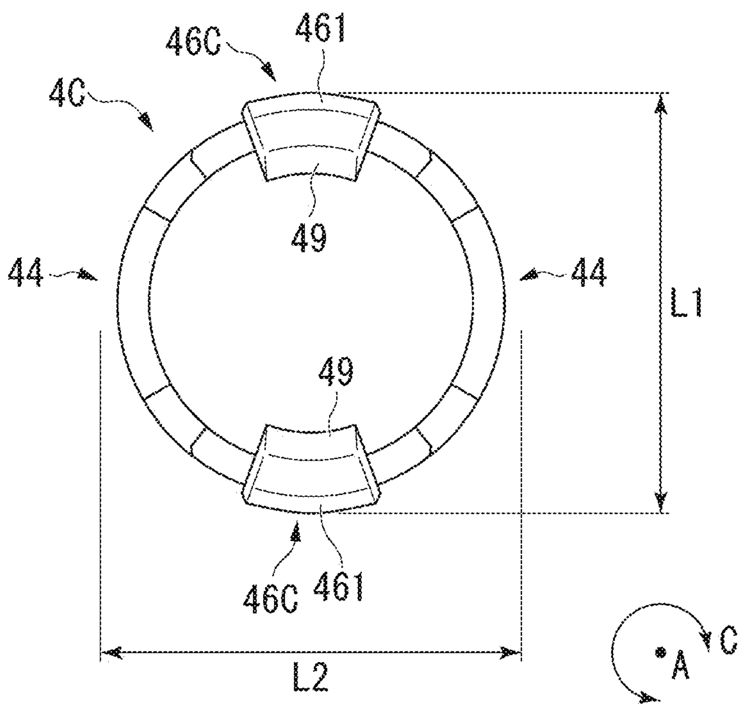
FIG. 31 illustrates an example diagram showing the same coupler seen from the proximal side in the longitudinal direction.

FIG. 31 illustrates an example diagram showing the coupler 4C when viewed from the proximal side of the longitudinal direction A.

The raised portion 461 can be a portion that is raised (projected) more outward in the radial direction R than other portions of the coupler 4C. The raised portion 461 can be provided on more distal side than a position of the curved portion 49. The outer diameter L1 of the coupler 4C in the direction in which the pair of deployment arms 46C face each other in the radial direction R can be longer than the outer diameter L2 of the coupler 4C in the direction in which the pair of retention arms 44 face each other in the radial direction R.

Figure 32:
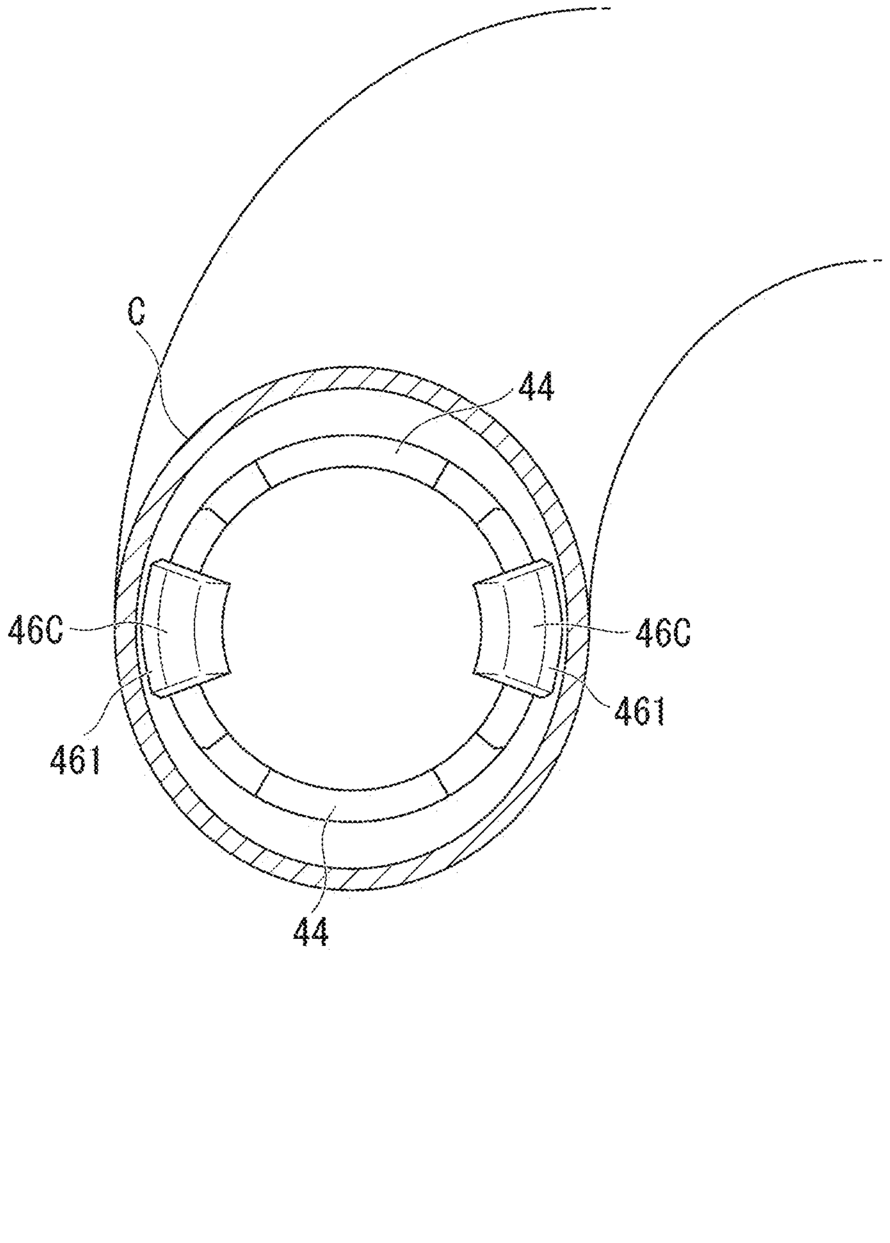
FIG. 32 illustrates an example diagram showing the same coupler passing through a curved channel.

FIG. 32 illustrates an example diagram showing the coupler 4C passing through the curved channel C.

When the channel C of the endoscope is curved, the cross-section perpendicular to the longitudinal direction A can be flat (or substantially flat). In the coupler 4C, since the outer diameter L1 is longer than the outer diameter L2, the posture of the coupler 4C can be corrected so that the pair of retention arms 44 are not placed in the inner and outer rings of the channel C when passing through the curved channel C having a flat cross-section. Accordingly, the pair of retention arms 44 connected to the bushing 210 are not deformed outward in the radial direction R and the coupler 4C can be less likely to fall off from the applicator 200.

Figure 33:
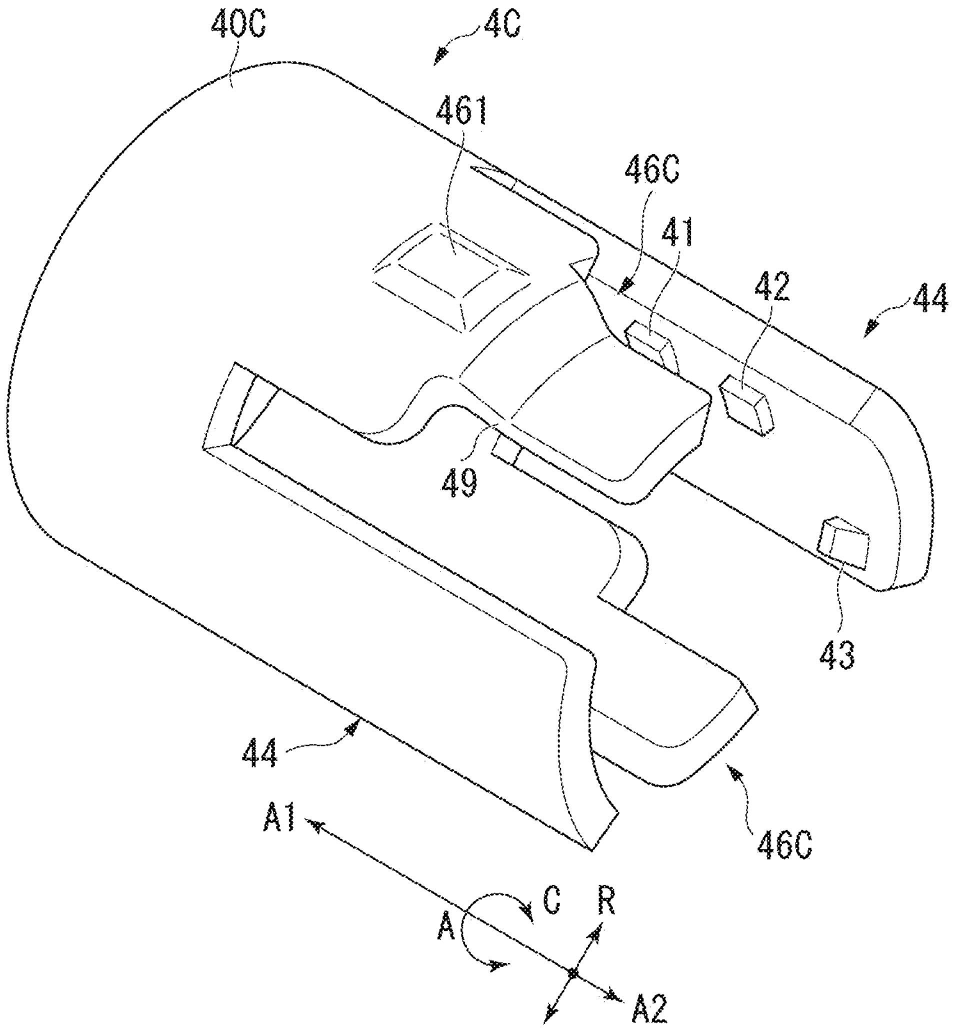
FIG. 33 illustrates an example perspective view of another form of the same coupler.
Figure 34:
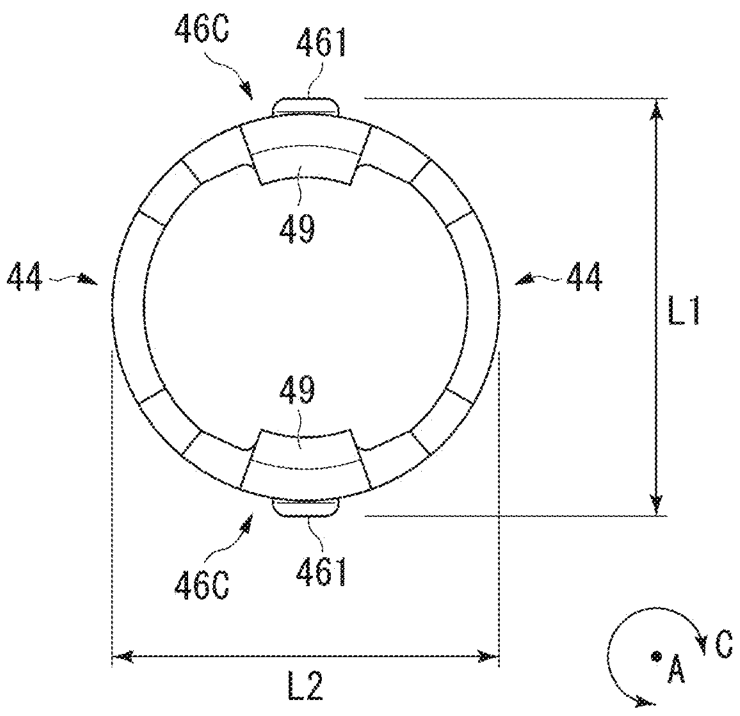
FIG. 34 illustrates an example diagram showing the coupler shown in FIG. 33 seen from the proximal side in the longitudinal direction.

FIG. 33 illustrates an example perspective view of another embodiment of the coupler 4C. FIG. 34 illustrates an example diagram showing the coupler 4C shown in FIG. 33 when viewed from the proximal side of the longitudinal direction A. The raised portion 461 can be formed by at least a portion of the outer circumferential surface of the pair of deployment arms 46C raised (projected) outward in the radial direction R.

According to the clip system 500C of this embodiment, the coupler 4C can be less likely to fall off from the applicator 200 and can be easily passed through the channel of the endoscope.

Although the third embodiment of the present disclosure has been described above in detail with reference to the drawings, the specific configuration is not limited to this embodiment, and design changes can be made within the of the present disclosure. Furthermore, the components shown in the embodiments and modified examples can be configured by appropriately combining them.

Fourth Embodiment

A fourth embodiment of the present disclosure is described with reference to FIGS. 35 to 38. In the following description, components that are common to those already described will be indicated by the same reference numerals and redundant description will be omitted.

Figure 35:
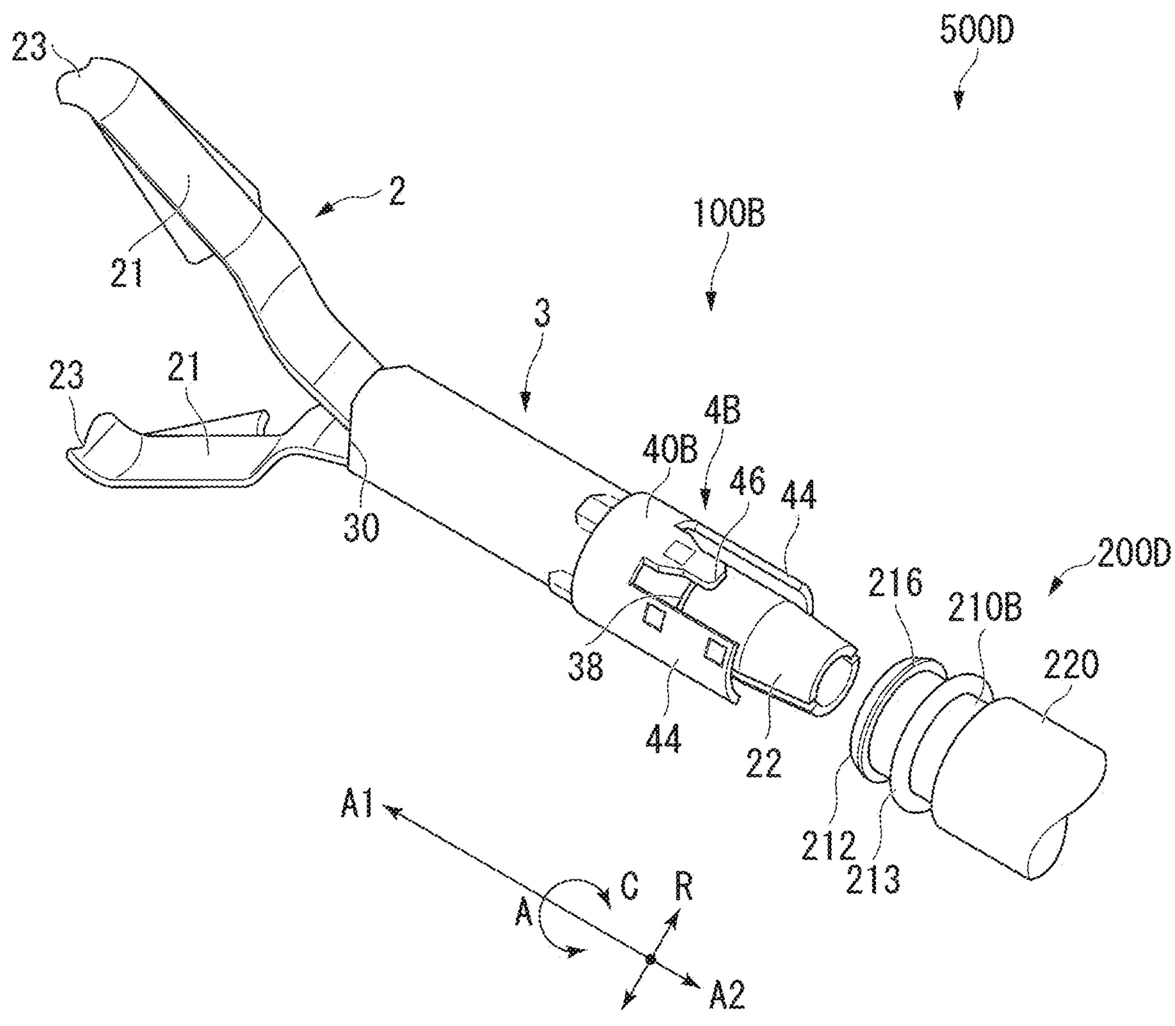
FIG. 35 illustrates an example diagram showing a part of a clip system according to a fourth embodiment of the present disclosure.

FIG. 35 illustrates an example diagram showing a part of a clip system 500D.

The clip system 500D according to this embodiment can include the clip unit 100B, an applicator 200D, and the cartridge 300.

The applicator 200D can include a sheath 220D, the operating wire 230, and the operating section 240.

The sheath 220D can be made to be flexible and curved to match the curvature of the insertion section of the endoscope. The sheath 220D can extend from the proximal end connected to the operating section 240 that remains outside the body while clipping the target tissue to the distal end including a bushing 210D connecting the applicator 200D to the clip unit 100B.

Figure 36:
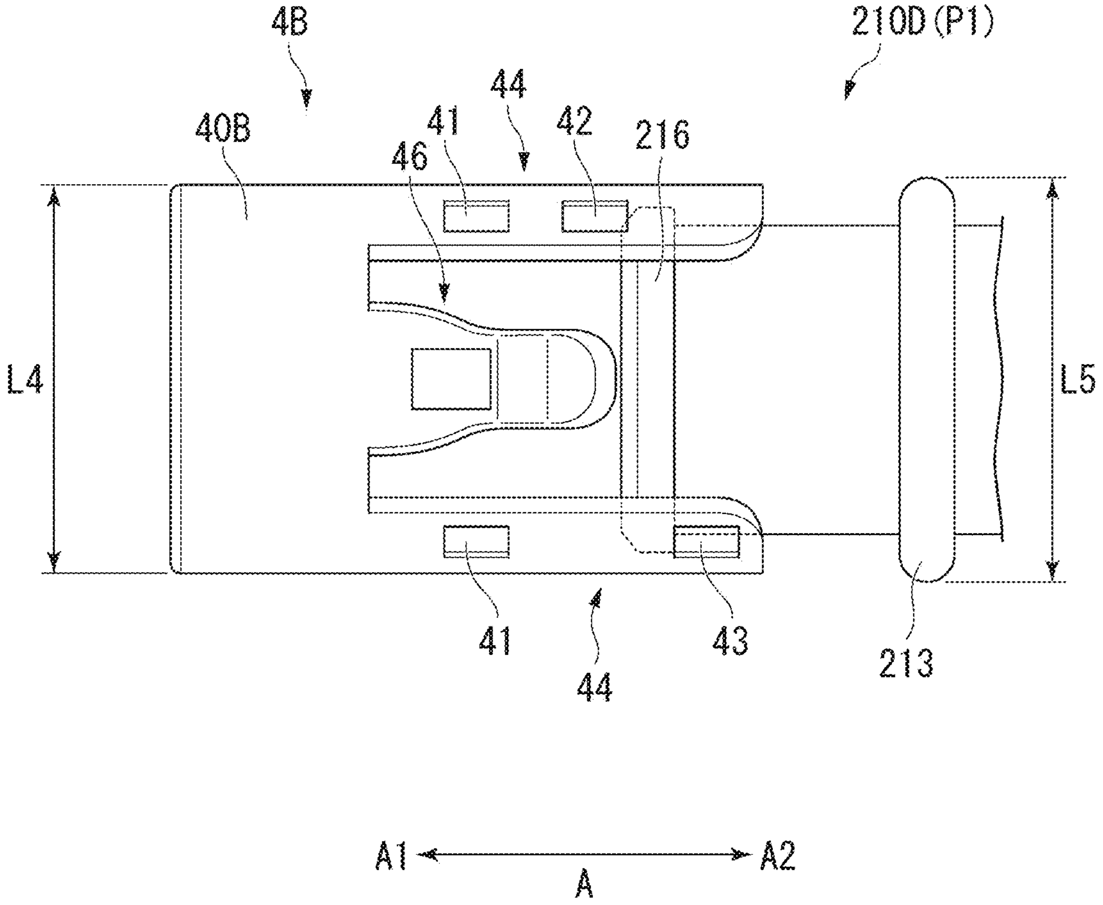
FIG. 36 illustrates an example diagram showing a bushing disposed at a first position.

FIG. 36 illustrates an example diagram showing the bushing 210D disposed at the first position P1.

The bushing 210D can be the same as the bushing 210 of the first embodiment except that a convex portion 213 is provided on the proximal side of the projection 216 provided at the distal end 212.

The convex portion 213 can extend from the outer surface 215 outward in the radial direction R and the outer diameter L5 in the radial direction R can be larger than the outer diameter L4 of the coupler 4B. The convex portion 213 can be provided along the circumferential direction C on the entire circumference of the bushing 210. The convex portion 213 can be provided only at a part of the circumferential direction C.

Figure 37:
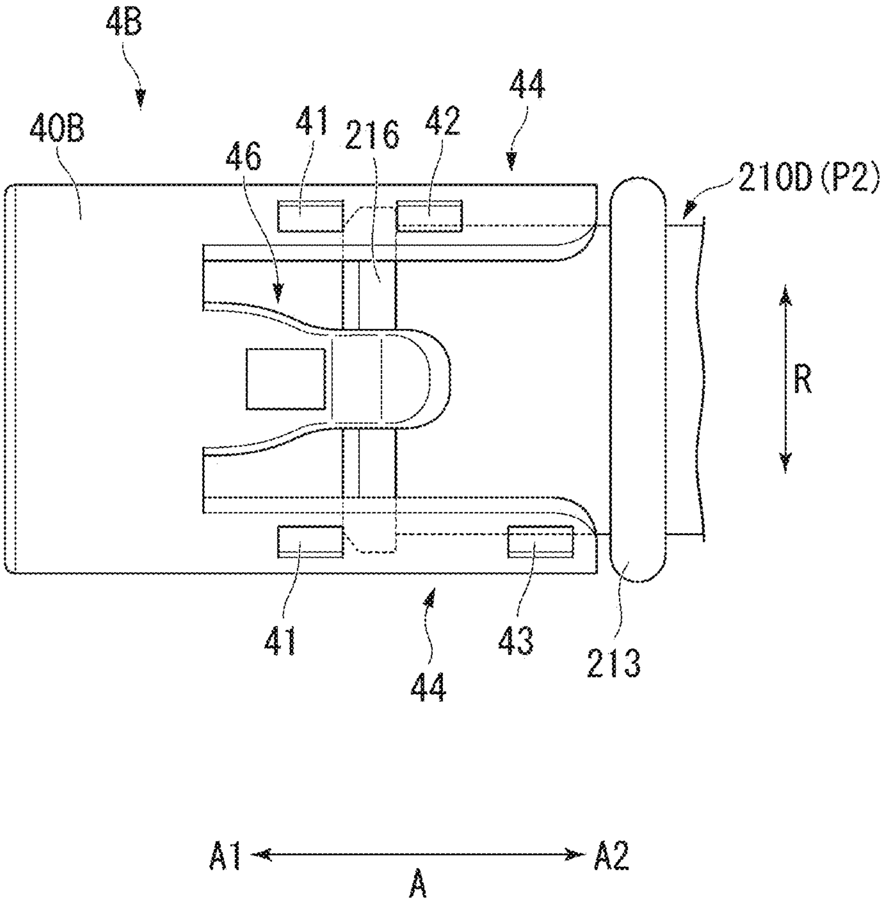
FIG. 37 illustrates an example diagram showing the same bushing disposed at a second position.

FIG. 37 illustrates an example diagram showing the bushing 210D disposed at the second position P2.

When the bushing 210D is disposed at the second position P2, the convex portion 213 can be disposed on more proximal side than a position of the coupler 4B. When the bushing 210D is disposed at the second position P2, the convex portion 213 can be disposed near the coupler 4B.

Figure 38:
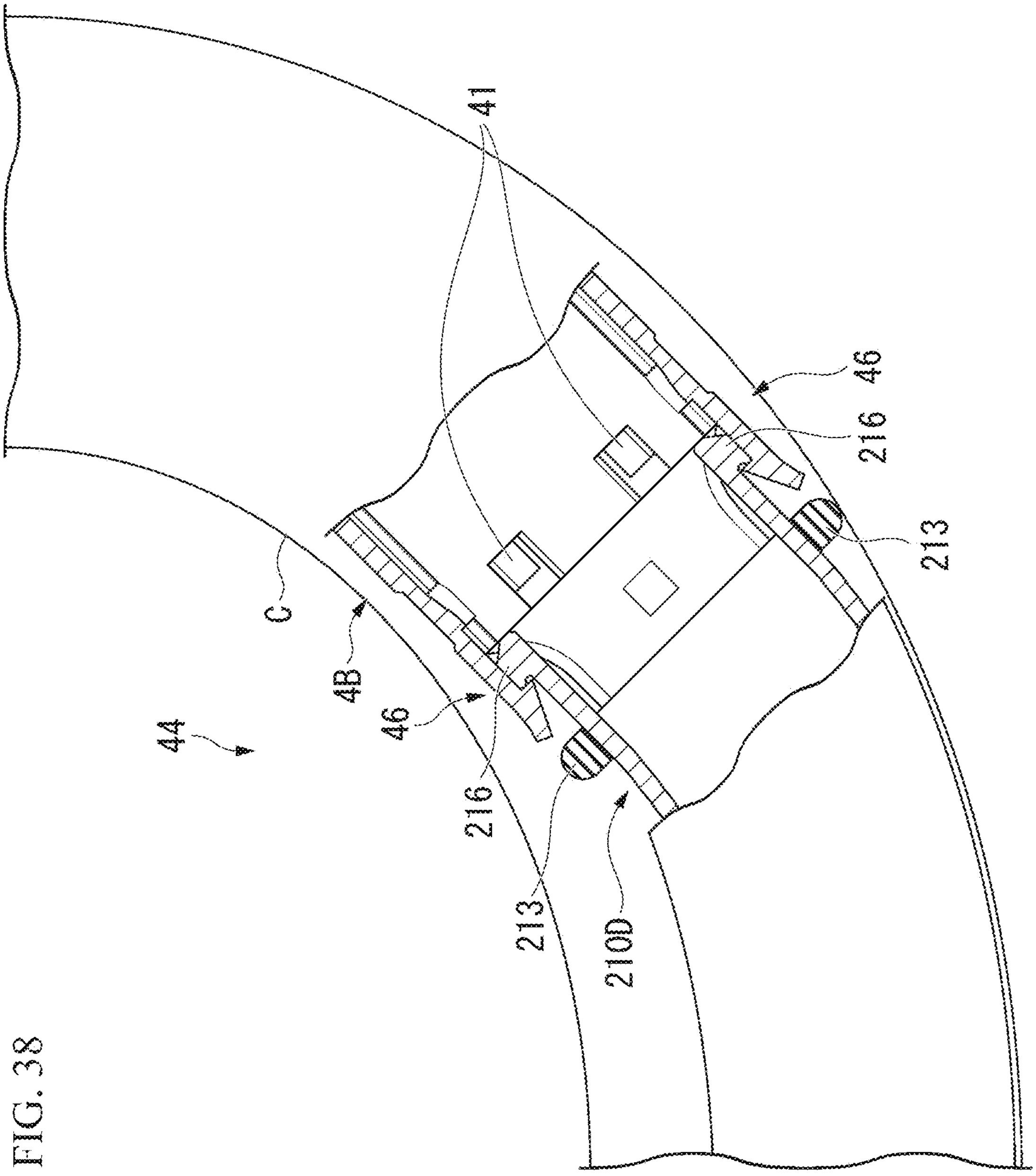
FIG. 38 illustrates an example diagram showing a coupler passing through a curved channel.

FIG. 38 illustrates an example diagram showing the coupler 4B passing through the curved channel C.

The coupler 4B can include a sharp part, and as such, the coupler cannot come into contact with the inner peripheral surface of the channel C. Since the outer diameter L5 of the convex portion 213 is larger than the outer diameter L4 of the coupler 4B, the coupler 4B can be less likely to come into contact with the inner peripheral surface of the channel C. Therefore, when the applicator 200D connected to the coupler 4B is removed from the channel C of the endoscope, the coupler 4B can be easily passed through the channel C of the endoscope.

According to the clip system 500D of this embodiment, the coupler 4B can be less likely to fall off from the applicator 200D and can be easily passed through the channel of the endoscope.

Although the fourth embodiment of the present disclosure has been described above in detail with reference to the drawings, the specific configuration is not limited to this embodiment, and design changes can be made within the scope of the present disclosure. Furthermore, the components shown in the embodiments and modified examples can be configured by appropriately combining them.

Fifth Embodiment

A fifth embodiment of the present disclosure is described with reference to FIGS. 39 to 41. In the following description, components that are common to those already described will be indicated by the same reference numerals and redundant description will be omitted.

Figure 39:
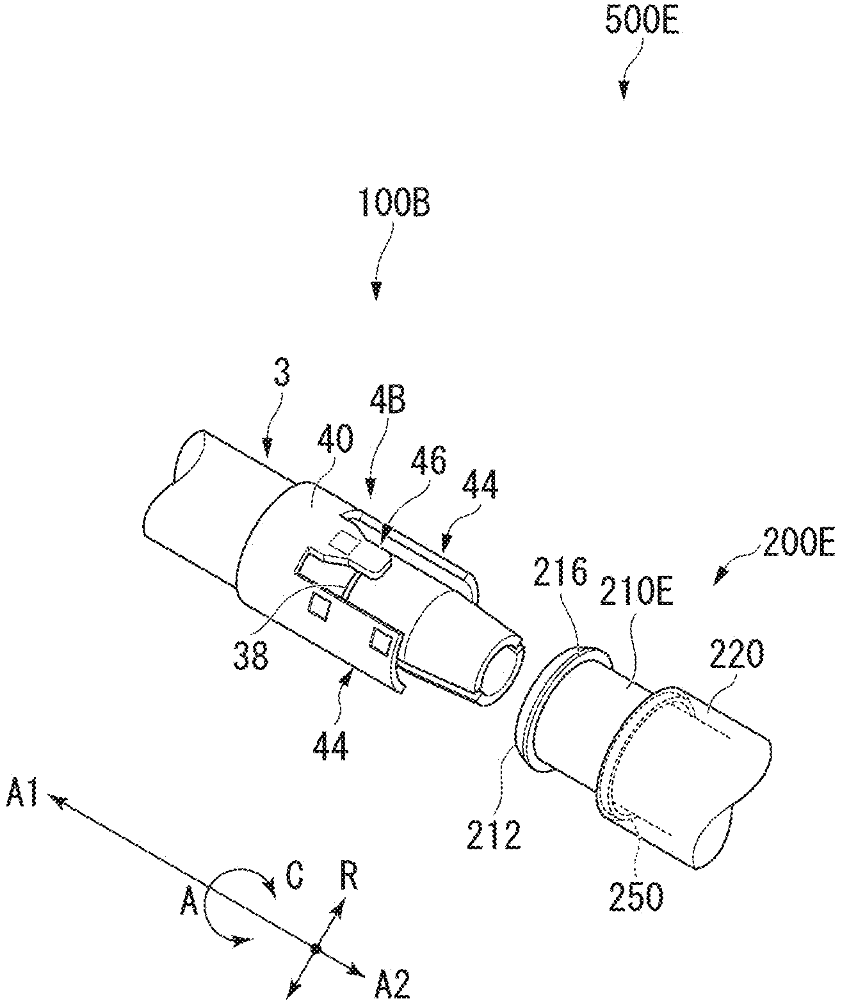
FIG. 39 illustrates an example diagram showing a part of a clip system according to a fifth embodiment of the present disclosure.

FIG. 39 illustrates an example diagram showing a part of a clip system 500E.

The clip system 500E according to this embodiment can include the clip unit 100B, an applicator 200E, and the cartridge 300.

The applicator 200E can include a sheath 220E, the operating wire 230, and the operating section 240.

The sheath 220E can be made to be flexible and curved to match the curvature of the insertion section of the endoscope. The sheath 220E can extend from the proximal end connected to the operating section 240 that remains outside the body while clipping the target tissue to the distal end including a bushing 210E connecting the applicator 200E to the clip unit 100B.

The bushing 210E can be the same as the bushing 210 of the first embodiment except that the coupler accommodation portion 250 is provided.

Figure 40:
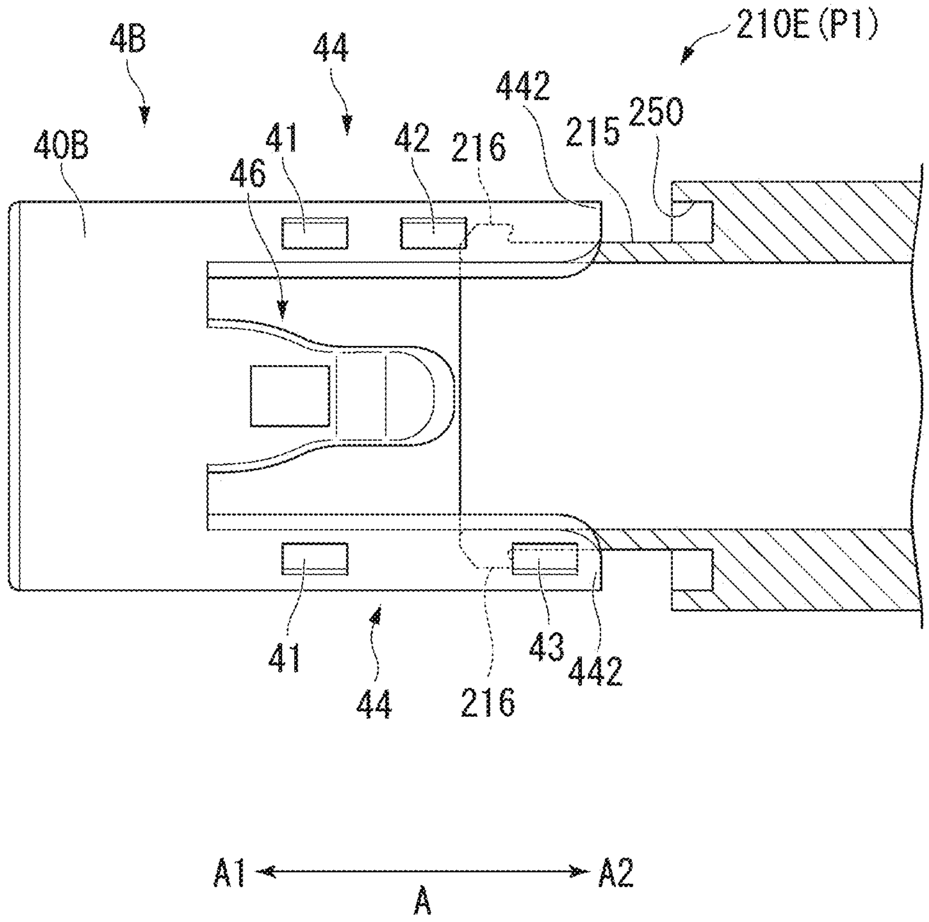
FIG. 40 illustrates an example diagram showing a bushing disposed at a first position.

FIG. 40 illustrates an example cross-sectional view of the bushing 210E disposed at the first position P1.

The coupler accommodation portion 250 can be a groove which is provided on the outer surface 215 of the bushing 210E and can accommodate at least proximal ends 442 of the pair of retention arms 44. The coupler accommodation portion 250 can be opened toward the distal end and can be provided along the circumferential direction C on the entire circumference of the bushing 210.

Figure 41:
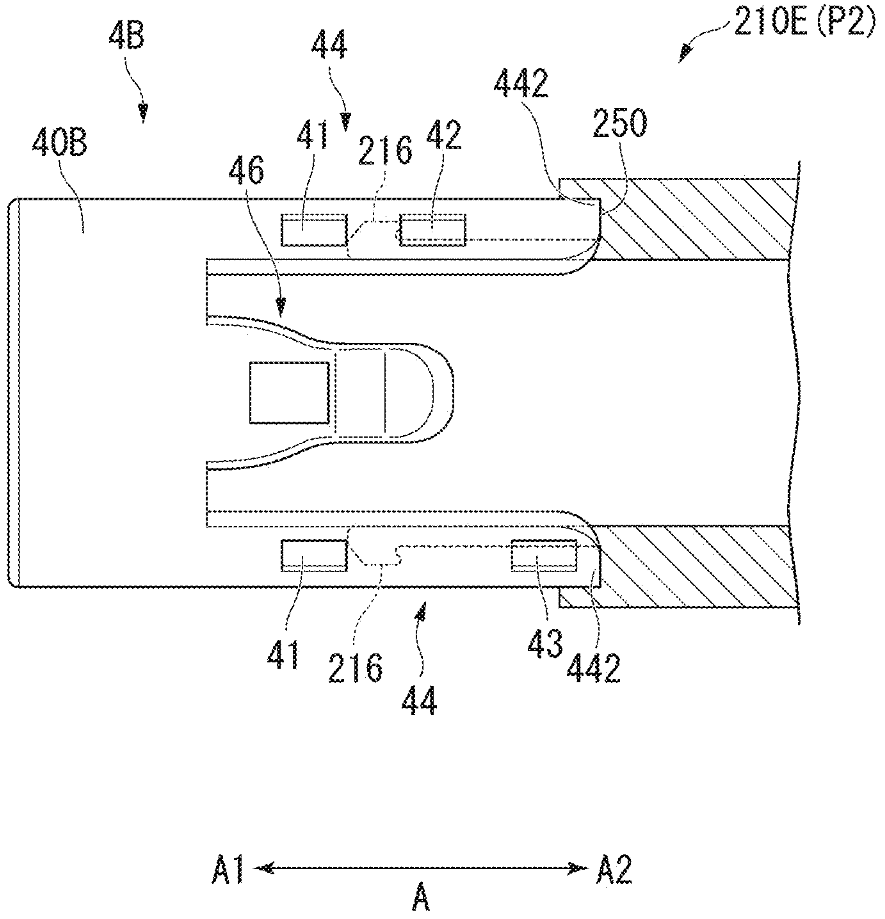
FIG. 41 illustrates an example diagram showing the same bushing disposed at a second position.

FIG. 41 illustrates an example cross-sectional view of the bushing 210E disposed at the second position P2.

When the bushing 210E is disposed at the second position P2, the coupler accommodation portion 250 can accommodate the proximal ends 442 of the pair of retention arms 44. Since the proximal ends of the pair of retention arms 44 are accommodated in the coupler accommodation portion 250, the proximal ends can be less likely to come into contact with the inner peripheral surface of the channel of the endoscope. Therefore, when the applicator 200E connected to the coupler 4B is removed from the channel of the endoscope, the coupler 4B can be less likely to fall off from the applicator 200E.

According to the clip system 500E of this embodiment, the coupler 4B can be less likely to fall off from the applicator 200E and can be easily passed through the channel of the endoscope.

Although the fifth embodiment of the present disclosure has been described above in detail with reference to the drawings, the specific configuration is not limited to this embodiment, and design changes can be made within the scope of the present disclosure. Furthermore, the components shown in the embodiments and modified examples can be configured by appropriately combining them.

Modified Example 5-1

Figure 42:
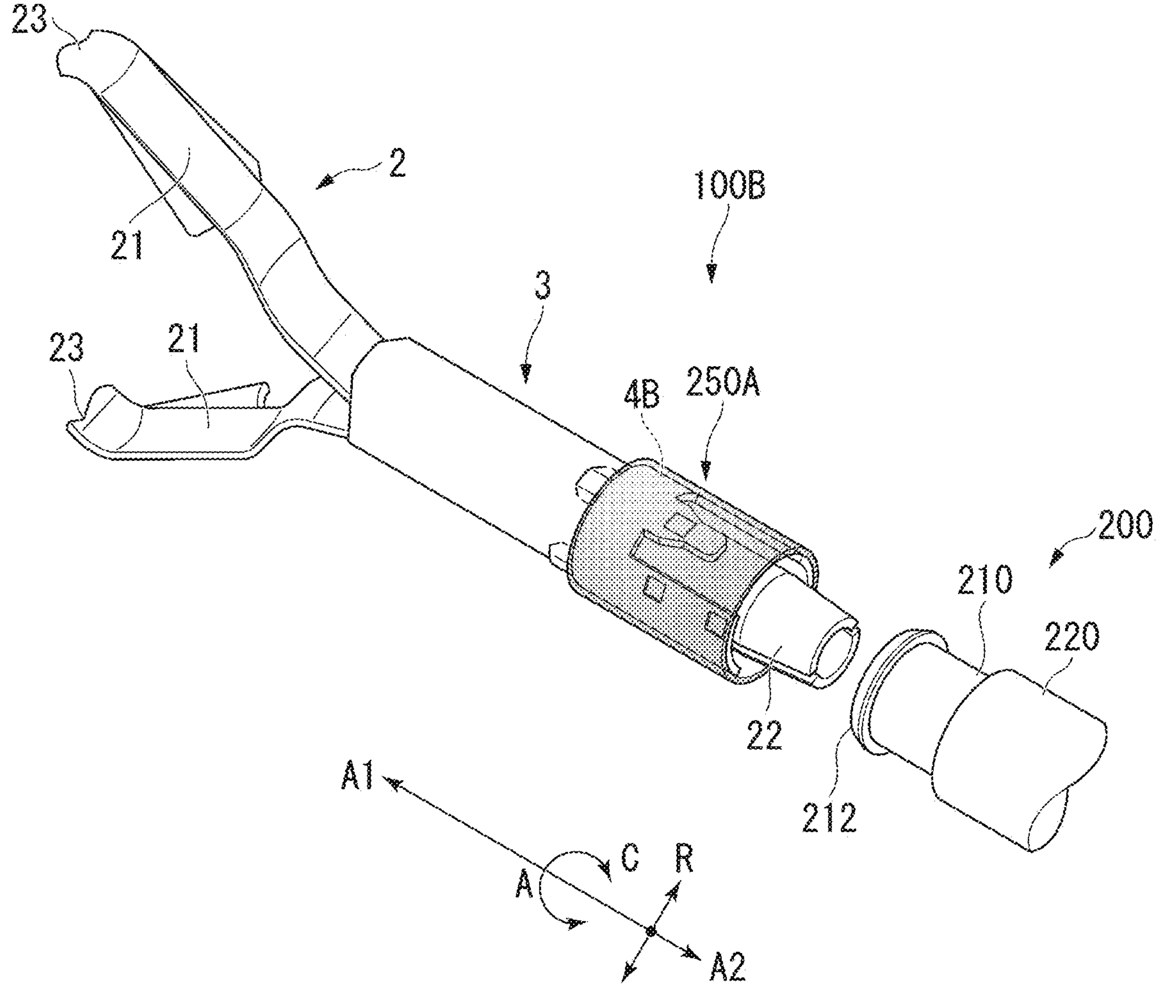
FIG. 42 illustrates an example diagram showing a modified example of a coupler accommodation portion.
Figure 43:
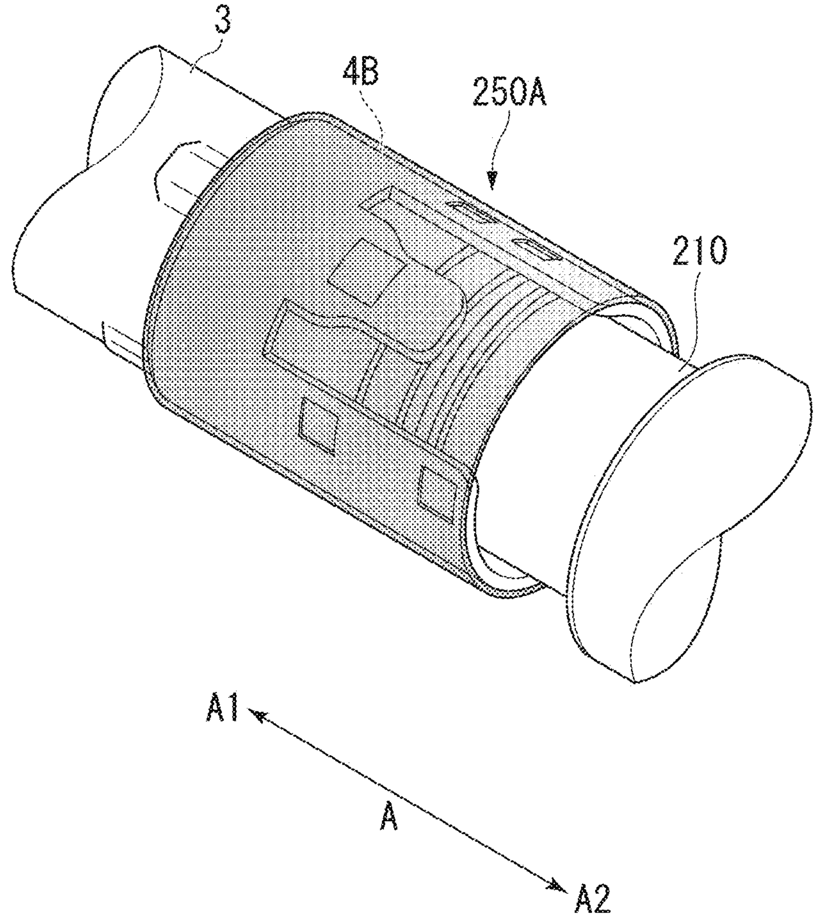
FIG. 43 illustrates an example diagram showing the same modified example of the same coupler accommodation portion.

FIGS. 42 and 43 illustrate example diagrams showing a coupler accommodation portion 250A which is a modified example of the coupler accommodation portion 250. The coupler accommodation portion 250A can be a cover that is separated from the bushing 210. The coupler accommodation portion 250A can be made of, for example, metal or resin with no (or substantially no) unevenness. Almost the entire coupler 4B can be covered by the coupler accommodation portion 250A. Therefore, when the applicator 200 connected to the coupler 4B is removed from the channel of the endoscope, the coupler 4B can be less likely to fall off from the applicator 200.

Modified Example 5-2

Figure 44:
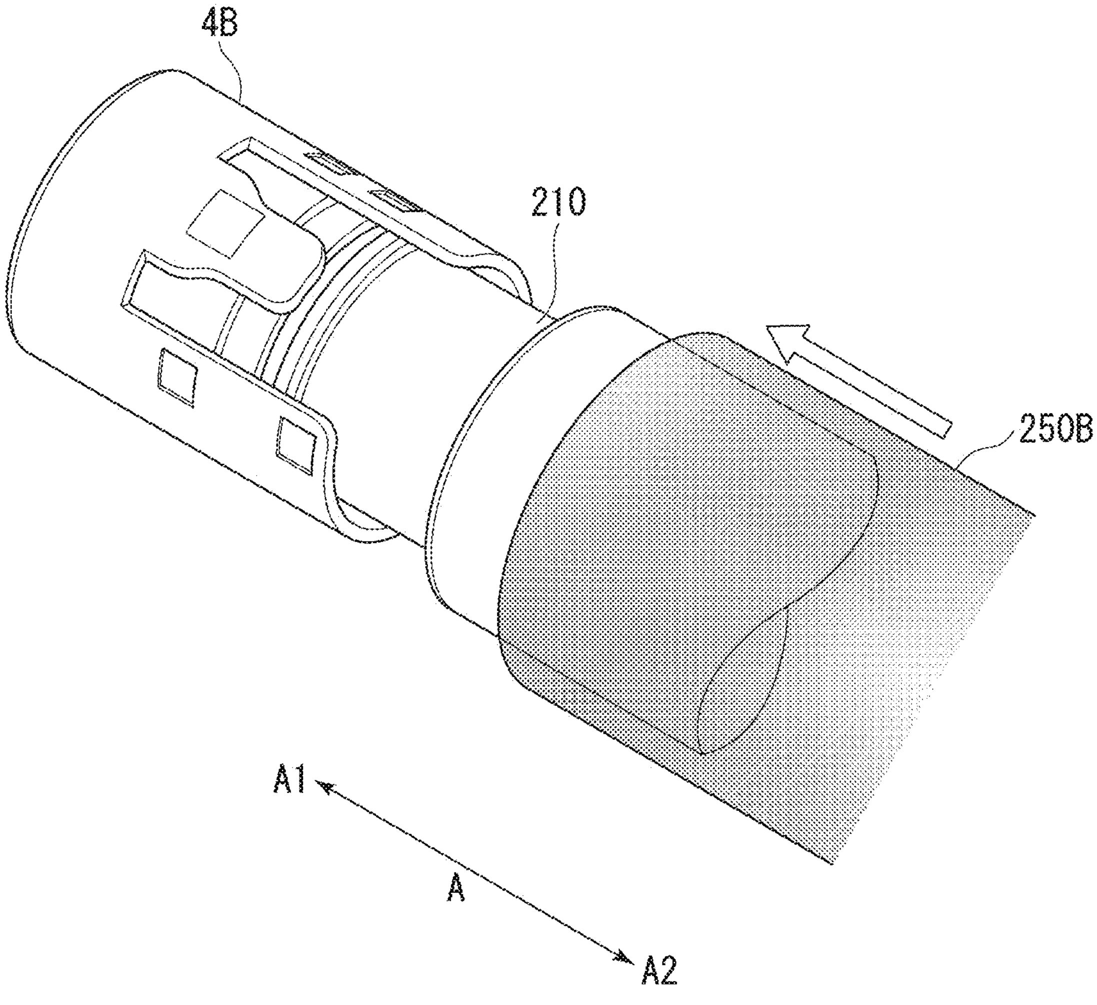
FIG. 44 illustrates an example diagram showing another modified example of the same coupler accommodation portion.
Figure 45:
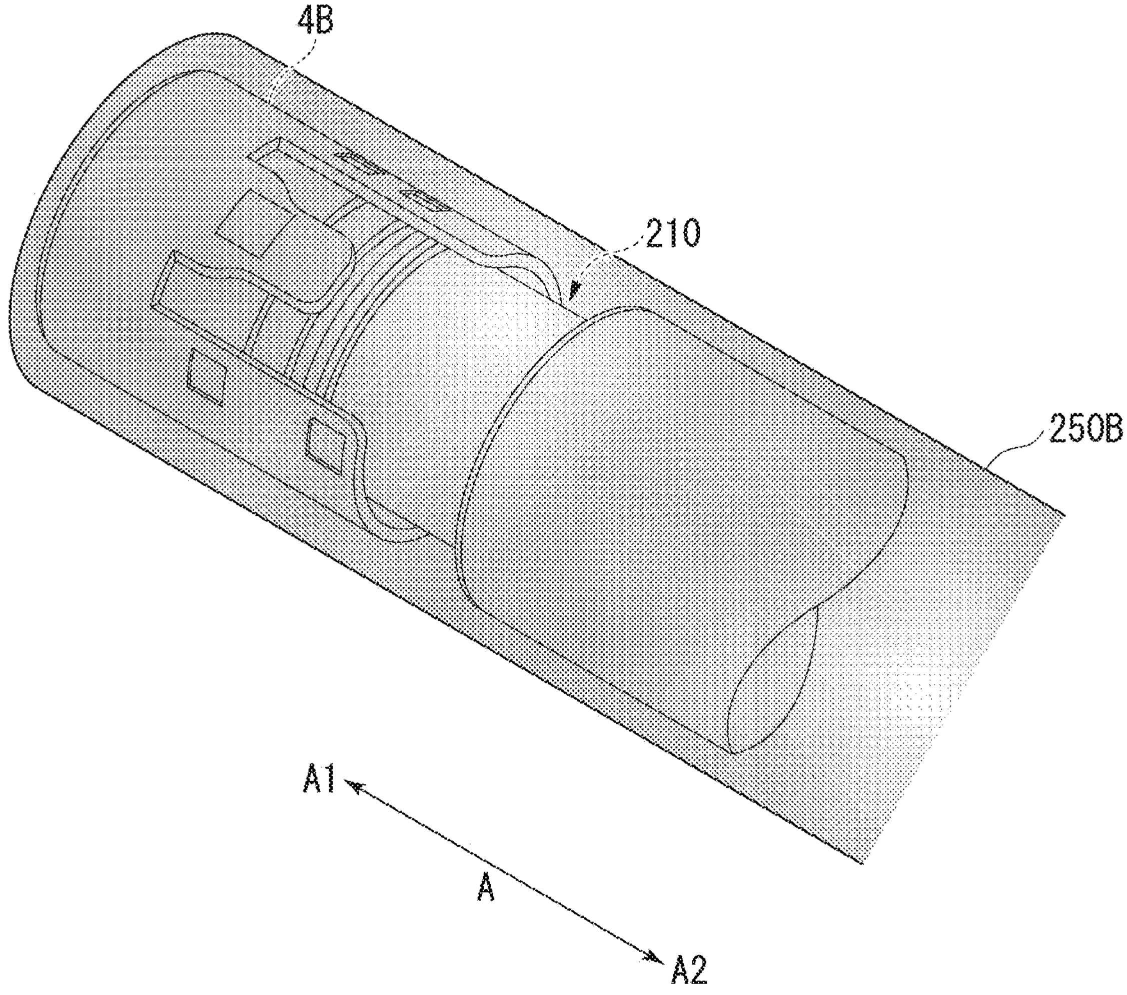
FIG. 45 illustrates an example diagram showing the same modified example of the same coupler accommodation portion.

FIGS. 44 and 45 illustrate example diagrams showing a coupler accommodation portion 250B which is a modified example of the coupler accommodation portion 250. The coupler accommodation portion 250B can be an outer sheath separated from the bushing 210. The coupler accommodation portion 250B can be disposed on the outer peripheral side of the bushing 210 and is able to advance and retract with respect to the bushing 210. By advancing the coupler accommodation portion 250B with respect to the bushing 210, almost the entire coupler 4B can be covered by the coupler accommodation portion 250B. Therefore, when the applicator 200 connected to the coupler 4B is removed from the channel of the endoscope, the coupler 4B can be less likely to fall off from the applicator 200.

Sixth Embodiment

A sixth embodiment of the present disclosure is described with reference to FIGS. 46 and 47. In the following description, components that are common to those already described will be indicated by the same reference numerals and redundant description will be omitted.

Figure 46:
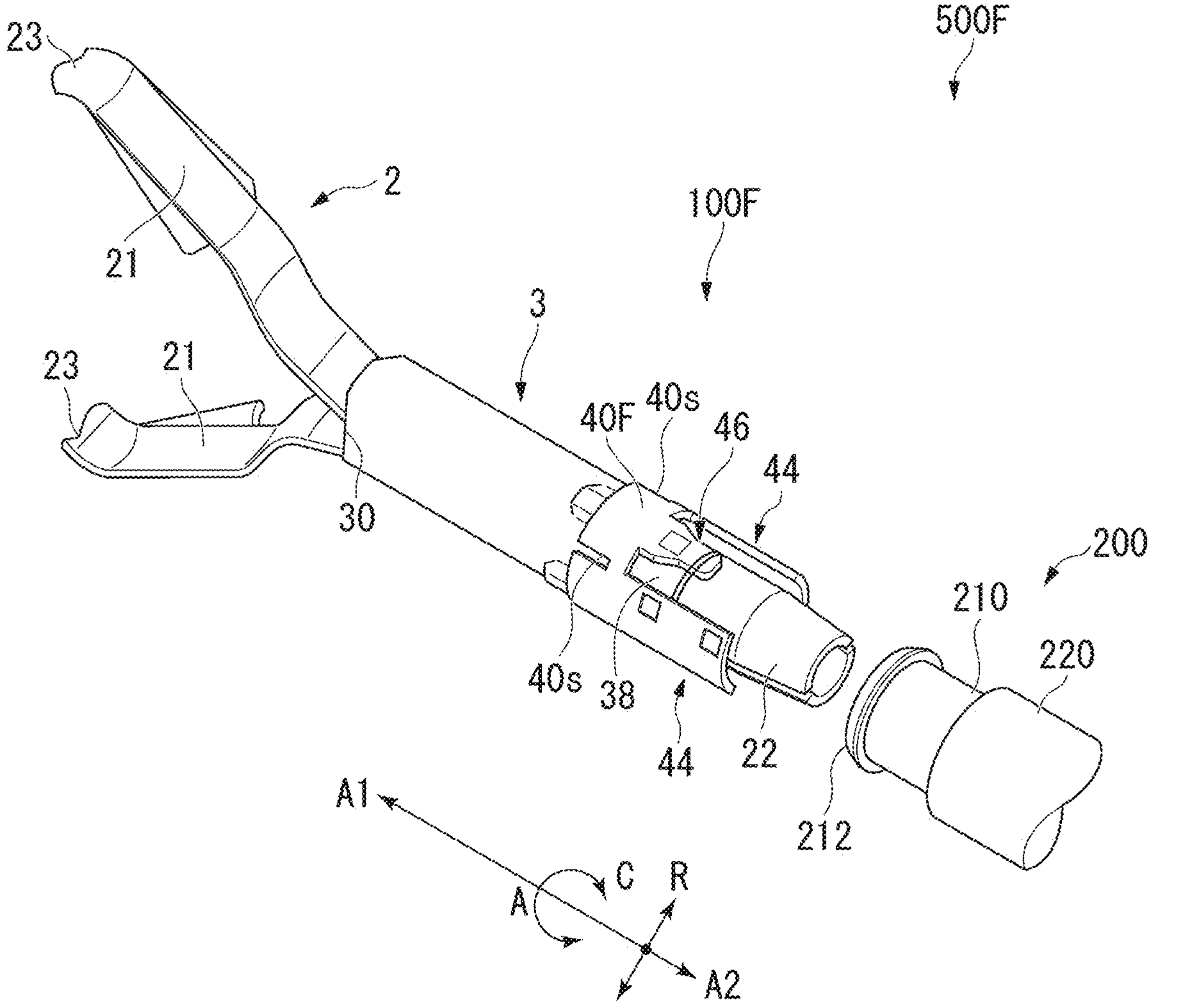
FIG. 46 illustrates an example diagram showing a part of a clip system according to a sixth embodiment of the present disclosure.

FIG. 46 illustrates an example diagram showing a part of a clip system 500F.

The clip system 500F according to this embodiment can include a clip unit 100F, the applicator 200, and the cartridge 300.

The clip unit 100F can include the clip 2, the capsule 3, and a coupler 4F.

The coupler 4F can be connected to the proximal end 38 of the capsule 3 of the clip unit 100F before the clip unit 100F is loaded into the applicator 200. The coupler 4F can include a distal portion 40F, the pair of retention arms 44, and the pair of deployment arms 46.

The distal portion 40F can be the same as the distal portion 40B of the second embodiment except that a plurality of slits 40*s* are provided.

The slit 40*s* can be a groove that extends from the distal end of the distal portion 40F along the longitudinal direction A and can penetrate the distal portion 40F in the radial direction R. The slit 40*s* can be arranged at substantially the same position in the circumferential direction C as both ends of the pair of retention arms 44 in the circumferential direction C.

Figure 47:
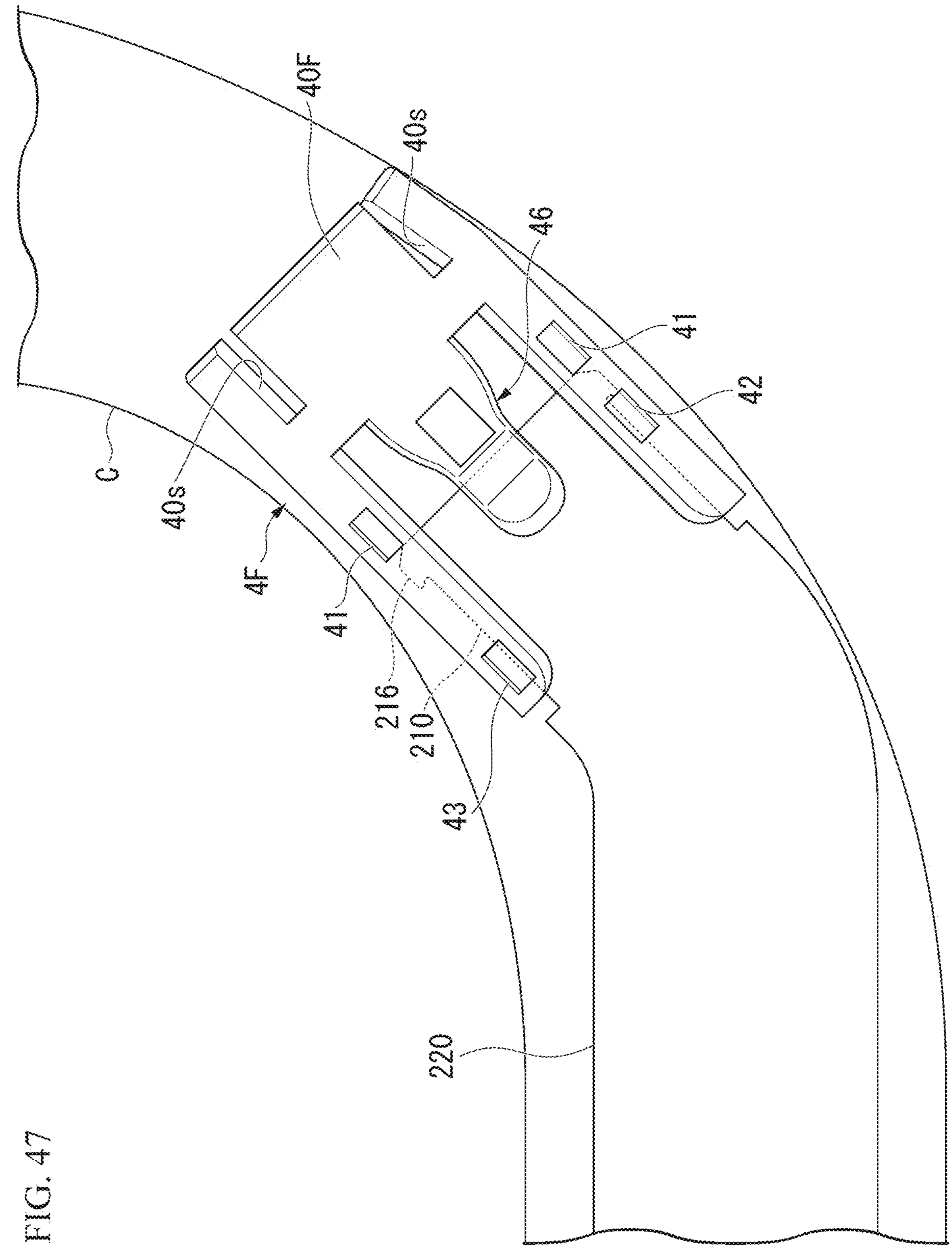
FIG. 47 illustrates an example diagram showing a coupler passing through a curved channel.

FIG. 47 illustrates an example diagram showing the coupler 4F passing through the curved channel C.

The distal portion 40F of the coupler 4F can be deformed inward when coming into contact with the inner peripheral surface of the channel C. The coupler 4F connected to the bushing 210 can be formed so as to be strong against bending loads from the outside in the radial direction R and thus can be less likely to fall off. Therefore, when the applicator 200 connected to the coupler 4F is removed from the channel C of the endoscope, the coupler 4F can be easily passed through the channel C of the endoscope.

According to the clip system 500F of this embodiment, the coupler 4F can be formed so as to be less likely to fall off from the applicator 200 and can be easily passed through the channel of the endoscope.

Although the sixth embodiment of the present disclosure has been described above in detail with reference to the drawings, the specific configuration is not limited to this embodiment, and design changes can be made within the scope of the present disclosure. Furthermore, the components shown in the embodiments and modified examples can be configured by appropriately combining them.

Modified Example 6-1

Figure 48:
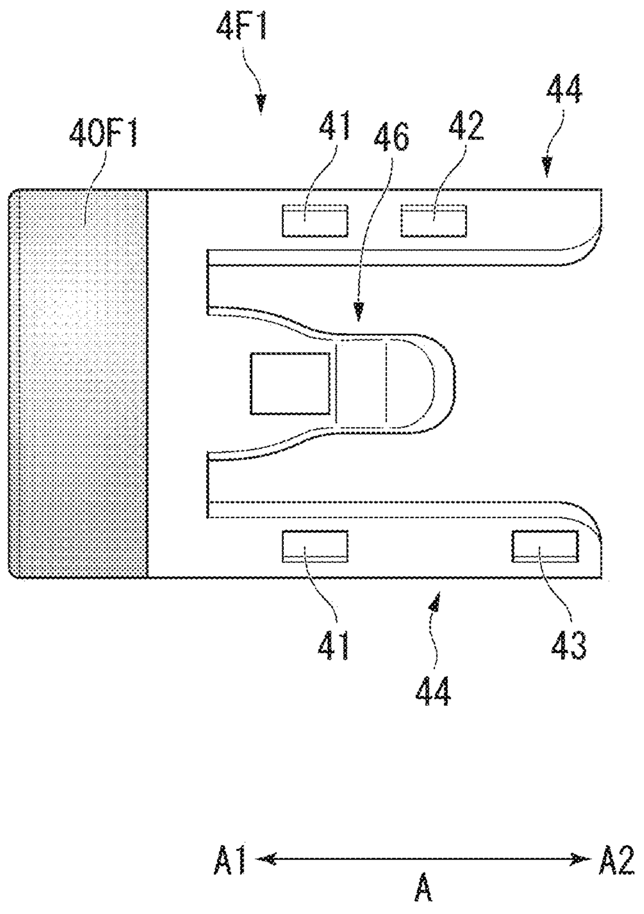
FIG. 48 illustrates an example diagram showing a modified example of the same coupler.

FIG. 48 illustrates an example diagram showing a coupler 4F1 which is a modified example of the coupler 4F.

The coupler 4F1 can include a distal portion 40F1 which is a modified example of the distal portion 40F. In an example, the distal portion 40F1 does not include the slit 40*s*. The distal portion 40F1 can be made of a flexible member, for example, made of resin. The distal portion 40F1 of the coupler 4F1 can be deformed inward when coming into contact with the inner peripheral surface of the channel C similarly to the distal portion 40F.

Modified Example 6-2

Figure 49:
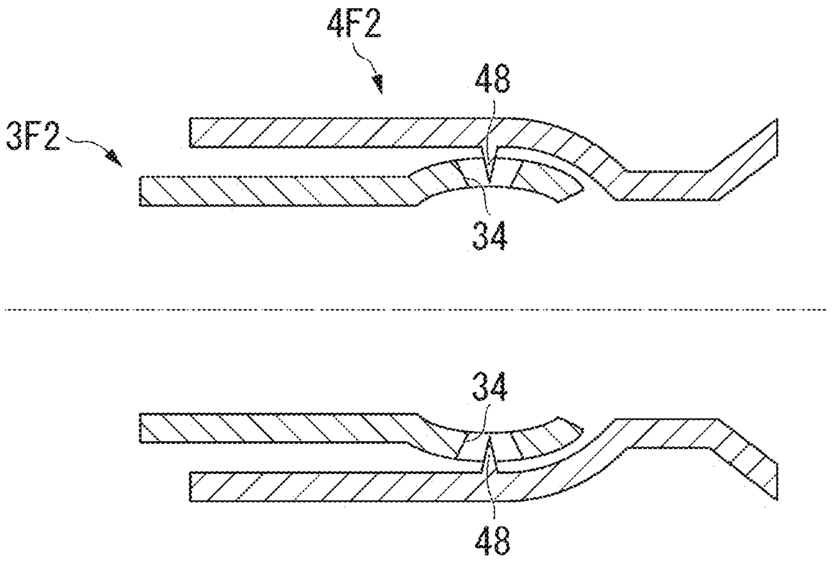
FIG. 49 illustrates an example diagram showing a modified example of the same coupler.
Figure 50:
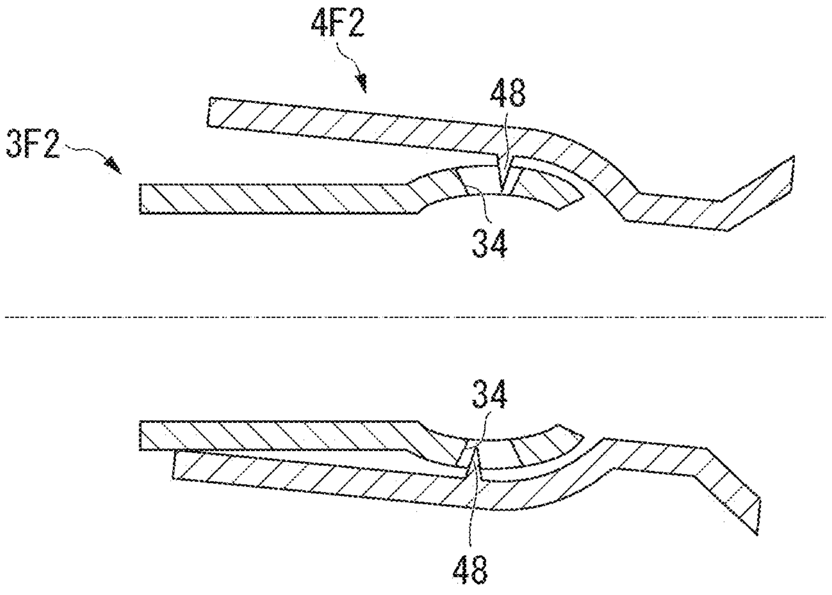
FIG. 50 illustrates an example diagram showing the same modified example of the same coupler.

FIGS. 49 and 50 illustrate example diagrams showing a coupler 4F2 which is a modified example of the coupler 4F.

The coupler 4F2 can be connected to a capsule 3F2 which is a modified example of the capsule 3. A clear land can be provided at the portion where the engagement element 48 of the coupler 4F2 and the opening 34 of the capsule 3F2 engage, and the coupler 4F2 can be easily bent with respect to the capsule 3F2.

Modified Example 6-3

Figure 51:
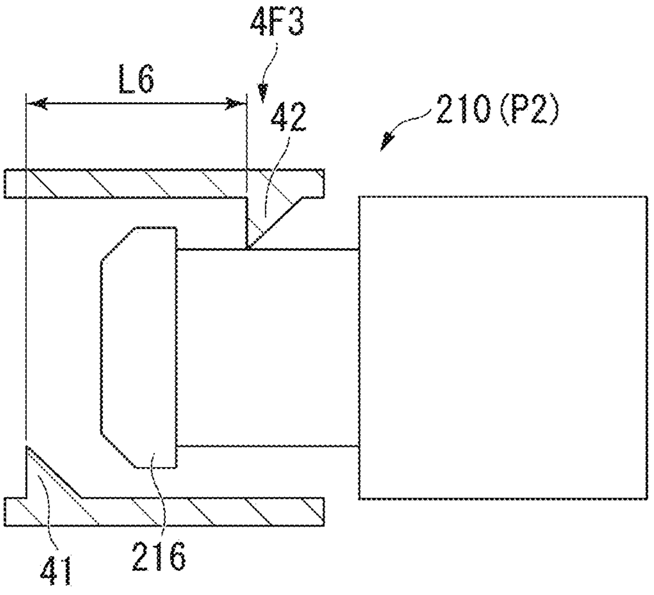
FIG. 51 illustrates an example diagram showing another modified example of the same coupler.
Figure 52:
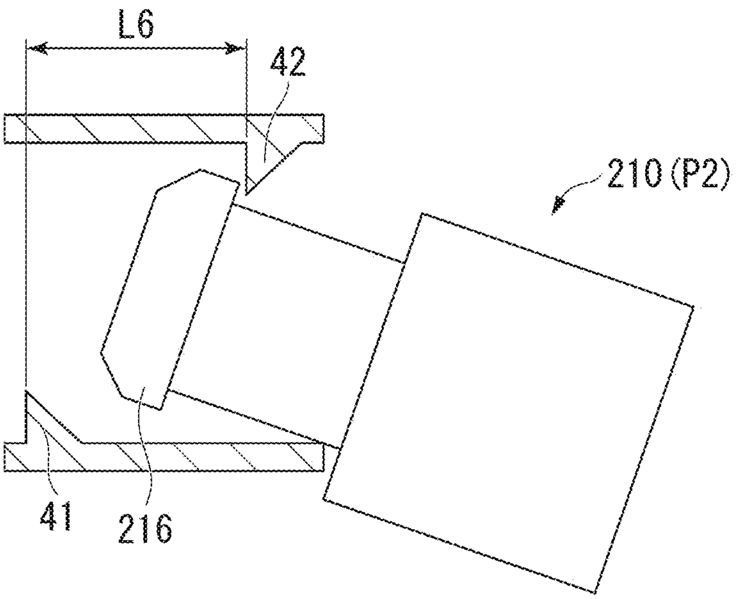
FIG. 52 illustrates an example diagram showing the same modified example of the same coupler.

FIGS. 51 and 52 illustrate example diagrams showing a coupler 4F3 which is a modified example of the coupler 4F.

In the coupler 4F3, the length L6 from the first protrusion 41 to the second protrusion 42 in the longitudinal direction A can be longer than that of the coupler 4. When a bending load is applied from the outside in the radial direction R, the coupler 4F3 can be bent with respect to the bushing 210. Therefore, when the applicator 200 connected to the coupler 4F3 is removed from the channel C of the endoscope, the coupler 4F3 can be easily passed through the channel C of the endoscope.

Modified Example 6-4

Figure 53:
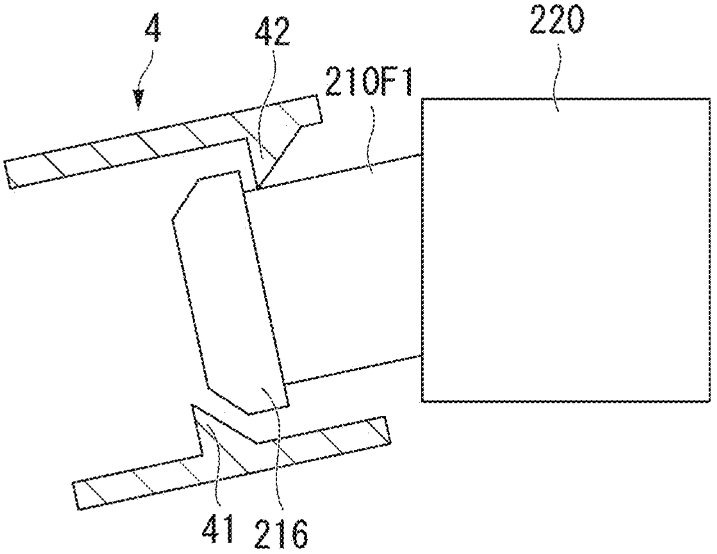
FIG. 53 illustrates an example diagram showing a modified example of a bushing.

FIG. 53 illustrates an example diagram showing a bushing 210F1 which is a modified example of the bushing 210.

The bushing 210F1 can be made of an elastic member. When a bending load is applied from the outside in the radial direction R, the coupler 4 can be bent with respect to the bushing 210F1. Therefore, when the applicator 200 connected to the coupler 4 is removed from the channel C of the endoscope, the coupler 4 can be easily passed through the channel C of the endoscope.

Modified Example 6-5

Figure 54:
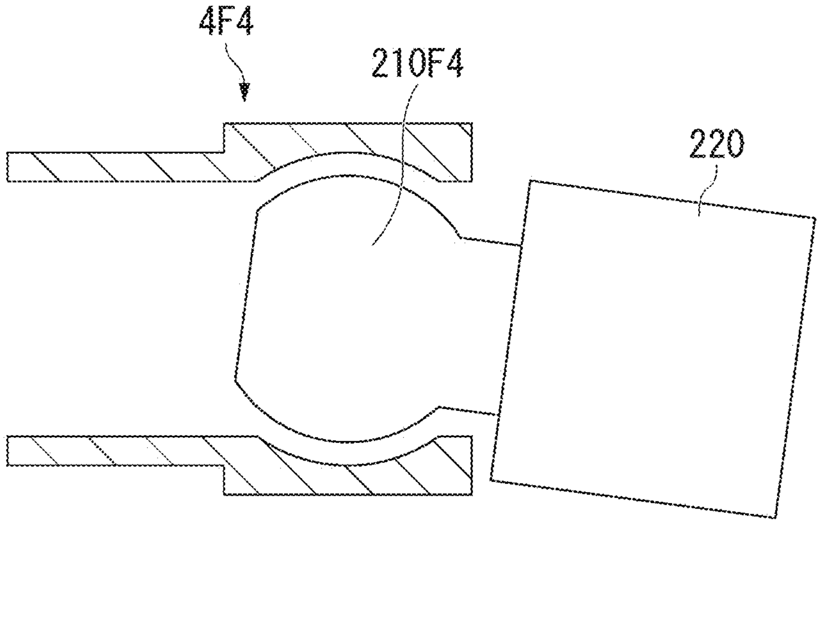
FIG. 54 illustrates an example diagram showing another modified example of the same coupler.

FIG. 54 illustrates an example diagram showing a coupler 4F4 which is a modified example of the coupler 4F.

The coupler 4F4 can be connected to a bushing 210F4 which is a modified example of the bushing 210. The coupler 4F4 and the bushing 210F4 can be connected by a ball joint. When a bending load is applied from the outside in the radial direction R, the coupler 4F4 can be bent with respect to the bushing 210F4. Therefore, when the applicator 200 connected to the coupler 4F4 is removed from the channel C of the endoscope, the coupler 4F4 can be easily passed through the channel C of the endoscope.

Modified Example 6-6

Figure 55:
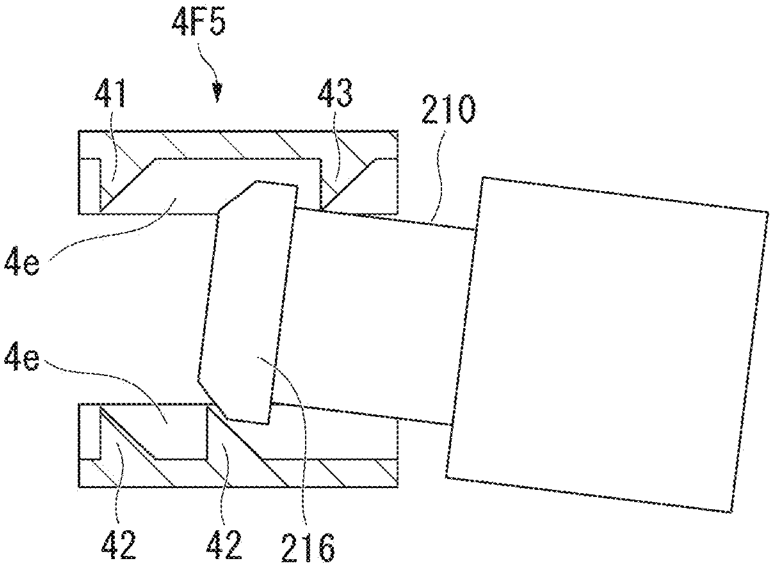
FIG. 55 illustrates an example diagram showing another modified example of the same coupler.

FIG. 55 illustrates an example diagram showing a coupler 4F5 which is a modified example of the coupler 4F.

In the coupler 4F5, an elastic member 4*e* can be attached to a portion engaged with the bushing 210. The coupler 4F5 can be bent with respect to the bushing 210 and rattling between the bushing 210 and the coupler 4F5 can be reduced.

Seventh Embodiment

A seventh embodiment of the present disclosure is described with reference to FIGS. 56 to 59. In the following description, components that are common to those already described will be indicated by the same reference numerals and redundant description will be omitted.

A clip system 500G according to this embodiment can include a clip unit 100G, an applicator 200G, and the cartridge 300.

The clip unit 100G can include the clip 2, the capsule 3, and a coupler 4G.

The coupler 4G can be different from that of the above-described embodiments in that the coupler can be disposed or stored inside the capsule 3 and the bushing 210G. The coupler 4G can include a distal portion 40G, a pair of retention arms 44G, and a pair of deployment arms 46G.

The distal portion 40G can be the same as the distal portion 40B of the second embodiment except that the distal portion has a size and shape to be insertable into the channel 32 of the capsule 3.

Figure 56:
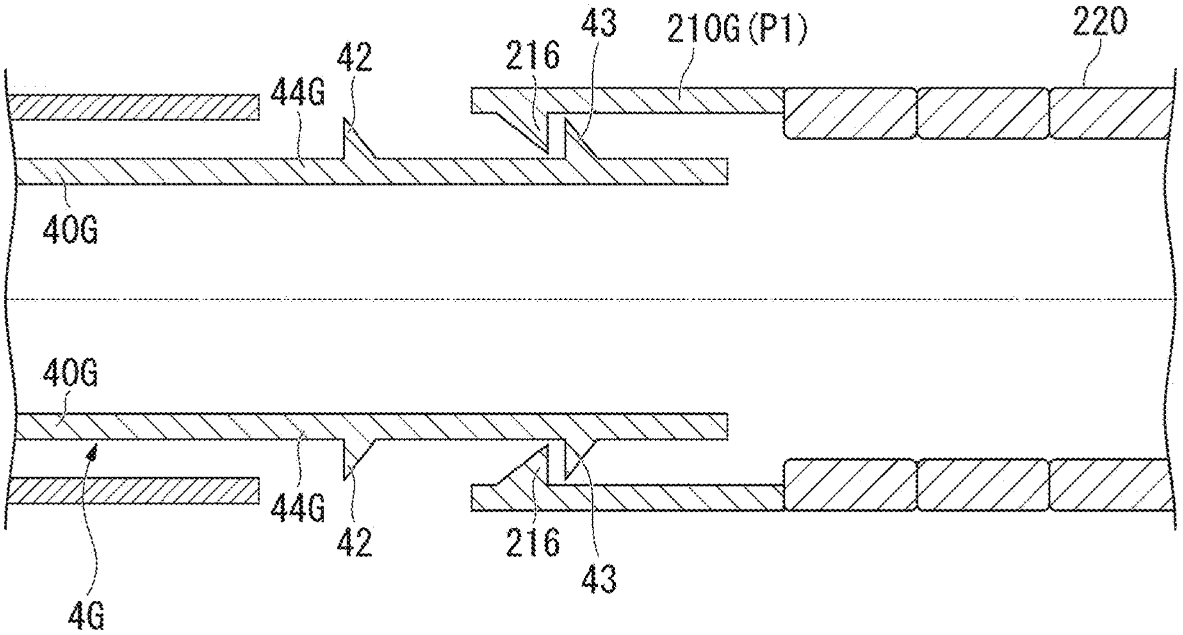
FIG. 56 illustrates an example diagram showing a pair of retention arms of a clip system according to a seventh embodiment of the present disclosure.

FIG. 56 illustrates an example diagram showing a pair of retention arms 44G.

The pair of retention arms 44G can be connected to the bushing 210G of the applicator 200G similarly to the pair of retention arms 44 of the first embodiment. The pair of retention arms 44G can be different from the pair of retention arms 44 of the first embodiment in that the protrusions (the first protrusion 41, the second protrusion 42, and the retention element 43) can be provided not only on the inner peripheral surface 45 but on the outer peripheral surface and protrude outward in the radial direction R.

Figure 57:
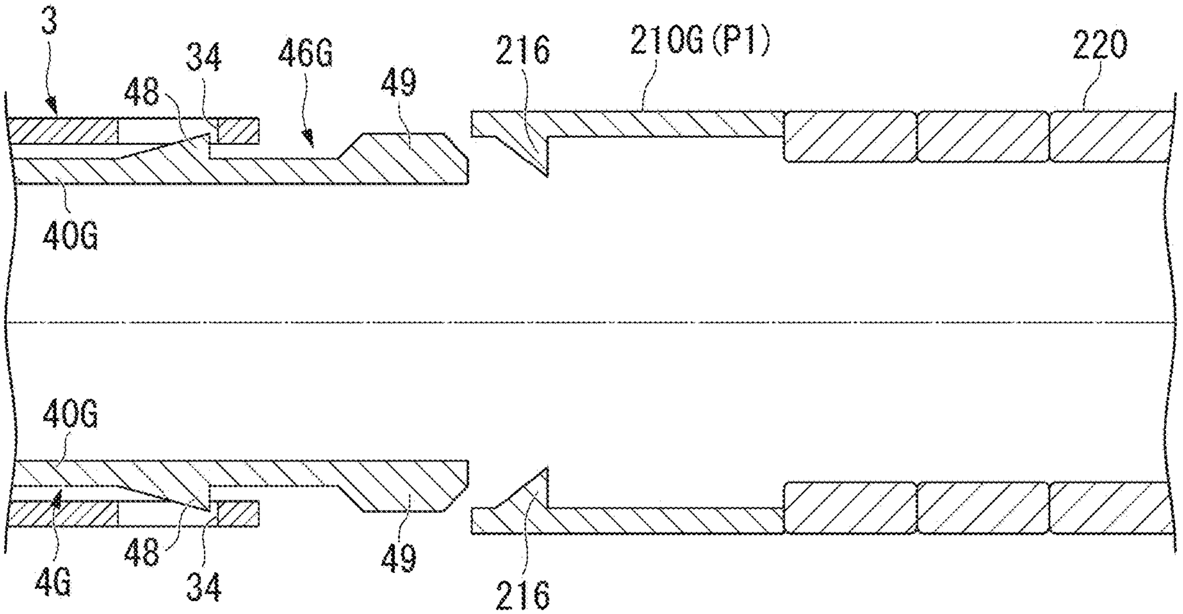
FIG. 57 illustrates an example diagram showing a pair of deployment arms of the same clip system.

FIG. 57 illustrates an example diagram showing the pair of deployment arms 46G.

The pair of deployment arms 46G can be connected to the capsule 3 similarly to the pair of deployment arms 46 of the first embodiment. The pair of deployment arms 46G can be different from the pair of deployment arms 46 of the first embodiment in that the engagement element 48 and the curved portion 49 can be provided not only on the inner peripheral surface but on the outer peripheral surface and protrude outward in the radial direction R.

The applicator 200G can include a sheath 220G, the operating wire 230, and the operating section 240.

The sheath 220G can be flexible and curved to match the curvature of the insertion section of the endoscope. The sheath 220G can extend from the proximal end connected to the operating section 240 that remains outside the body while clipping the target tissue to the distal end including a bushing 210G connecting the applicator 200G to the clip unit 100G.

The bushing 210G can be different from the bushing 210 of the first embodiment in that the projection 216 is provided not on the outer peripheral surface but on the inner peripheral surface and protrudes inward in the radial direction R.

Figure 58:
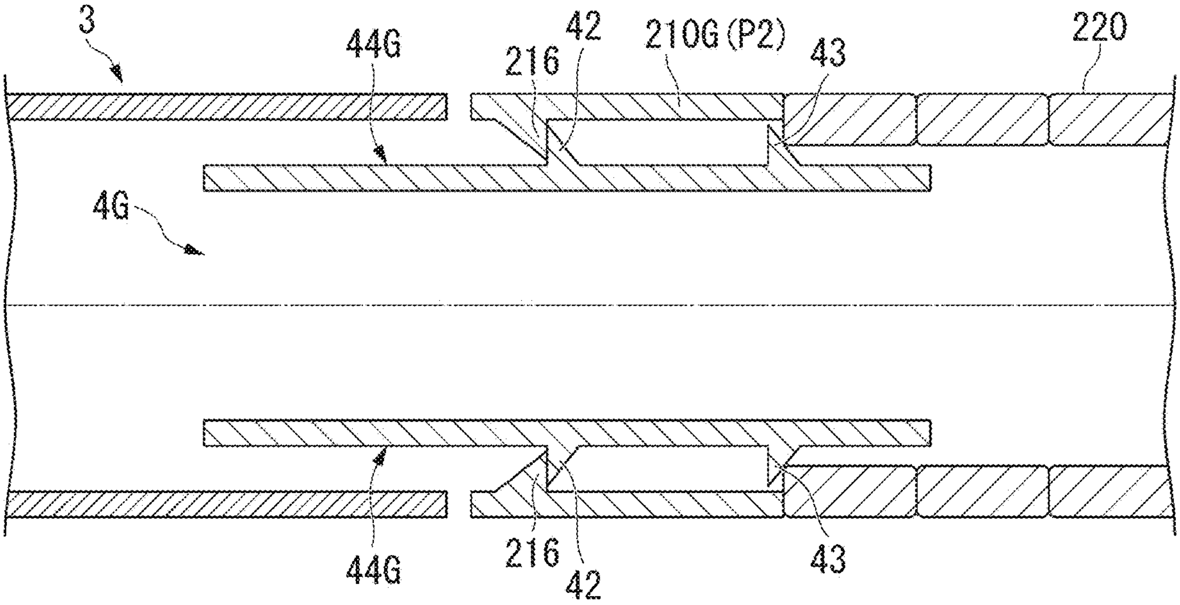
FIG. 58 illustrates an example diagram showing a bushing disposed at a second position.
Figure 59:
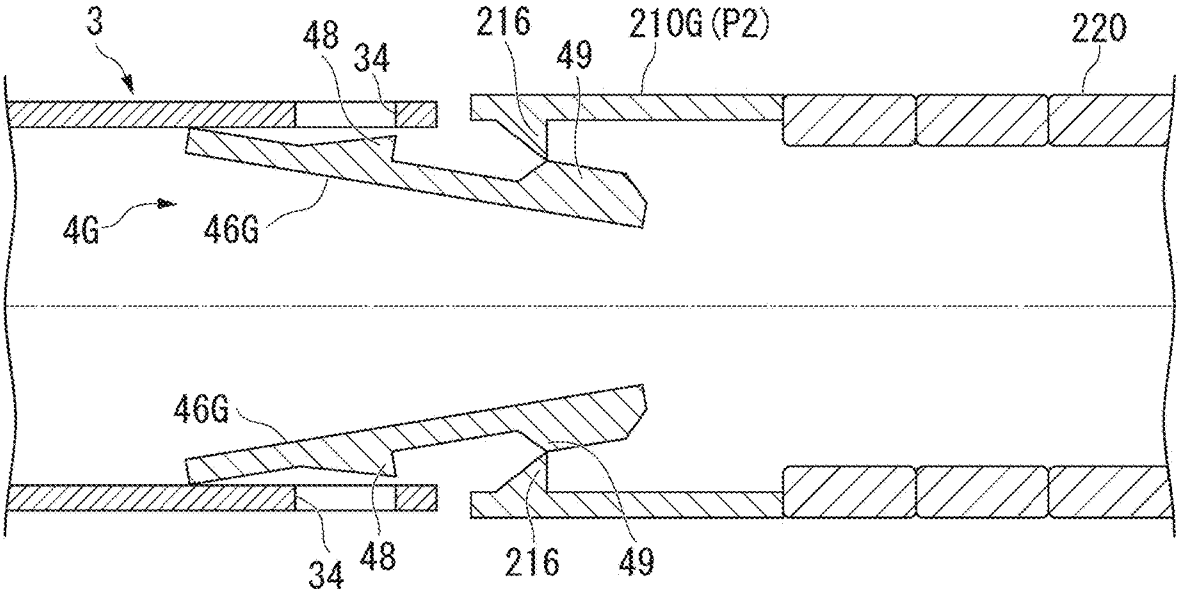
FIG. 59 illustrates an example diagram showing the same bushing disposed at a second position.
Figure 60:
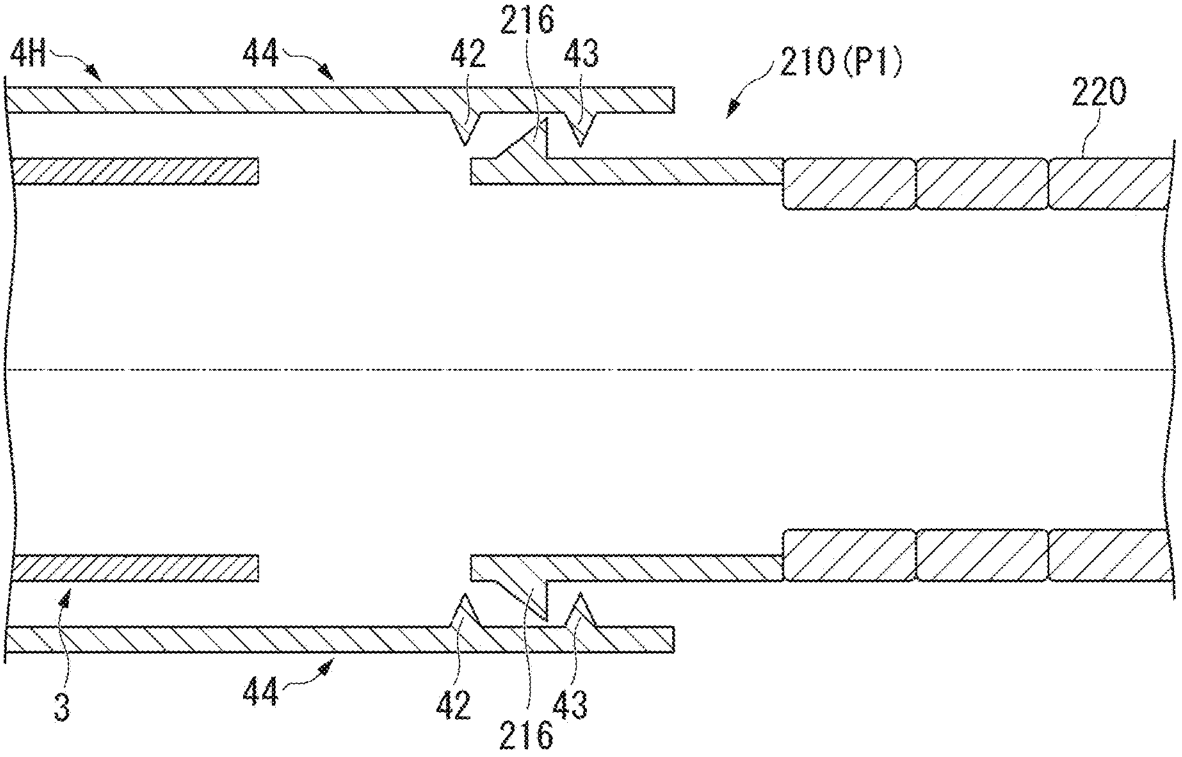
FIG. 60 illustrates an example diagram showing a modified example of a coupler.
Figure 61:
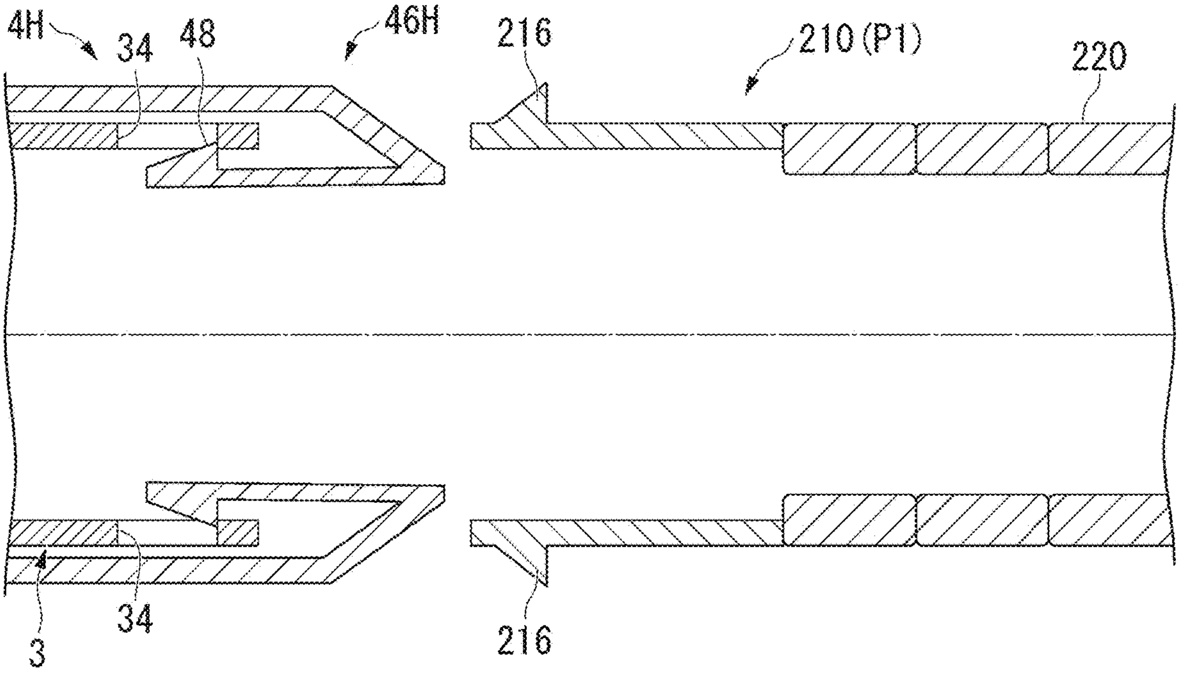
FIG. 61 illustrates an example diagram showing the same modified example of the same coupler.
Figure 62:
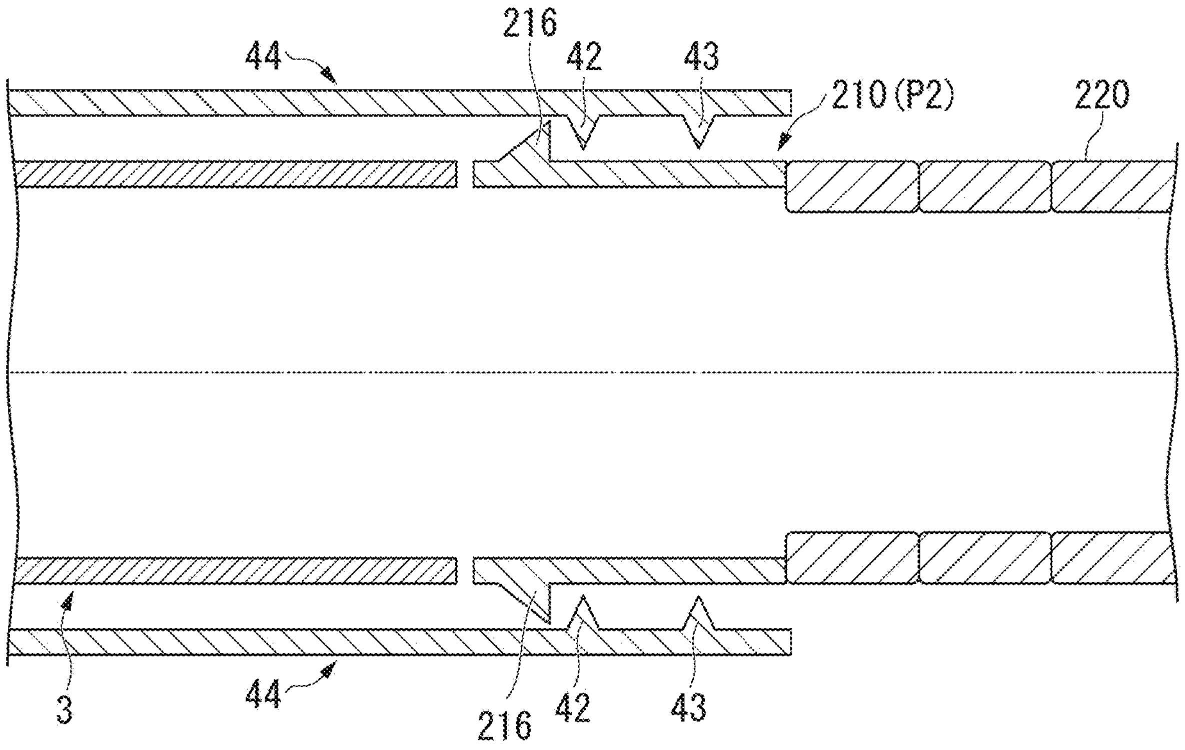
FIG. 62 illustrates an example diagram showing the same modified example of the same coupler.
Figure 63:
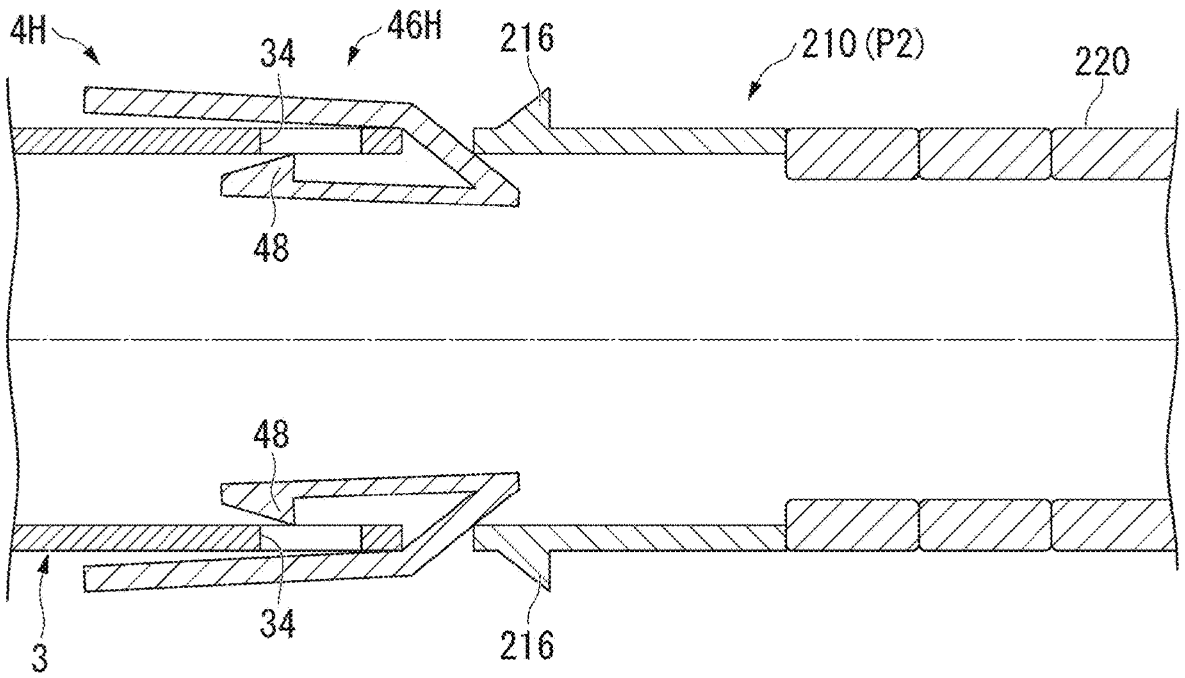
FIG. 63 illustrates an example diagram showing the same modified example of the same coupler.

FIGS. 58 and 59 illustrate example diagrams showing the bushing 210G disposed at the second position P2. Since the curved portion 49 can engage with the projection 216 and the pair of deployment arms 46 can deflect inward in the radial direction R when the bushing 210G is disposed at the second position P2, the engagement elements 48 of the pair of deployment arms 46G can be disengaged from the opening 34 of the capsule 3.

When the bushing 210G is disposed at the second position P2, the coupler 4G can be engaged with and connected to the bushing 210G. On the other hand, the coupler 4G can be disengaged from the capsule 3.

According to the clip system 500G of this embodiment, the coupler 4G can be less likely to fall off from the applicator 200G and can be easily passed through the channel of the endoscope.

Although the seventh embodiment of the present disclosure has been described above in detail with reference to the drawings, the specific configuration is not limited to this embodiment, and design changes can be made within the scope of the present disclosure. Furthermore, the components shown in the embodiments and modified examples can be configured by appropriately combining them.

Modified Example 7-1

In the above-described embodiments, the entire coupler 4G can be disposed in the channel 32 of the capsule 3, but the form of the coupler 4G is not limited thereto. FIGS. 60 to 63 illustrate example diagrams showing a coupler 4H which is a modified example of the coupler 4G. In this example, only a part of the coupler 4H is disposed in the channel 32 of the capsule 3. Specifically, a part including the engagement elements 48 of the pair of retention arms 44H can be disposed in the channel 32. When the bushing 210 is disposed at the second position P2, the coupler 4H can be engaged with and connected to the bushing 210. On the other hand, the coupler 4H can be disengaged from the capsule 3.

ADDITIONAL NOTES

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A clip device, comprising:

a clip including a pair of clip arms;

a capsule including a channel, the channel slidably inserted into a proximal end of each clip arm of the pair of clip arms; and a coupler attached onto the proximal end of the capsule, the coupler including a pair of deployment arms and a pair of retention arms, the pair of retention arms configured to engage with a corresponding portion of an applicator, and wherein a first length of the coupler in a first direction is longer than a second length of the coupler in a second direction in a cross-section, the cross-section crossing the pair of retention arms and the pair of deployment arms and being perpendicular to a longitudinal direction of the coupler.

2. The clip device according to claim 1, wherein the first length is an outer diameter of the coupler in a direction in which the pair of retention arms face each other, and wherein the second length is an outer diameter of the coupler in a direction in which the pair of deployment arms face each other.

3. The clip device according to claim 1, wherein the first length is an outer diameter of the coupler in a direction in which the pair of deployment arms face each other, and wherein the second length is an outer diameter of the coupler in a direction in which the pair of retention arms face each other.

4. The clip device according to claim 1, wherein the coupler includes a radially deformable cylindrical portion provided on a distal end side and the pair of retention arms and the pair of deployment arms provided on a proximal end side.

5. The clip device according to claim 4, wherein the cylindrical portion has a plane, the pair of deployment arms extend from the plane.

6. The clip device according to claim 1, wherein the pair of deployment arms deflect radially inward.

7. The clip system according to claim 1, the capsule includes a pair of openings, the pair of openings locates at a wall of the capsule.

8. The clip system according to claim 7, each deployment arm in the pair of deployment arms includes an engagement element, the engagement element protruding inward from an inner surface of each deployment arm in the pair of deployment arms, the engagement element engaging with the pair of openings of the capsule.

9. The clip system according to claim 1, the pair of deployment arms are configured such that when a predetermined compressing force is applied to the coupler, each deployment arm in the pair of deployment arms slide in a proximal direction along a corresponding portion of the applicator to deflect the pair of deployment arms away from the capsule and separate the coupler from the capsule.

10. A clip system, comprising:

a clip including a pair of clip arms;

a capsule including a channel, the channel slidably inserted into a proximal end of each clip arm of the pair of clip arms;

a coupler attached onto the proximal end of the capsule, the coupler including a pair of deployment arms and a pair of retention arms; and an applicator including a sheath and a wire extending through the sheath, the wire including a connector connected to the pair of clip arms, and wherein a first length of the coupler in a first direction is longer than a second length of the coupler in a second direction in a cross-section, the cross-section crossing the pair of retention arms and the pair of deployment arms and being perpendicular to a longitudinal direction of the coupler.

11. The clip system according to claim 10, wherein the first length is an outer diameter of the coupler in a direction in which the pair of retention arms face each other, and wherein the second length is an outer diameter of the coupler in a direction in which the pair of deployment arms face each other.

12. The clip system according to claim 10, wherein the first length is an outer diameter of the coupler in a direction in which the pair of deployment arms face each other, and wherein the second length is an outer diameter of the coupler in a direction in which the pair of retention arms face each other.

13. The clip system according to claim 10, a distal end of the sheath includes a bushing, the bushing has a projection extending to an outer peripheral surface of the distal end of the sheath, the projection engages with a corresponding retention element of the pair of retention arms.

14. The clip system according to claim 13, the pair of deployment arms and the projection are configured such that when a predetermined compressing force is applied to the coupler while deploying the clip, wherein each deployment arm in the pair of deployment arms slides in a proximal direction along the projection to deflect the deployment arm away from the bushing so that the engagement element is disengaged from the capsule and the coupler is separated from the capsule.

15. The clip system according to claim 13, wherein the bushing includes a second projection located proximally relative to the projection, wherein the bushing is slidable from a first position in which the projection engages with the retention element to a second position in which the projection deflects the pair of deployment arms away from the bushing, and wherein when the bushing is disposed at the second position, the second projection engages with the retention element.

16. The clip system according to claim 13, wherein the bushing includes a convex portion located proximally relative to the projection, and wherein an outer diameter of the convex portion is larger than an outer diameter of the coupler.

17. The clip system according to claim 13, wherein the bushing further includes a coupler accommodation portion configured to accommodate at least a part of the pair of retention arms.

18. The clip system according to claim 13, wherein the coupler is displaceable or deformable with respect to the bushing.

19. The clip system according to claim 10, the capsule includes a pair of openings, the pair of openings locates at a wall of the capsule.

20. The clip system according to claim 19, each deployment arm in the pair of deployment arms includes an engagement element, the engagement element is received in the opening of the capsule.

* * * * *